United States Patent
Gross et al.

(10) Patent No.: US 10,327,812 B2
(45) Date of Patent: Jun. 25, 2019

(54) PERICARDIAL ACCESS DEVICE

(71) Applicant: RAINBOW MEDICAL LTD., Herzliya (IL)

(72) Inventors: Yossi Gross, Moshav Mazor (IL); Michael Kardosh, Kiriat Ono (IL); Amir Kishon, Petach Tikva (IL); Ido Sadan, Tel Aviv (IL); Jonathan Yalom, Tel Aviv (IL); Zev Sohn, Ginot Shomron (IL); Omri Gino, Herzliya (IL); Leonid Yanovitz, Rishon Lezion (IL); Ofir Rimer-Cohen, Rehovot (IL)

(73) Assignee: RAINBOW MEDICAL LTD., Herzliya (IL)

( * ) Notice: Subject to any disclaimer, the term of this patent is extended or adjusted under 35 U.S.C. 154(b) by 332 days.

(21) Appl. No.: 15/338,853

(22) Filed: Oct. 31, 2016

(65) Prior Publication Data
US 2017/0119435 A1 May 4, 2017

Related U.S. Application Data

(60) Provisional application No. 62/250,787, filed on Nov. 4, 2015.

(51) Int. Cl.
*A61B 1/04* (2006.01)
*A61B 17/34* (2006.01)
(Continued)

(52) U.S. Cl.
CPC ...... *A61B 17/3478* (2013.01); *A61B 1/00082* (2013.01); *A61B 1/015* (2013.01);
(Continued)

(58) Field of Classification Search
CPC ............ A61B 1/00094; A61B 1/00154; A61B 17/2478
(Continued)

(56) References Cited

U.S. PATENT DOCUMENTS

| 5,309,896 A | 5/1994 | Moll et al. |
| 5,335,671 A | 8/1994 | Clement |

(Continued)

FOREIGN PATENT DOCUMENTS

| CN | 1628615 A | 6/2005 |
| DE | 10126062 A1 | 12/2001 |

(Continued)

OTHER PUBLICATIONS

An Office Action dated Jul. 27, 2017, which issued during the prosecution of U.S. Appl. No. 14/324,457.

(Continued)

*Primary Examiner* — Matthew J Kasztejna
(74) *Attorney, Agent, or Firm* — Sughrue Mion, PLLC

(57) ABSTRACT

A method is provided for accessing a pericardial space of a subject. The method includes advancing a guide member toward a heart, having (a) a transparent blunt distal end, and (b) a side-facing suction port. During advancing of the guide member, an imaging device disposed in the guide member generates an image of part of the heart. Subsequently to contacting the pericardium with the suction port, the imaging device is retracted proximally in the guide member. Subsequently, a portion of the pericardium is drawn into the guide member through the suction port. Following the drawing of the portion into the guide member, an image of the pericardium disposed within the suction port, is generated. Subsequently, a puncturing element is advanced in the guide member to puncture the portion of the pericardium that is in the guide member. Other applications are also described.

6 Claims, 40 Drawing Sheets

(51) Int. Cl.
  *A61B 1/045* (2006.01)
  *A61B 1/00* (2006.01)
  *A61B 1/015* (2006.01)
  *A61B 1/05* (2006.01)
  *A61B 1/313* (2006.01)
  *A61B 17/00* (2006.01)
  *A61B 17/30* (2006.01)
  *A61B 17/32* (2006.01)
  *A61B 90/00* (2016.01)

(52) U.S. Cl.
  CPC ............ *A61B 1/045* (2013.01); *A61B 1/05* (2013.01); *A61B 1/3132* (2013.01); *A61B 90/37* (2016.02); *A61B 2017/00247* (2013.01); *A61B 2017/00907* (2013.01); *A61B 2017/306* (2013.01); *A61B 2017/320048* (2013.01); *A61B 2017/3486* (2013.01); *A61B 2017/3492* (2013.01)

(58) Field of Classification Search
  USPC ............ 600/107, 114–115, 146, 201–219; 604/164.01–164.04
  See application file for complete search history.

(56) References Cited

U.S. PATENT DOCUMENTS

| | | |
|---|---|---|
| 5,336,252 A | 8/1994 | Cohen |
| 5,458,112 A | 10/1995 | Weaver et al. |
| 5,478,309 A | 12/1995 | Sweezer et al. |
| 5,584,803 A | 12/1996 | Stevens et al. |
| 5,634,895 A | 6/1997 | Igo et al. |
| 5,792,153 A | 8/1998 | Swain et al. |
| 5,827,216 A | 10/1998 | Igo et al. |
| 6,004,269 A | 12/1999 | Crowley et al. |
| 6,083,166 A | 7/2000 | Holdaway et al. |
| 6,162,195 A | 12/2000 | Igo et al. |
| 6,210,323 B1 | 4/2001 | Gilhuly et al. |
| 6,216,704 B1 | 4/2001 | Ingle et al. |
| 6,231,518 B1 | 5/2001 | Grabek et al. |
| 6,398,795 B1 | 6/2002 | McAlister et al. |
| 6,463,332 B1 | 10/2002 | Aldrich |
| 6,632,227 B2 | 10/2003 | Adams |
| 6,695,764 B2 | 2/2004 | Silverman et al. |
| 6,721,663 B1 | 4/2004 | Roberts et al. |
| 6,757,969 B1 | 7/2004 | Chan |
| 6,837,848 B2 | 1/2005 | Bonner et al. |
| 6,908,427 B2 | 6/2005 | Fleener et al. |
| 7,186,252 B2 | 3/2007 | Nobis et al. |
| 8,602,973 B2 | 12/2013 | Wendlandt |
| 8,617,150 B2 | 12/2013 | Tsoref et al. |
| 8,956,346 B2 | 2/2015 | Tsoref et al. |
| 9,242,122 B2 | 1/2016 | Tsoref et al. |
| 2001/0041821 A1 | 11/2001 | Wilk |
| 2001/0053909 A1 | 12/2001 | Nakada et al. |
| 2002/0002371 A1 | 1/2002 | Acker et al. |
| 2003/0074057 A1 | 4/2003 | Rosengart |
| 2003/0187460 A1 | 10/2003 | Chin et al. |
| 2004/0087831 A1 | 5/2004 | Michels et al. |
| 2004/0098030 A1 | 5/2004 | Makower et al. |
| 2004/0216748 A1* | 11/2004 | Chin .............. A61B 17/00008 128/898 |
| 2006/0079868 A1 | 4/2006 | Makin et al. |
| 2006/0189840 A1 | 8/2006 | Walsh et al. |
| 2007/0004984 A1 | 1/2007 | Crum et al. |
| 2007/0010793 A1* | 1/2007 | Callas .............. A61B 17/3478 604/500 |
| 2007/0129719 A1 | 6/2007 | Kendale et al. |
| 2007/0265610 A1 | 11/2007 | Thapliyal et al. |
| 2008/0071289 A1 | 3/2008 | Cooper et al. |
| 2008/0243162 A1 | 10/2008 | Shibata et al. |
| 2008/0312664 A1 | 12/2008 | Bardsley et al. |
| 2009/0048514 A1 | 2/2009 | Azhari |
| 2009/0209986 A1 | 8/2009 | Stewart et al. |
| 2010/0125281 A1 | 5/2010 | Jacobson et al. |
| 2010/0217151 A1 | 8/2010 | Gostout et al. |
| 2011/0009853 A1 | 1/2011 | Bertolero et al. |
| 2011/0251524 A1 | 10/2011 | Azhari |
| 2011/0270239 A1 | 11/2011 | Werneth |
| 2011/0282203 A1 | 11/2011 | Tsoref et al. |
| 2012/0088964 A1 | 4/2012 | Gambhir et al. |
| 2012/0116158 A1 | 5/2012 | Hale et al. |
| 2013/0103028 A1 | 4/2013 | Tsoref et al. |
| 2013/0338545 A1 | 12/2013 | Azhari et al. |
| 2014/0012083 A1* | 1/2014 | Chin .............. A61B 1/00154 600/114 |
| 2015/0313633 A1 | 11/2015 | Gross et al. |
| 2015/0313634 A1 | 11/2015 | Gross et al. |
| 2015/0359558 A1 | 12/2015 | Kardosh et al. |
| 2016/0107003 A1 | 4/2016 | Tsoref et al. |

FOREIGN PATENT DOCUMENTS

| | | |
|---|---|---|
| DE | 102006058447 A1 | 6/2008 |
| EP | 1518498 A1 | 3/2005 |
| JP | 11123197 A | 5/1999 |
| JP | 2011177597 | 9/2011 |
| WO | 9600038 A1 | 1/1996 |
| WO | 9640368 A1 | 12/1996 |
| WO | 9923812 A2 | 5/1999 |
| WO | 9959663 A1 | 11/1999 |
| WO | 2007127664 A1 | 11/2007 |
| WO | 2011130456 A1 | 10/2011 |
| WO | 2011141918 A2 | 11/2011 |
| WO | 2013121424 A2 | 8/2013 |
| WO | 2014015259 A1 | 1/2014 |
| WO | 2015170256 A2 | 11/2015 |

OTHER PUBLICATIONS

An Office Action dated Jul. 23, 2018, which issued during the prosecution of U.S. Appl. No. 15/338,853.
An Office Action dated Mar. 22, 2018, which issued during the prosecution of U.S. Appl. No. 14/324,457.
An Office Action dated Sep. 22, 2017, which issued during the prosecution of U.S. Appl. No. 14/704,857.
An Office Action dated Mar. 15, 2018, which issued during the prosecution of U.S. Appl. No. 14/704,857.
An Invitation to pay additional fees dated Jul. 28, 2015, which issued during the prosecution of Applicant's PCT/IB2015/053280.
European Search Opinion dated Oct. 8, 2015, which issued during the prosecution of Applicant's European App No. 13749108.
A Written Opinion dated Nov. 9, 2015, which issued during the prosecution of Applicant's PCT/IB2015/053280.
An International Search Report and a Written Opinion both dated Sep. 18, 2015, which issued during the prosecution of Applicant's PCT/IB2015/055132.
Mi-eye product brochure. Trice Medical. 5 pgs. Total.
U.S. Appl. No. 62/250,787, filed Nov. 4, 2015.
U.S. Appl. No. 62/021,327, filed Jul. 7, 2014.
U.S. Appl. No. 61/988,457, filed May 5, 2014.
An Office Action dated May 8, 2014, which issued during the prosecution of U.S. Appl. No. 13/015,951.
An Office Action together with the English translation dated Sep. 19, 2018, which issued during the prosecution of Chinese Patent Application No. 201580036627.5.

\* cited by examiner

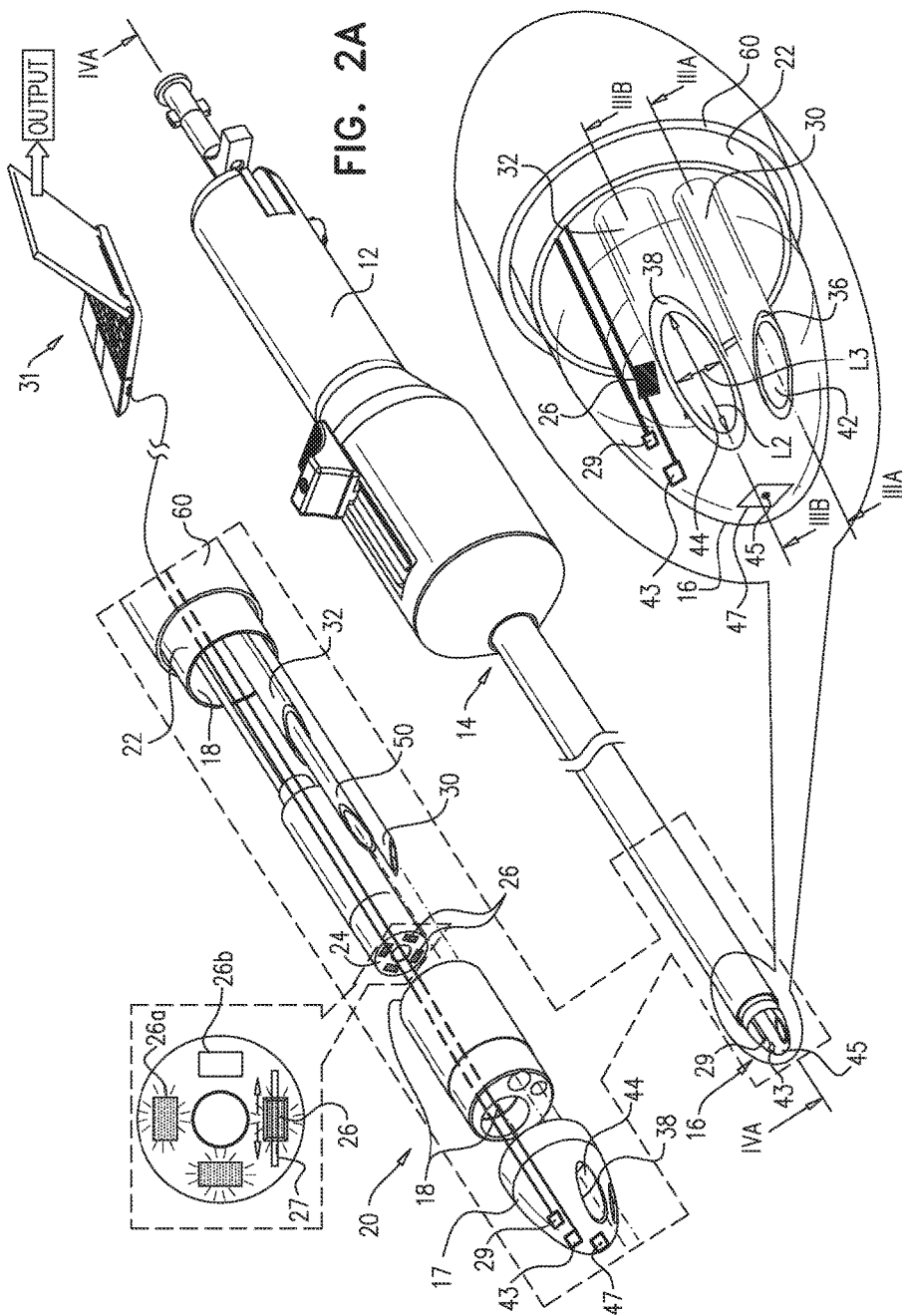

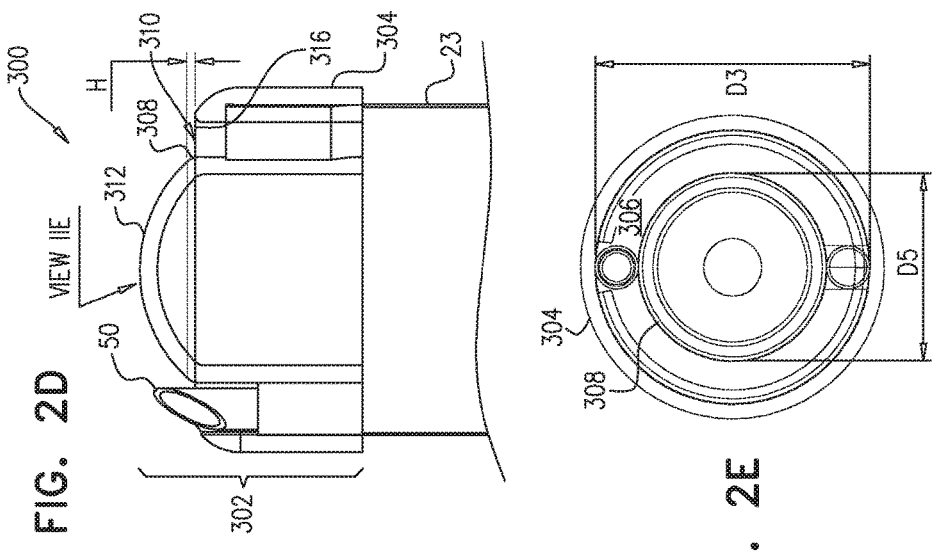
FIG. 2D
FIG. 2E
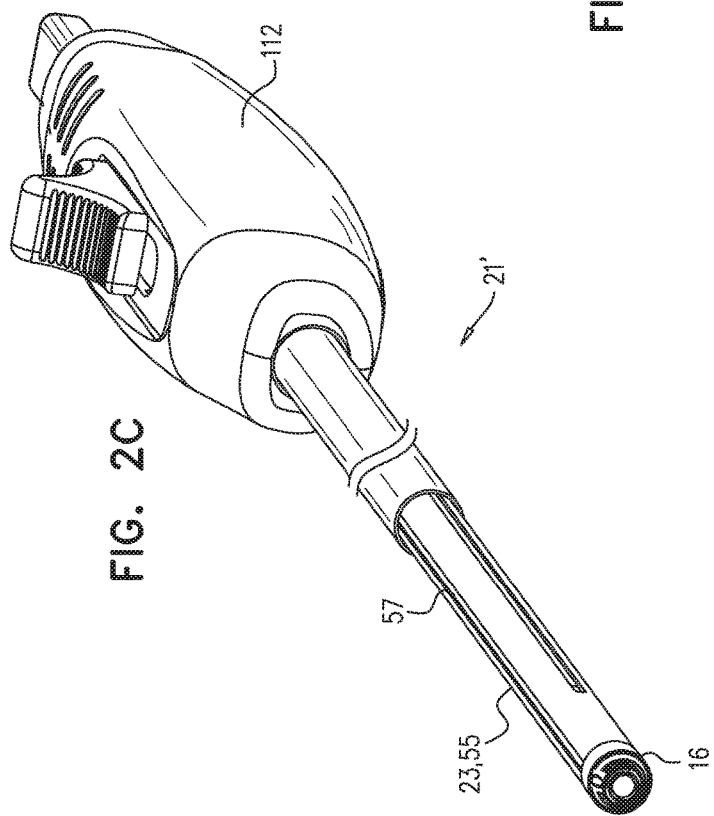
FIG. 2C

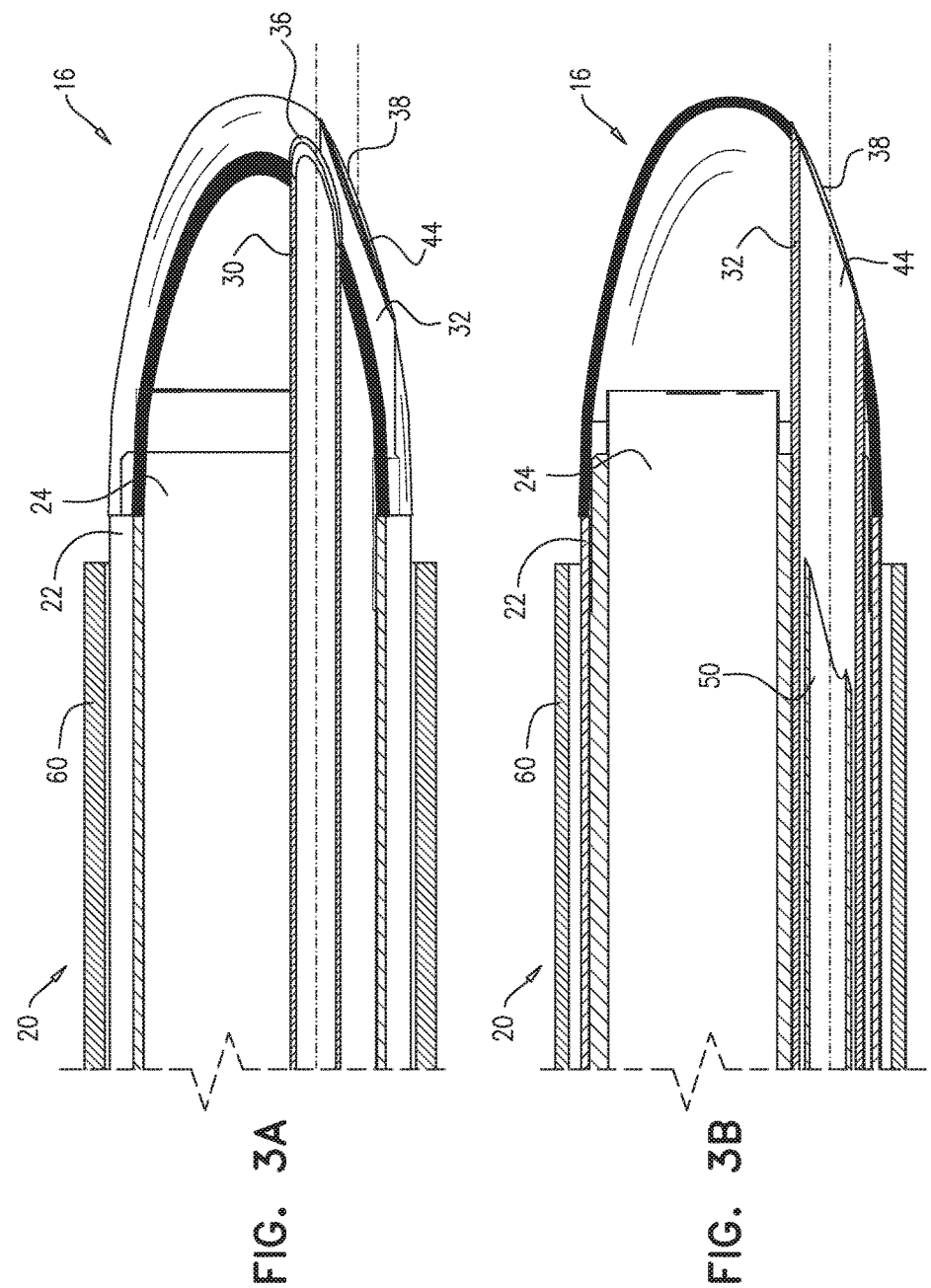

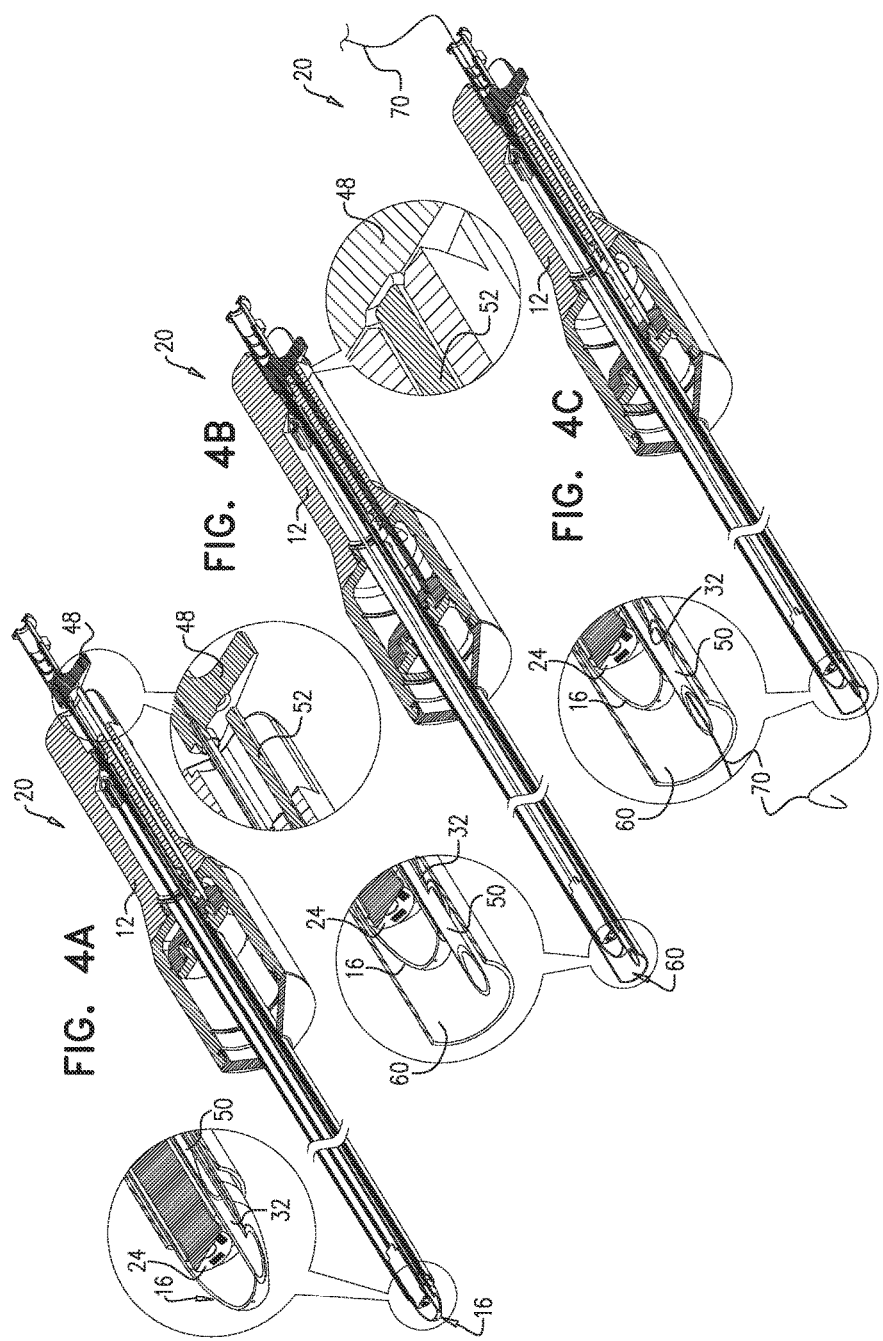

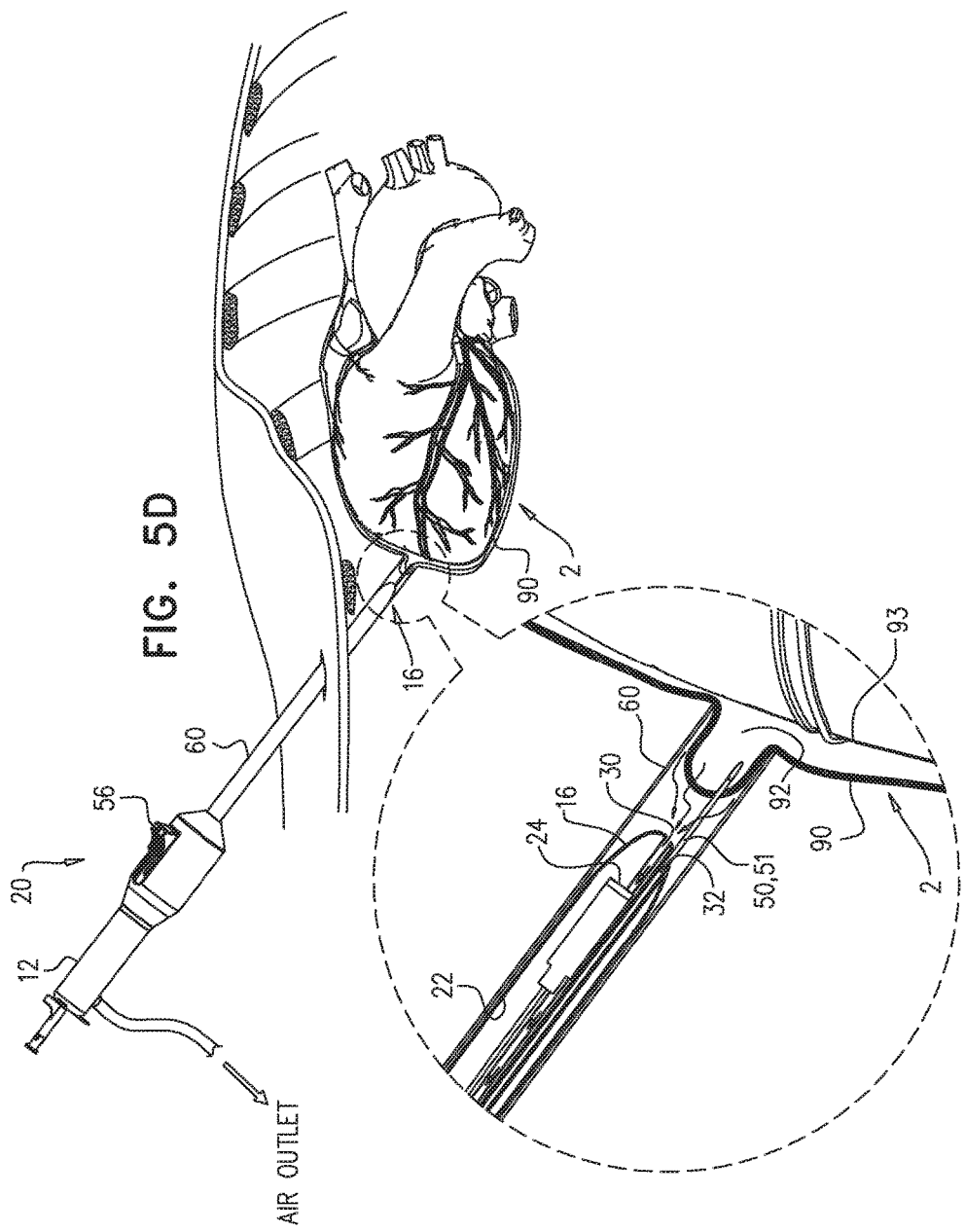

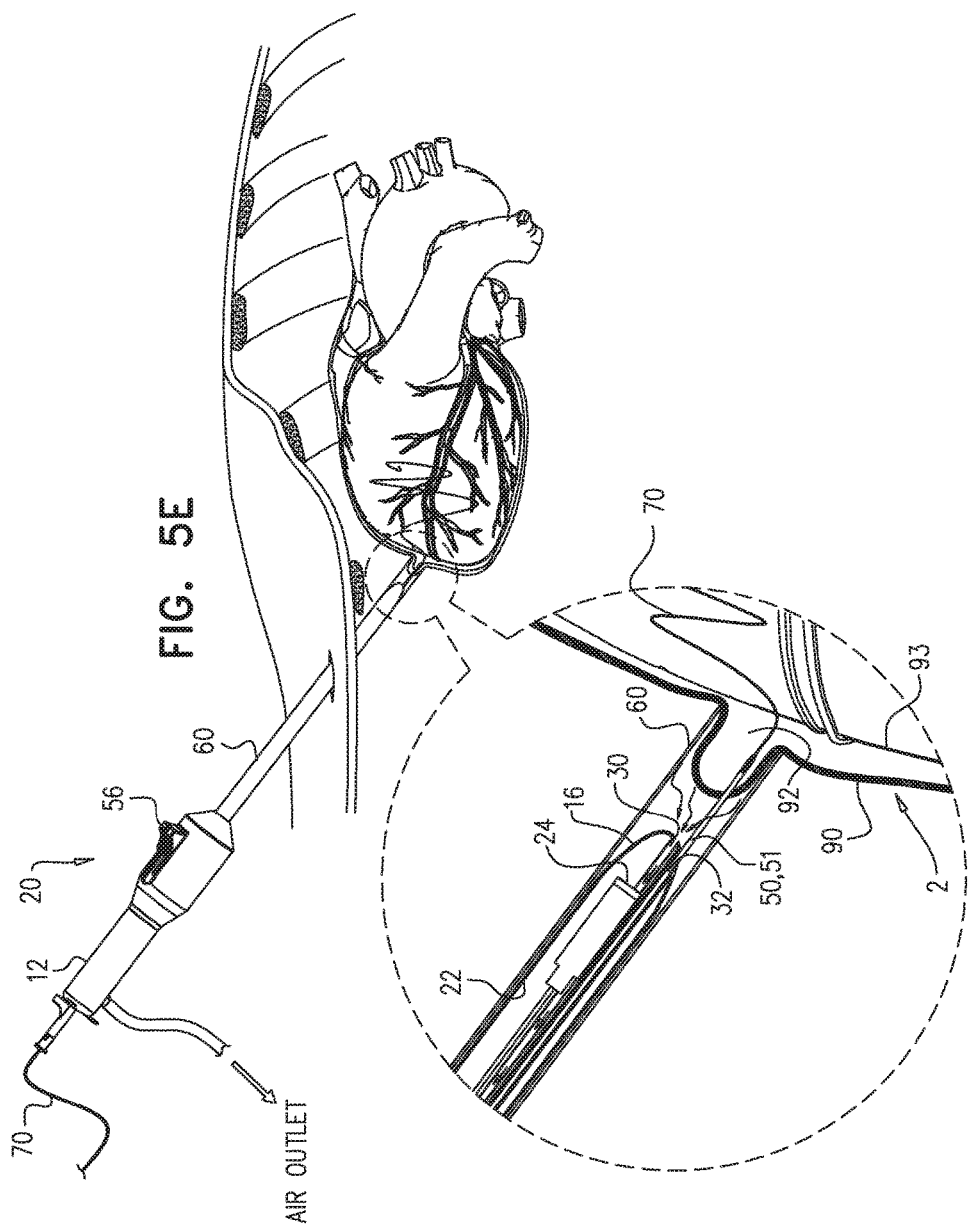

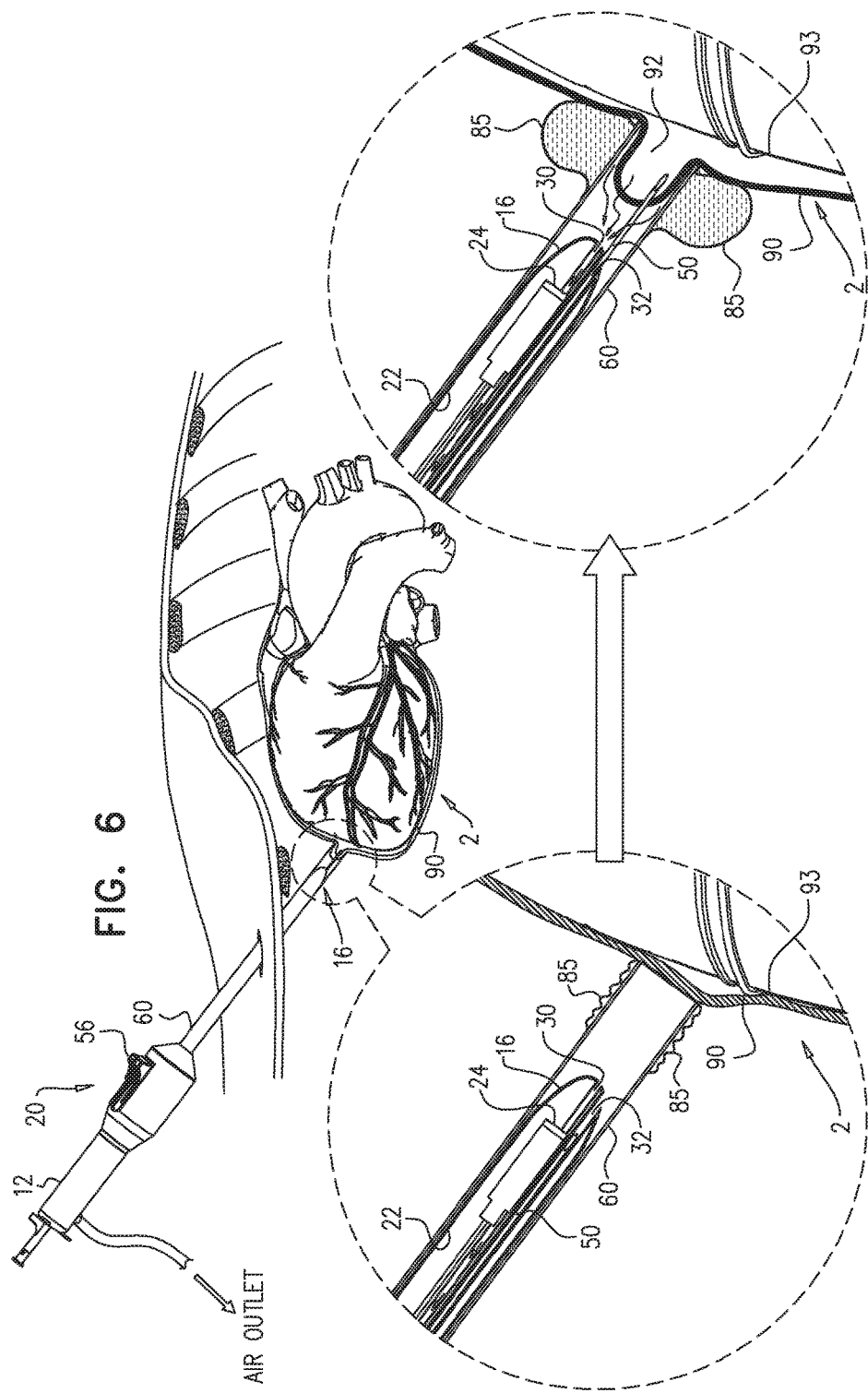

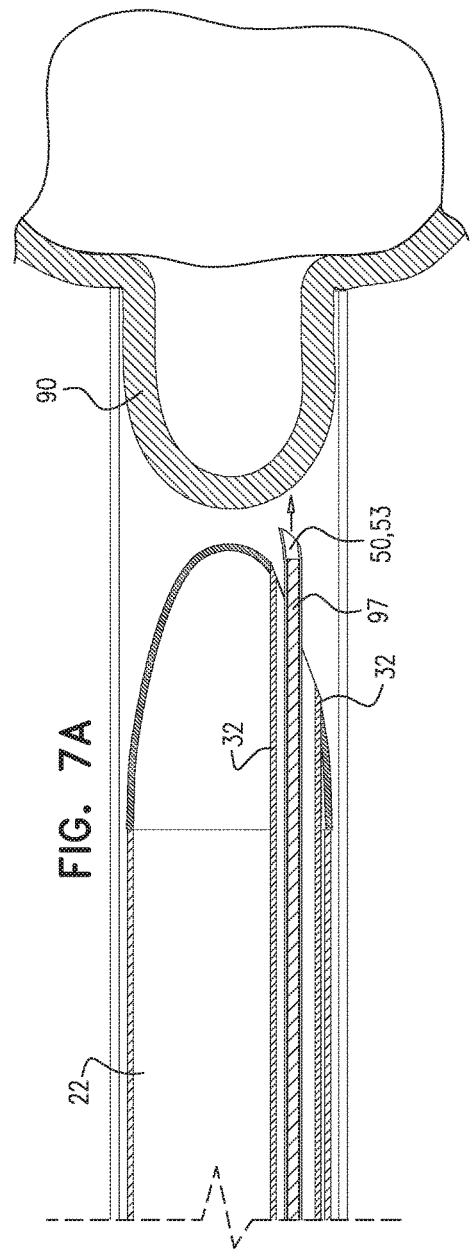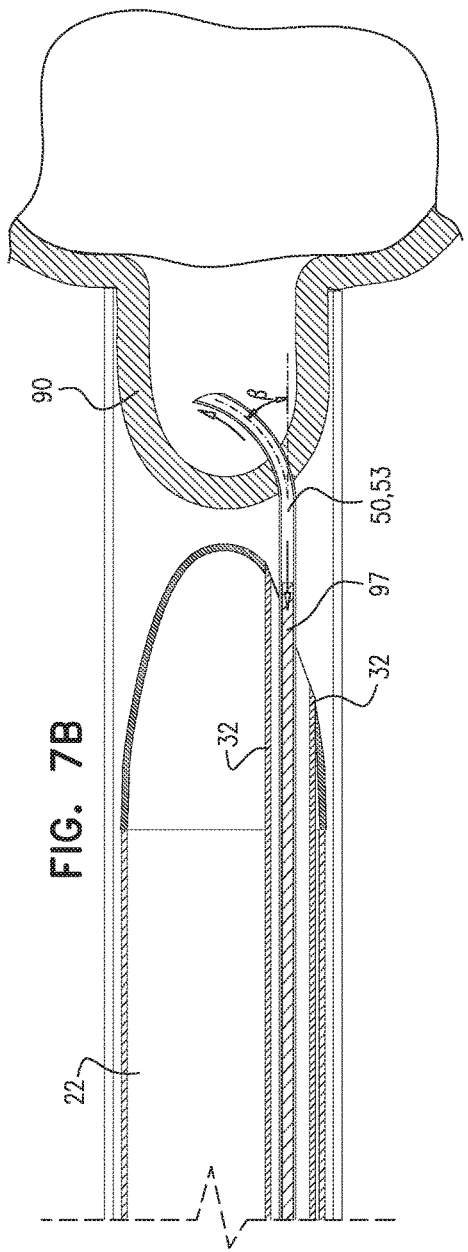

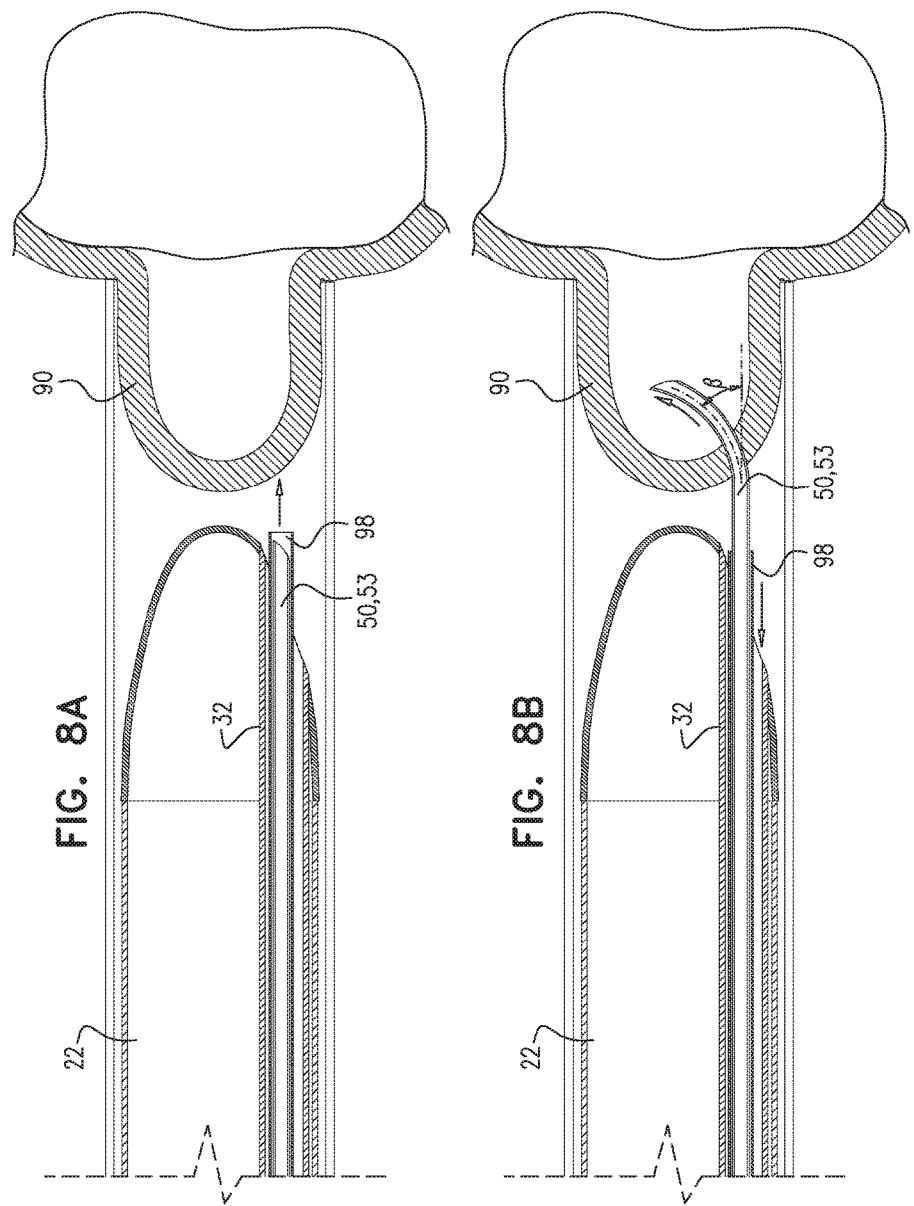

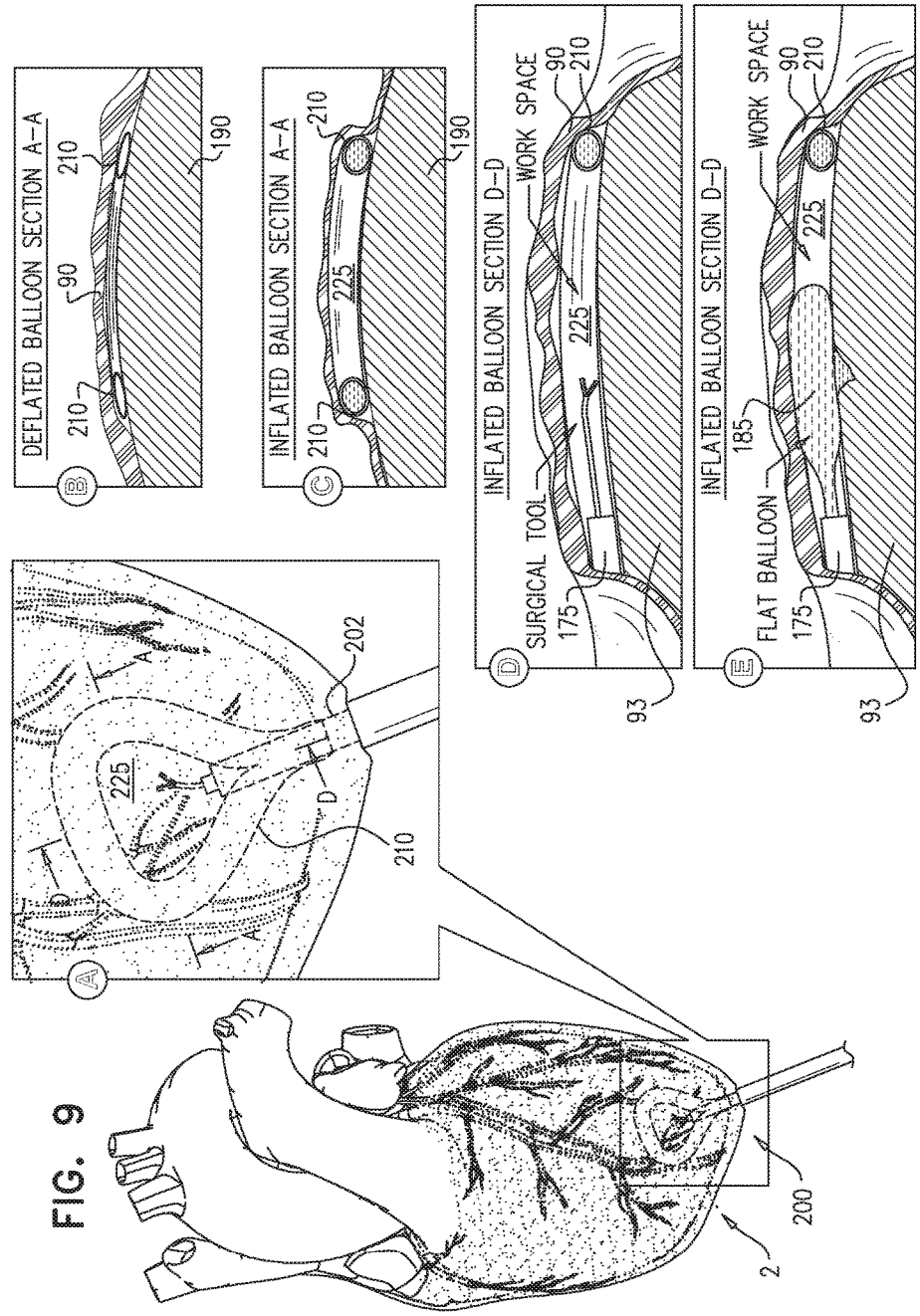

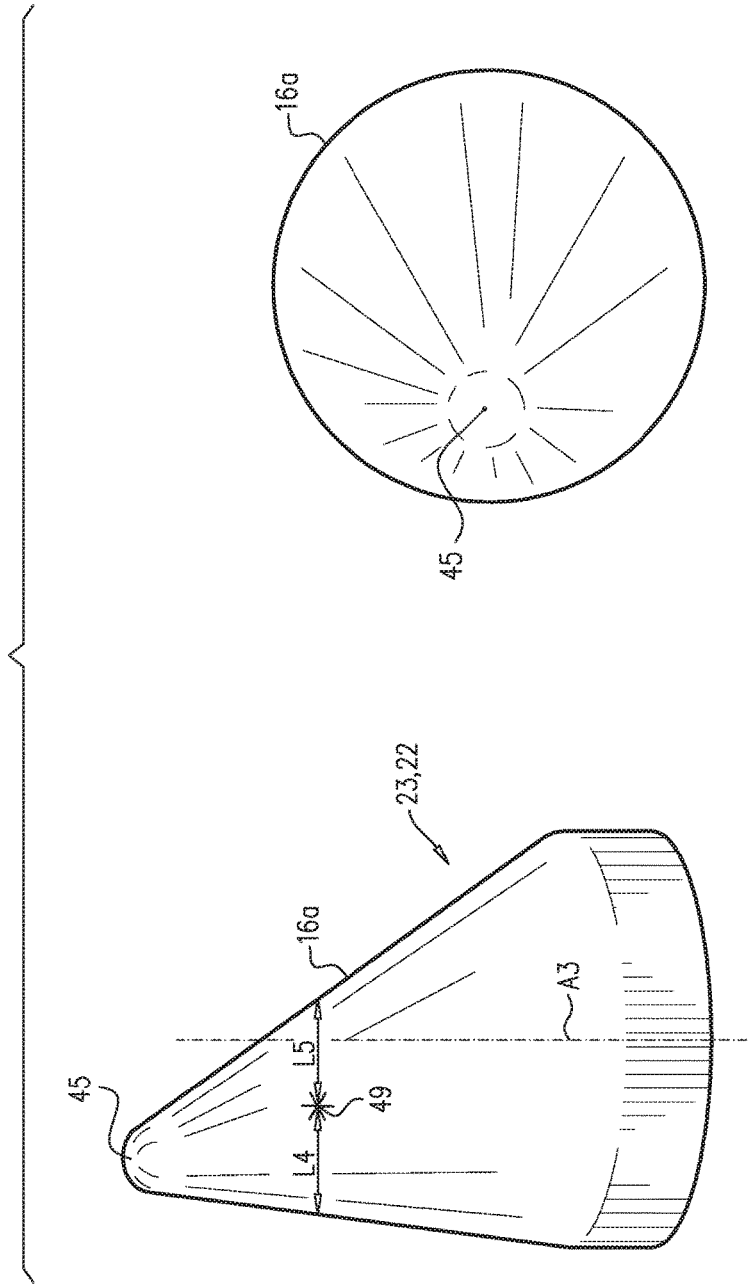

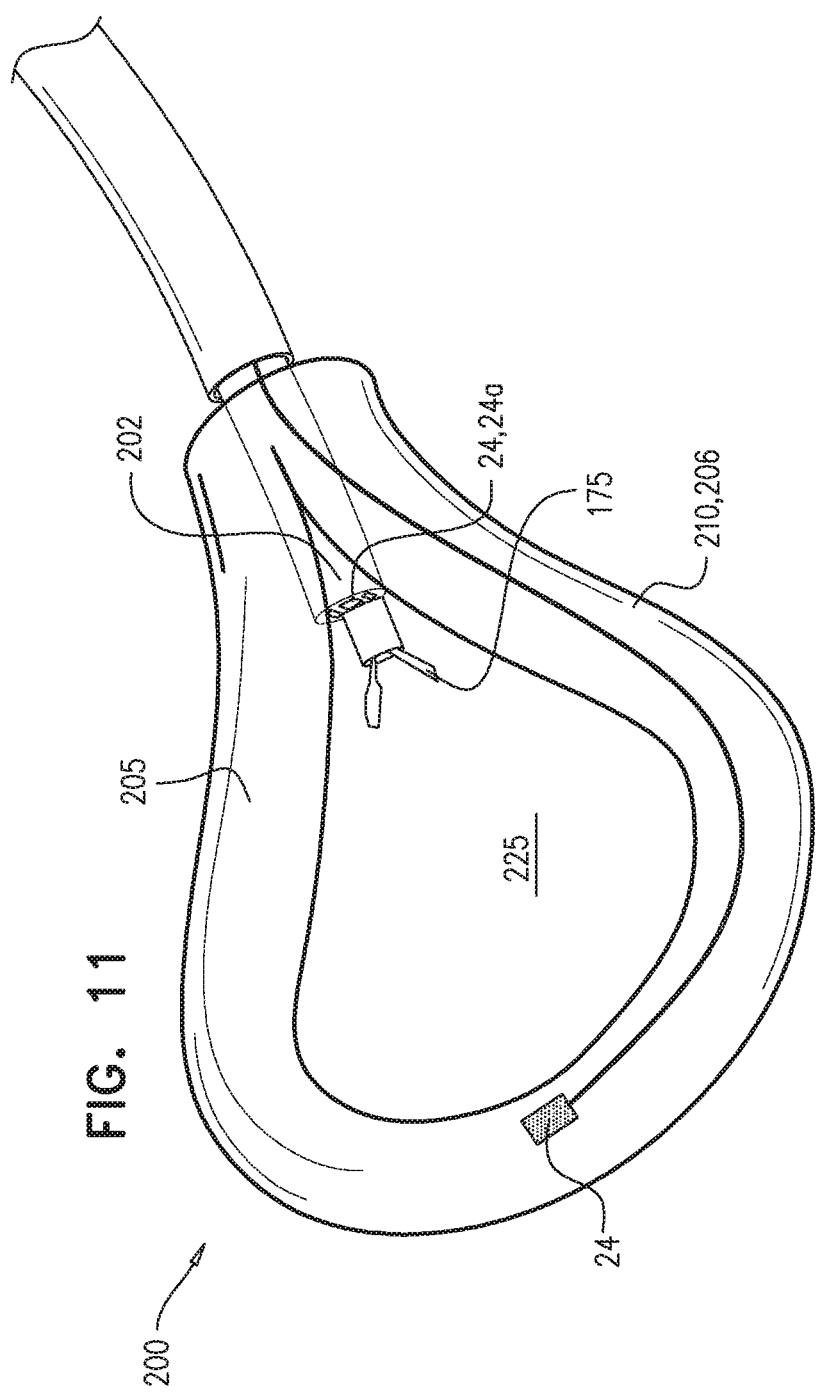

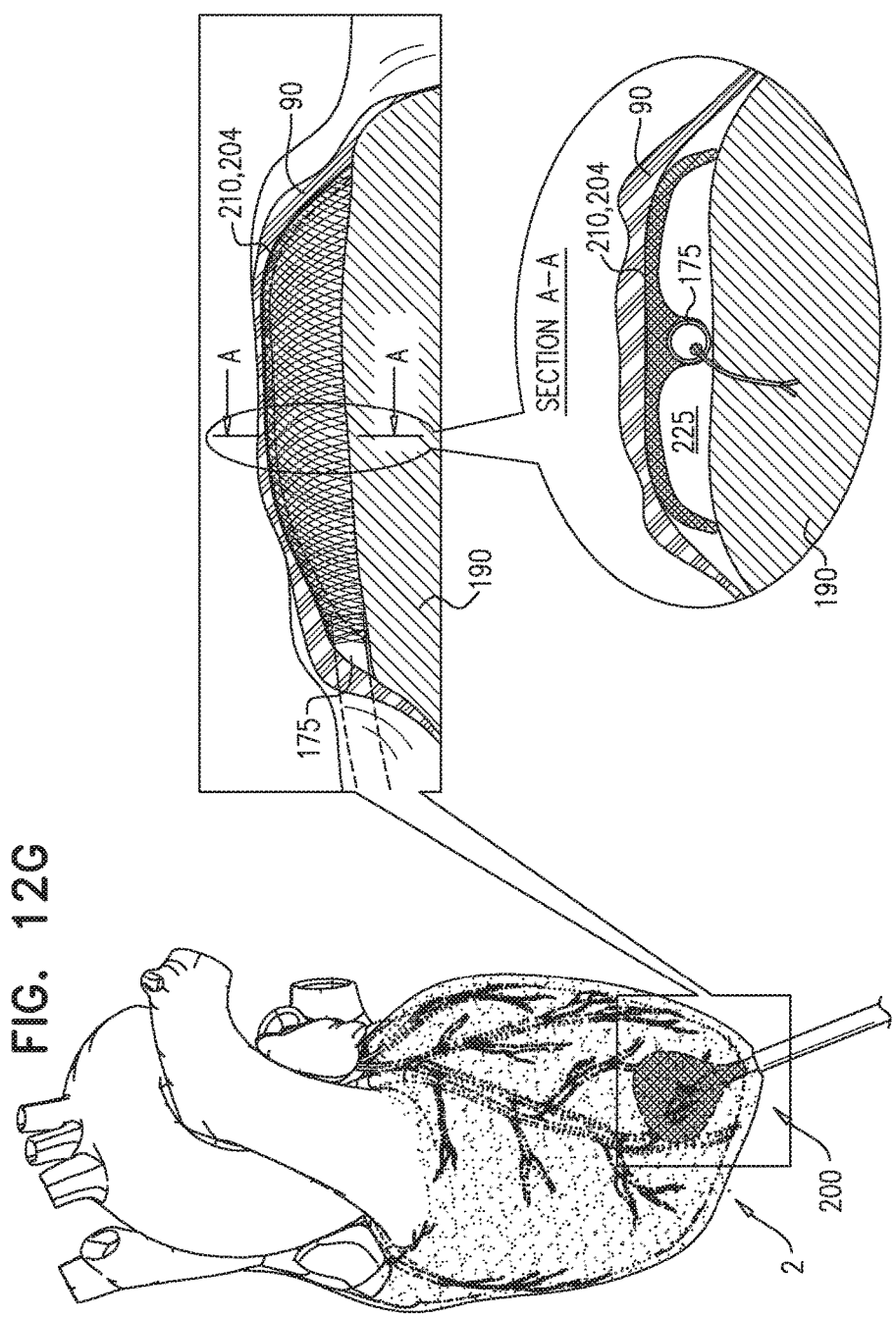

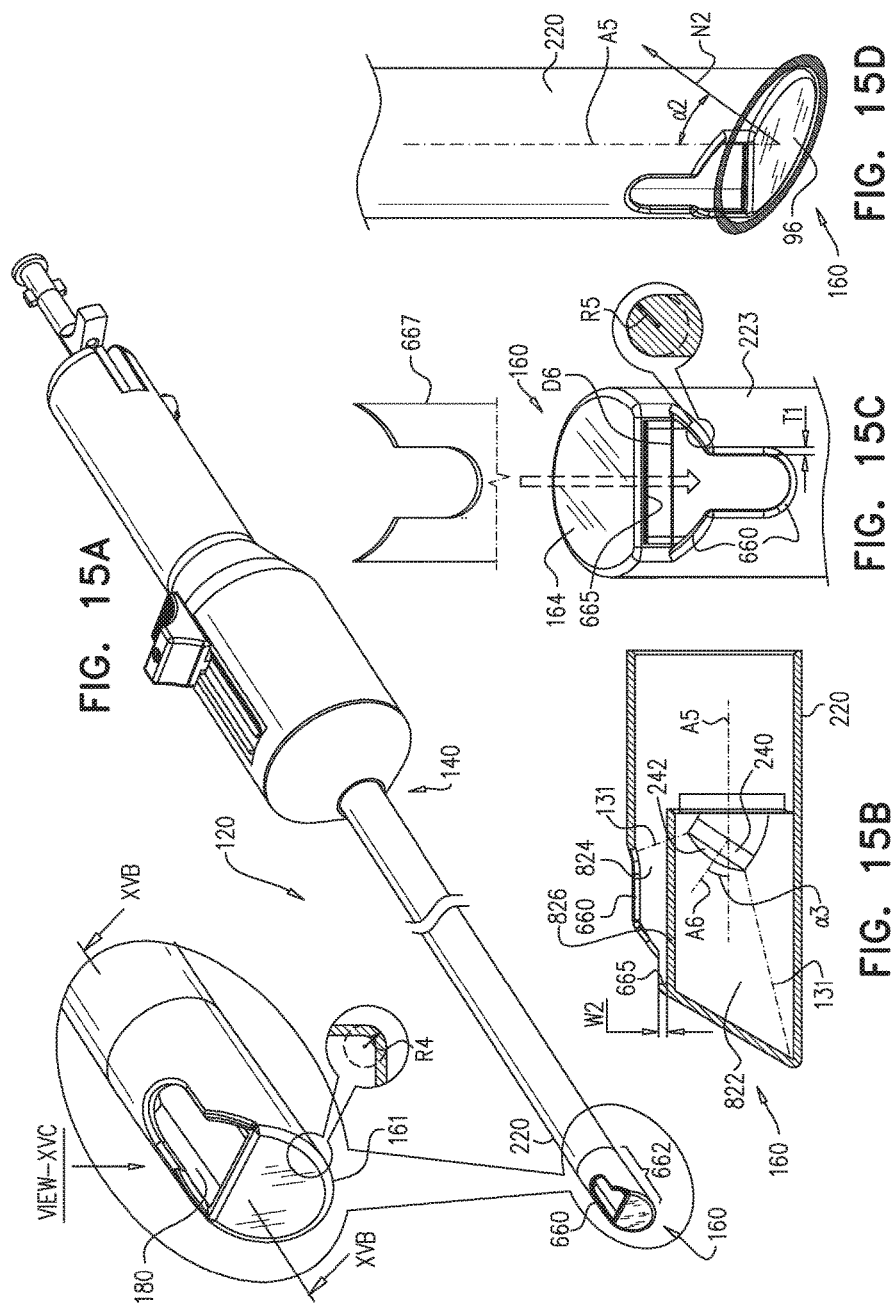

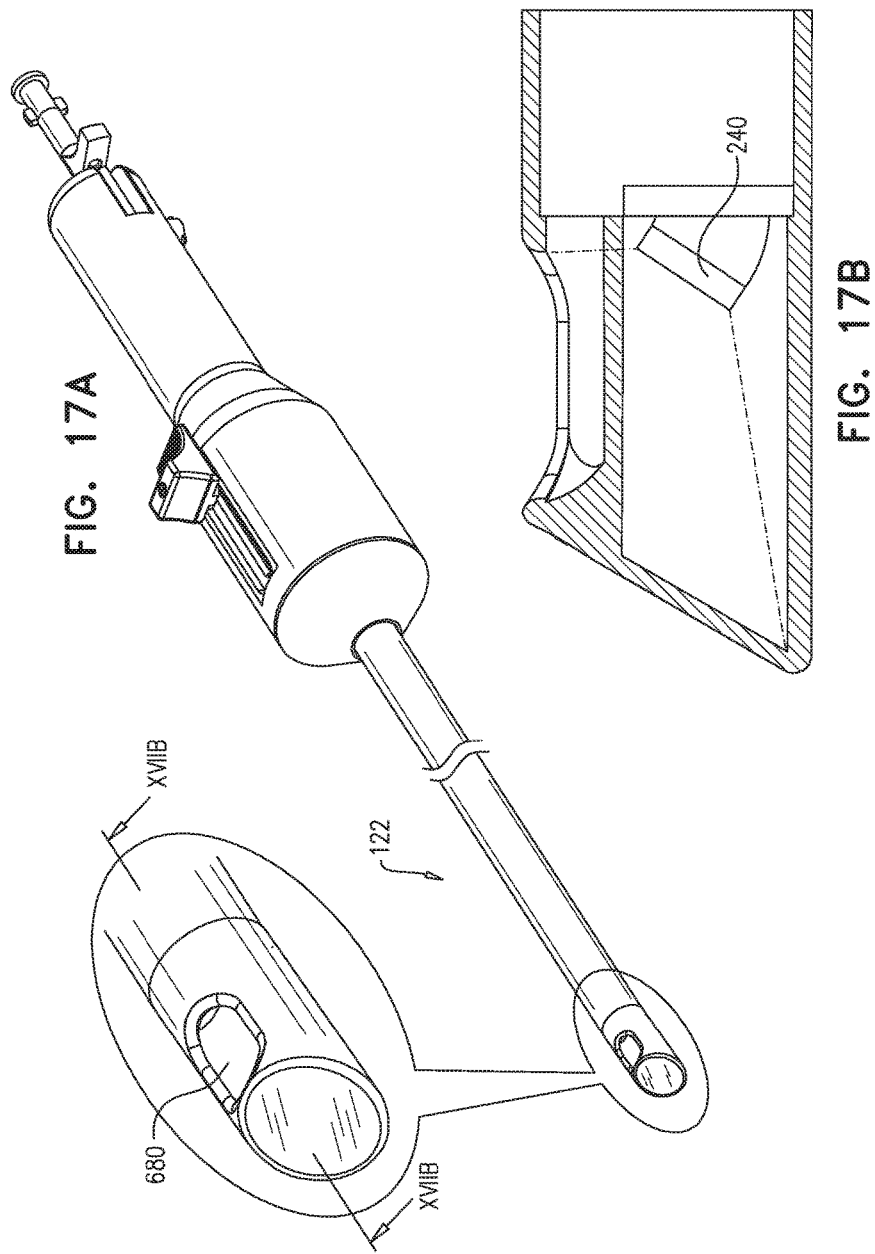

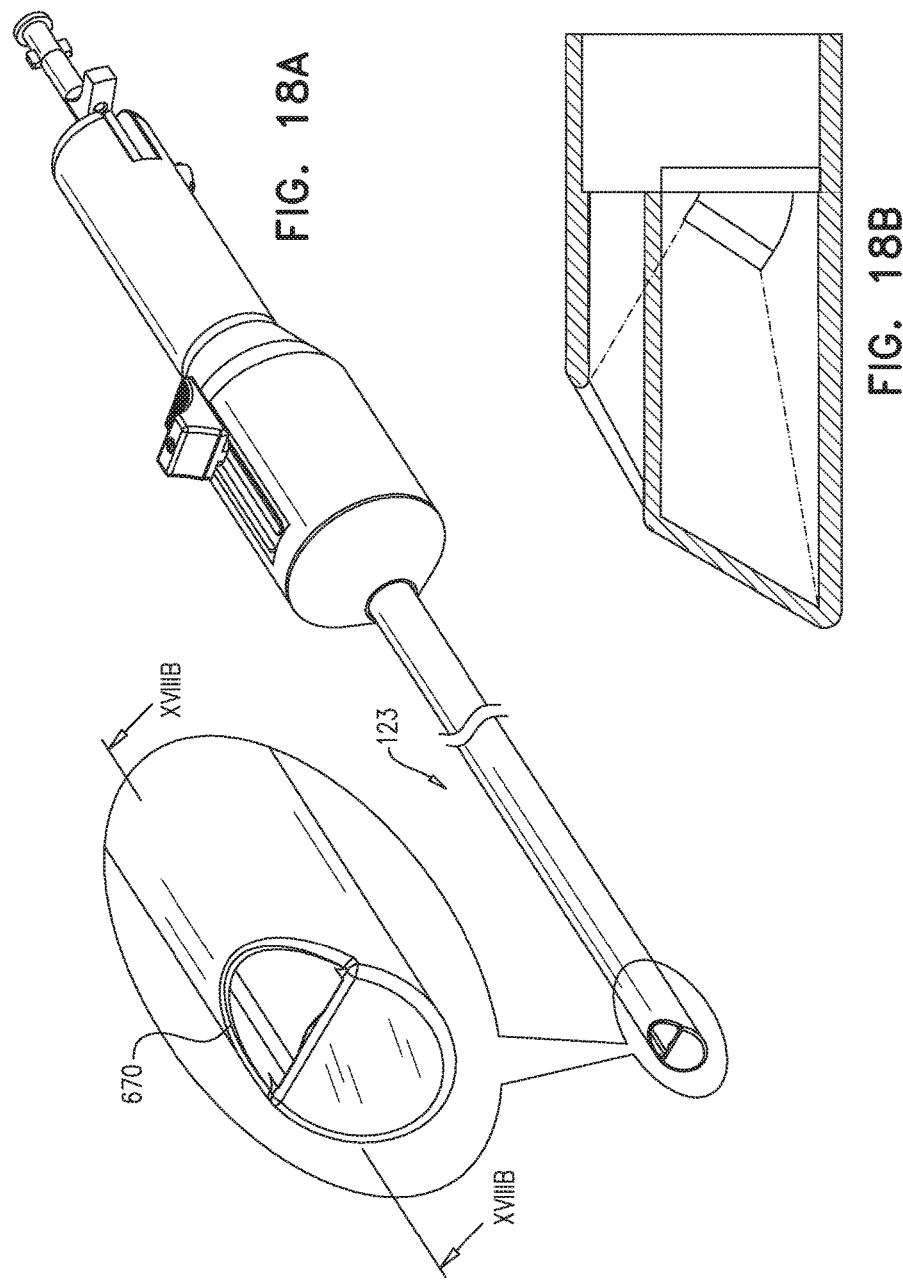

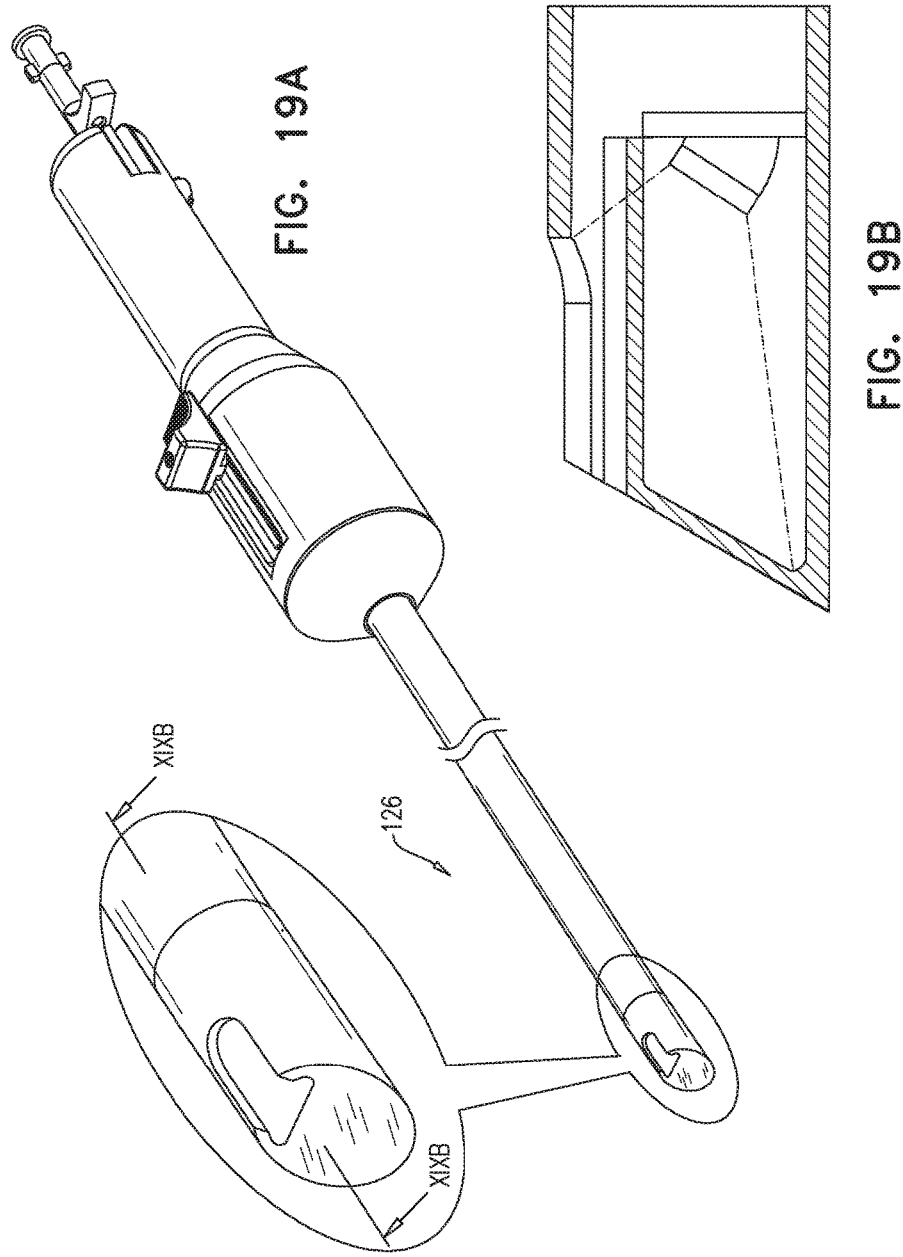

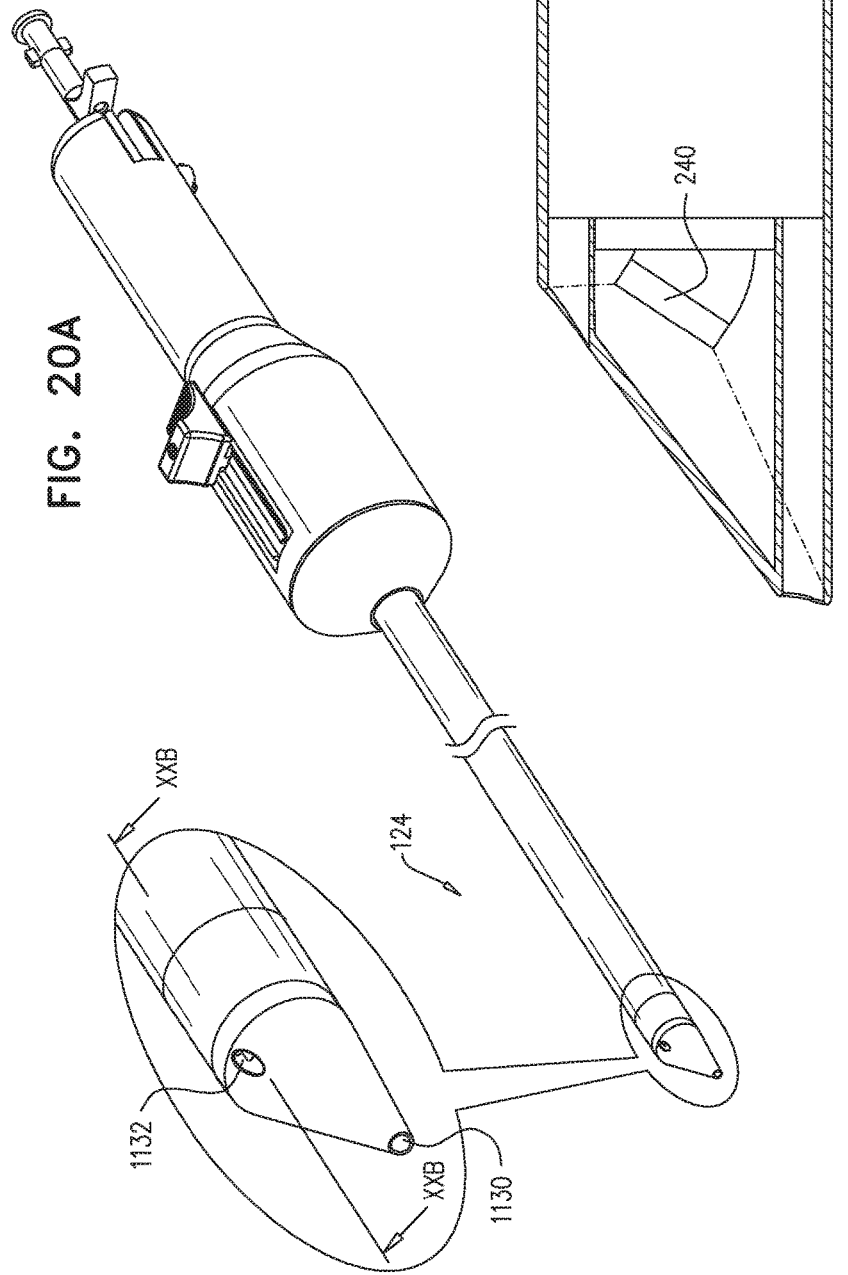

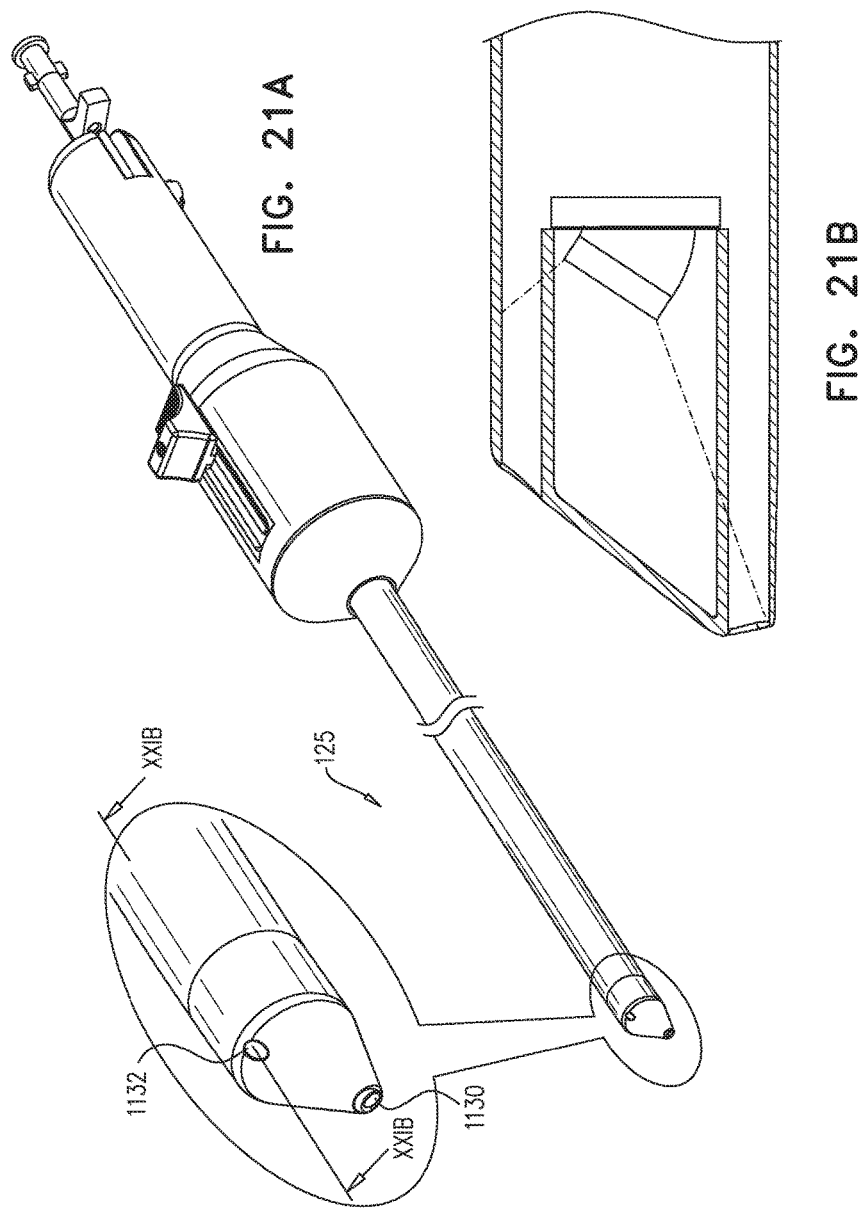

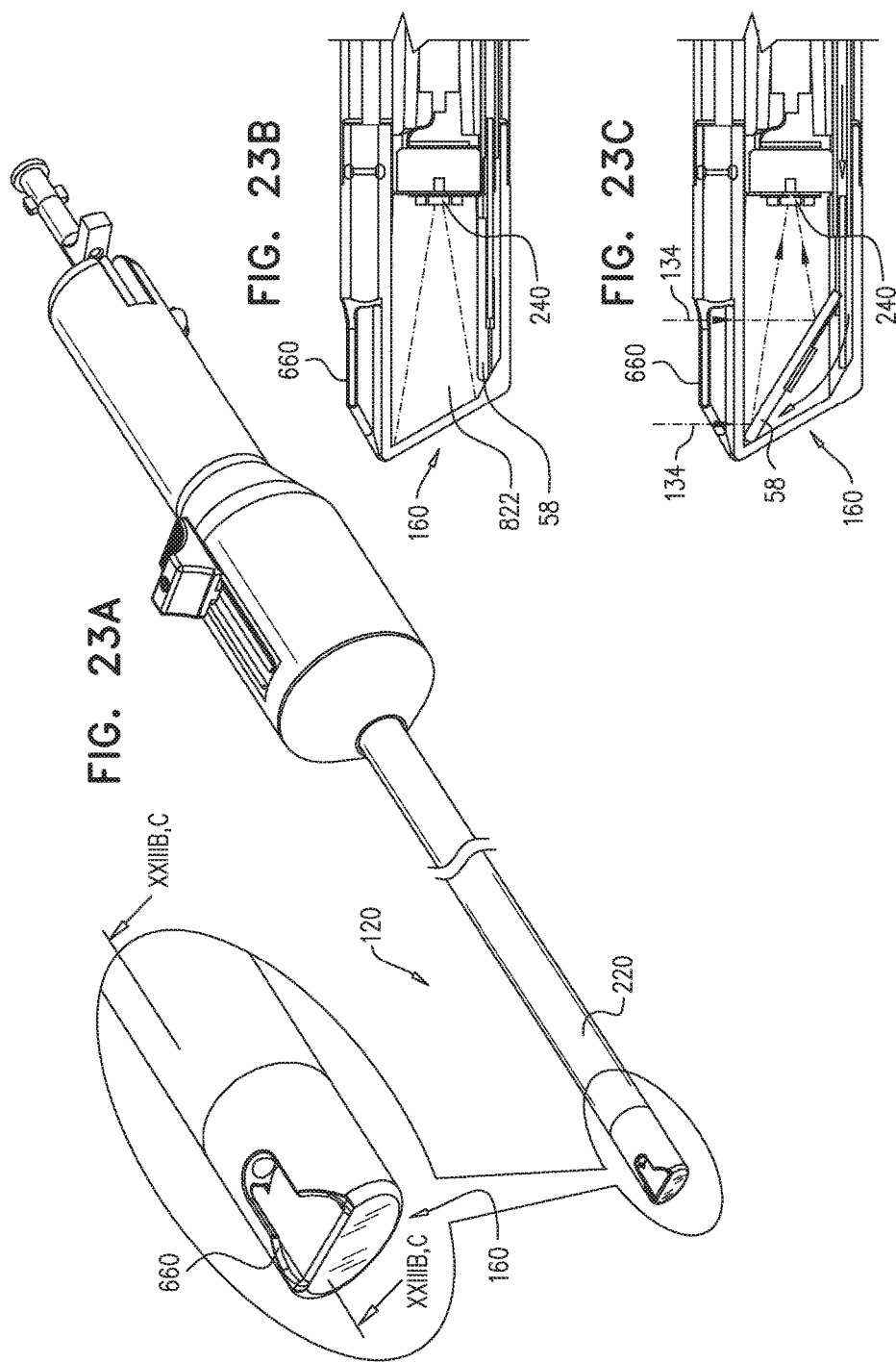

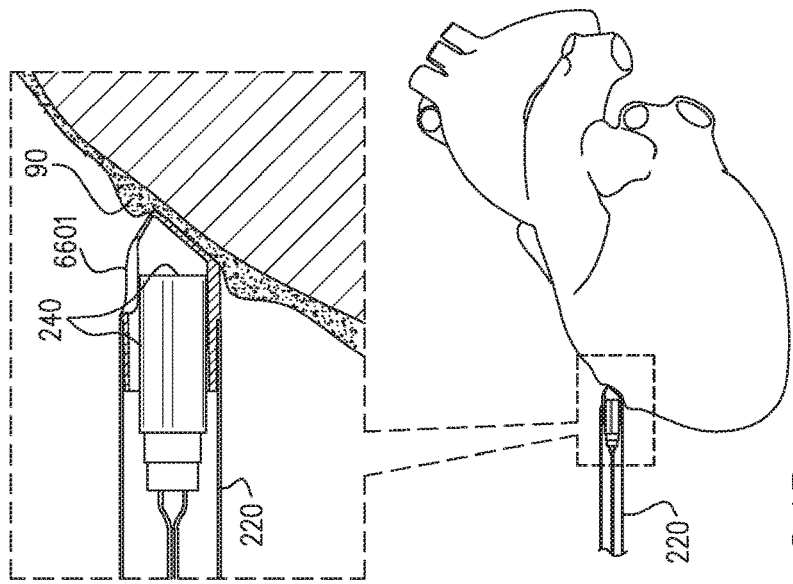
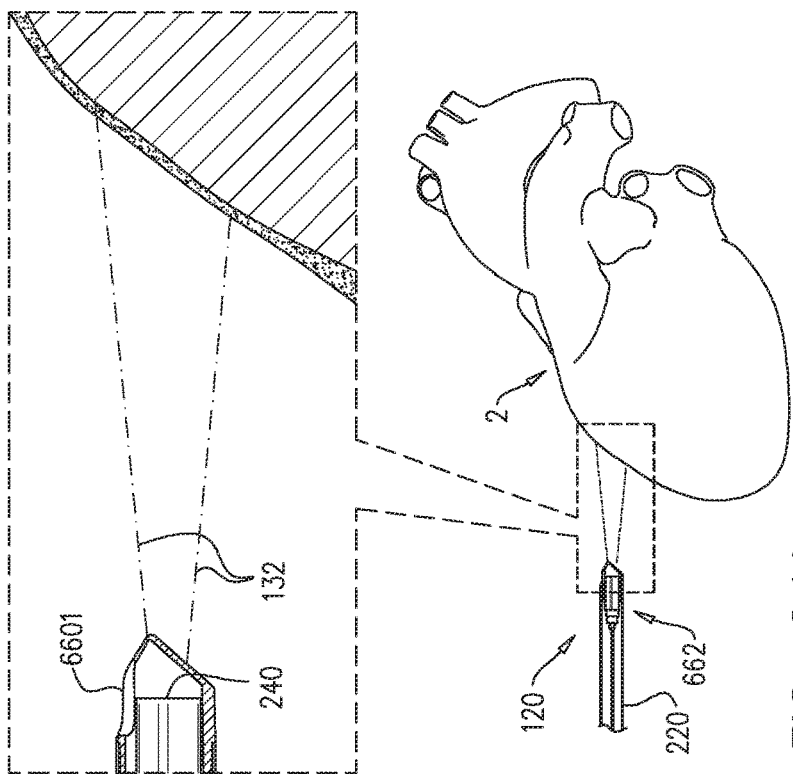
FIG. 24A
FIG. 24B

PERICARDIAL ACCESS DEVICE

CROSS-REFERENCE TO RELATED APPLICATIONS

The present application claims priority from U.S. Provisional Patent Application No. 62/250,787 to Gross et al., entitled "Pericardial Access Device," filed Nov. 4, 2015.

The present application is related to:

(a) U.S. Provisional Application No. 61/988,457 to Gross et al., entitled "Pericardial Access Device," filed May 5, 2014, (b) U.S. application Ser. No. 14/324,457 to Gross et al., which published as US 2015-0313633, entitled "Pericardial Access Device," filed Jul. 7, 2014, (c) U.S. Provisional Application No. 62/021,327 to Gross et al., entitled "Left Atrial Appendage Closure," filed on Jul. 7, 2014, (d) PCT application PCT/IB2015/053280 to Gross et al., which published as WO 2015-170256, entitled "Pericardial Access Device," filed May 5, 2015, and (e) U.S. application Ser. No. 14/704,857 to Gross et al., which published as US 2015-0313634, entitled "Pericardial Access Device," filed May 5, 2015.

Each of the above applications is incorporated herein by reference.

FIELD OF THE INVENTION

Applications of the present invention relate generally to cardiac procedures and specifically to apparatus and methods for accessing a pericardial region, e.g., a pericardial cavity of a subject.

BACKGROUND

The heart is enclosed in a double layered membrane termed the pericardium. The pericardium and its serous fluid protect the heart and lubricate the moving surfaces of the heart. The pericardium is composed of two layers: the outermost fibrous pericardium and the inner serous pericardium. The serous pericardium is divided into two layers, the parietal pericardium, which is fused to the fibrous pericardium, and the visceral pericardium (also termed epicardium). Pericardial serous fluid is found in the pericardial cavity (also termed the pericardial space) between the parietal pericardium and visceral layer.

Accessing of the pericardium may facilitate, for example, drug delivery, a pericardiocentesis procedure (aspiration of pericardial fluid typically for diagnosis of a pericardial disease), left atrial appendage removal, coronary artery bypass grafting, or placement of a reflection-facilitation element as described in US Patent Application Publication 2013/0103028 to Tsoref et al., which issued as U.S. Pat. No. 9,242,122 and which is incorporated herein by reference.

Complications may arise during surgical procedures to access the pericardium, and injury may be caused to internal organs such as the liver, stomach and lungs. Therefore, safe and efficient means of accessing the pericardium are desirable.

SUMMARY OF THE INVENTION

In accordance with some applications of the present invention, apparatus is provided for safely accessing a pericardium of a subject and penetrating the pericardium to access a pericardial region. "Pericardial region," as used in the present application, including the claims, consists of one or more regions selected from the group consisting of: a region between the pericardium and the myocardium, a region between the fibrous pericardium and the serous pericardium, a region of the pericardial cavity that is between the parietal pericardium and the visceral pericardium (also known as the epicardium).

Accessing of the pericardial region using any of the techniques described herein is useful during procedures such as a pericardiocentesis procedure in which pericardial fluid is aspirated for the purpose of diagnosing a pericardial disease, or for treatment of cardiac tamponade.

Accessing of the pericardial region using any of the techniques described herein may additionally be useful to apply pressure to bleeding myocardial tissue, typically by accessing the pericardial region and applying pressure to the site of bleeding (e.g., by placing a balloon in the pericardial region using the techniques described herein, and inflating the balloon).

The apparatus, as provided by some applications of the present invention, is shaped such as to allow a physician (e.g., an electrophysiologist) to reach the pericardium while avoiding damage to internal organs, including but not limited to, the liver, the diaphragm, the stomach and the lungs. Once the apparatus is in the vicinity of the pericardium, the apparatus contacts an outer surface of the pericardium and applies suction to the pericardium in order to draw a portion of the pericardium into the apparatus. Drawing of the portion of pericardium into the apparatus generally allows for puncturing of the pericardium by the apparatus and accessing of a pericardial region.

The apparatus comprises a longitudinal guide member, e.g., a guide tube, which is advanced distally towards a heart of the subject. The guide tube has a proximal end, a distal end and a guide-tube lumen between the proximal and distal ends. In the context of the present specification and in the claims, "proximal" means closer to the opening through which the guide is inserted into the body, and "distal" means further from this opening. The distal end of the guide tube is shaped as a blunt, typically but not necessarily dome-shaped, distal end. The blunt distal end facilitates advancement of the apparatus towards the heart by separation of tissue by blunt dissection, thereby reducing damage to internal organs. Additionally, at least part of the distal end is transparent, thus facilitating imaging of the procedure by an imaging device disposed, for example, within the guide-tube lumen.

For some applications, the apparatus further comprises a sheath which is shaped and sized to surround the guide tube and shaped to define an at least partially distally-facing suction port. When the apparatus reaches the vicinity of the heart, the sheath is brought into contact with a portion of the outer surface of the pericardium. Suction is then applied, e.g., via a suction tube in fluid communication with the inside of the sheath, to draw the portion of the pericardium into the suction port of the sheath.

The suction tube typically extends through the guide-tube lumen, and is in contact with a perimeter of a first hole in the distal end of the guide tube. The suction tube draws the portion of the pericardium into the distally-facing suction port of the sheath, by applying suction through the first hole.

The apparatus additionally comprises a needle tube which extends through the guide-tube lumen, and is in contact with a perimeter of a second hole in the distal end of the guide tube. A needle is passed through the needle tube and out of a distal end of the needle tube, in order to puncture the pericardium while the pericardium is in the sheath, gaining access to a pericardial region.

The apparatus further comprises a needle-restraining element which inhibits passage of a distal tip of the needle out of a distal end of the sheath so as to inhibit damage to cardiac tissue by the needle.

For some applications, the apparatus does not comprise a sheath, but rather the longitudinal guide member is shaped to define a suction port at a distal portion of the longitudinal guide member. For such applications, the apparatus facilitates drawing the portion of a pericardium of the heart through the suction port and into the longitudinal guide member. Typically, the suction port is shaped to define an at least partially side-facing suction port. For some applications, the suction port is shaped to define a partially distally-facing and side-facing suction port at a distal portion of the longitudinal guide member.

For such applications, the needle is passed through the longitudinal guide member and punctures the portion of the pericardium while the portion of the pericardium is in the longitudinal guide member. For some applications, the needle-restraining element is shaped and positioned with respect to the needle to inhibit passage of a distal tip of the needle-restraining element out of the distal end of the longitudinal guide member.

There is therefore provided, in accordance with some applications of the present invention, a method including:

distally advancing a longitudinal guide member toward a heart of a subject, the guide member (a) shaped to define a blunt distal end having an outer surface at least part of which is transparent, and (b) shaped to define an at least partially side-facing suction port at a distal portion of the longitudinal guide member;

during the advancing, using an imaging device disposed at least partially in the guide member to generate an image of at least part of the heart;

contacting an outer surface of a pericardium of the heart with the suction port;

subsequently, retracting the imaging device proximally in the guide member;

subsequently, drawing a portion of the pericardium into the guide member by applying suction to the pericardium through the suction port, at at least one time following the drawing of the portion of the pericardium into the guide member, generating an image of the pericardium disposed within the suction port;

subsequently, advancing a puncturing element into the guide member; and puncturing the portion of the pericardium that is in the guide member using the puncturing element.

For some applications, the method further includes subsequently to drawing the portion of the pericardium into the guide member and prior to advancing the puncturing element, removing the imaging device from the guide member, while continuing to maintain the portion of the pericardium in the guide member by applying suction through the suction port.

For some applications, using the imaging device disposed at least partially in the guide member during the advancing of the longitudinal guide member includes using the imaging device while the imaging device is disposed distally to at least part of the suction port.

For some applications, using the imaging device while the imaging device is disposed distally to at least part of the suction port includes using the imaging device while the imaging device at least partially blocks the suction port.

For some applications, the method further includes, subsequently to advancing the longitudinal guide member, rotating the longitudinal guide member such that the suction port faces the pericardium.

For some applications, the method further includes using the imaging device to generate an image of the suction port prior to the drawing of the portion of the pericardium into the guide member.

For some applications, the method further includes using the imaging device to generate an image of the suction port during the drawing of the portion of the pericardium into the guide member.

For some applications, the method further includes the puncturing element includes a needle, and using the puncturing element includes using the needle to puncture the portion of the pericardium.

For some applications, the method further includes passing a guidewire through a lumen of the needle, following the puncturing of the portion of the pericardium using the needle.

For some applications, the method further includes, prior to passing the guidewire through the lumen of the needle, rotating the needle by greater than 90 degrees such that an opening at a distal end of the needle lumen faces the myocardium tissue of the subject.

There is further provided, in accordance with some applications of the present invention, apparatus including:

a longitudinal guide member (a) including a blunt distal end having an outer surface at least part of which is transparent, (b) configured to be advanced distally toward a heart of a subject, and (c) shaped to define an at least partially side-facing suction port at a distal portion of the longitudinal guide member, the apparatus being configured to contact a pericardium of the heart to facilitate drawing a portion of the pericardium through the suction port and into the longitudinal guide member;

an imaging device disposed distally in the longitudinal guide member and configured to be retracted proximally in the longitudinal guide member subsequently to the suction port contacting the pericardium; and a puncturing element disposed proximally in the longitudinal guide member and configured to be advanced distally in the longitudinal guide member to puncture the portion of the pericardium while the portion of the pericardium is in the longitudinal guide member.

For some applications, the imaging device is disposed distally to at least part of the suction port.

For some applications, a distal portion of the longitudinal guide member is shaped to define an undivided lumen.

For some applications, the puncturing element includes a needle.

For some applications, the apparatus includes a guidewire configured to be passed through a lumen of the needle, following the puncturing of the portion of the pericardium using the needle.

There is further provided, in accordance with some applications of the present invention, a apparatus including:

a longitudinal guide member (a) including a blunt distal end having an outer surface at least part of which is transparent, (b) configured to be advanced distally toward a heart of a subject, and (c) shaped to define a suction port at a distal portion of the longitudinal guide member, the apparatus being configured to facilitate drawing a portion of a pericardium of the heart through the suction port and into the longitudinal guide member;

an imaging device disposed in the longitudinal guide member;

at least one light baffle (a) positioned to face the distal end of the longitudinal guide member and (b) being aligned generally perpendicular with a center of the imaging device; and a puncturing element configured to puncture the portion of the pericardium while the portion of the pericardium is in the longitudinal guide member.

The present invention will be more fully understood from the following detailed description of embodiments thereof, taken together with the drawings, in which:

BRIEF DESCRIPTION OF THE DRAWINGS

FIGS. 2A, 2B, 2C, 2D, and 2E are schematic illustrations of respective apparatus for penetrating a pericardium, in accordance with some applications of the present invention;

FIGS. 3A and 3B are schematic illustrations of longitudinal cross-sections of apparatus for penetrating a pericardium, in accordance with some applications of the present invention;

FIGS. 4A, 4B and 4C are schematic illustrations of longitudinal cross-sections of apparatus for penetrating a pericardium, further showing a puncturing-element-restraining element, in accordance with some applications of the present invention;

FIGS. 5A, 5B, 5C, 5D, and 5E show use of apparatus for penetrating a pericardium, in accordance with some applications of the present invention;

FIG. 6 is a schematic illustration of an inflatable element for use with apparatus for penetrating a pericardium, in accordance with some applications of the present invention;

FIGS. 7A, 7B, 8A and 8B are schematic illustrations of a curved needle for use with applications of the present invention;

FIG. 9 is a schematic illustration of apparatus that creates a working space between two layers of tissue, in accordance with some applications of the present invention;

FIG. 10 is a schematic illustration of an asymmetric distal end of a longitudinal guide member, in accordance with some applications of the present invention;

FIG. 11 is a schematic illustration of apparatus that creates a working space between two layers of tissue, in accordance with some applications of the present invention;

FIGS. 12A, 12B, 12C, 12D, 12E, 12F, and 12G show respective designs of an expandable element, in accordance with some applications of the present invention;

FIGS. 15A, 15B, 15C and 15D are schematic illustrations of apparatus for penetrating a pericardium, in accordance with some applications of the present invention;

FIGS. 17A and 17B are schematic illustrations of apparatus for penetrating a pericardium, in accordance with some applications of the present invention;

FIGS. 18A 18B, 19A, 19B, 20A, 20B, 21A, 21B, 22A, 22B and 22C are schematic illustrations of various configurations of the apparatus for penetrating a pericardium, in accordance with some applications of the present invention;

FIGS. 23A, 23B, and 23C are schematic illustrations of a light reflector for use with apparatus for penetrating a pericardium, in accordance with some applications of the present invention; and FIGS. 24A, 24B, 24C, 24D, 24E, 24F, 24G, 24H, 24I and 24J are schematic illustrations of apparatus for penetrating a pericardium, in accordance with some applications of the present invention.

DETAILED DESCRIPTION OF APPLICATIONS

The present description begins with a general overview of a method for accessing a pericardial region, in accordance with some applications of the present invention, as depicted in FIGS. 5A-E.

Figure 5A:
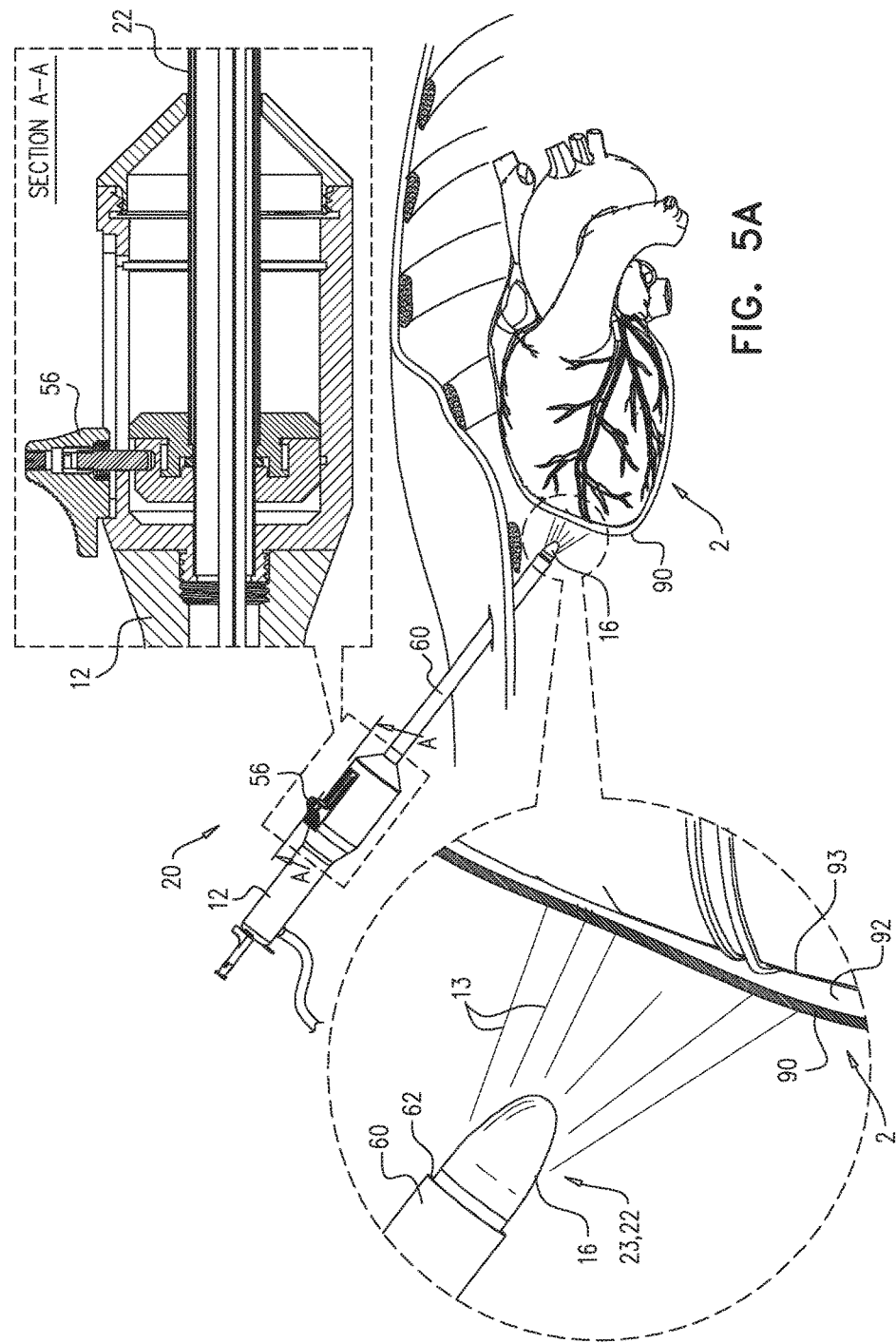
Figure 5B:
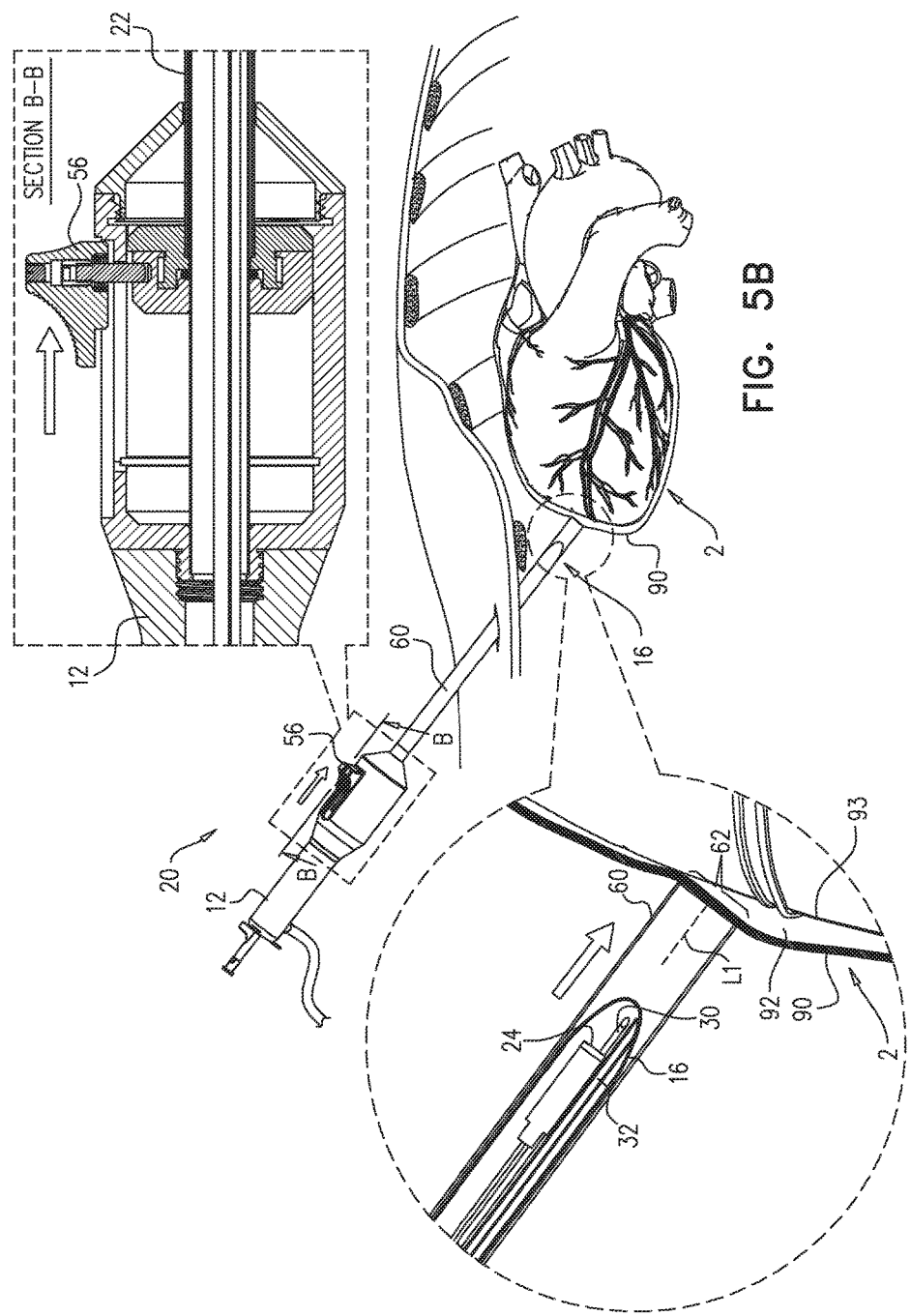

FIGS. 5A-E show use of apparatus 20 for penetrating a pericardium 90 of a subject, and accessing a pericardial region 92. FIG. 5A shows a longitudinal guide member 23, e.g., a guide tube 22, of apparatus 20 being distally advanced toward a heart 2 of the subject, a distal end 16 of guide tube 22 emerging from a distal suction port 62 of sheath 60. Advancement of guide tube 22 may be facilitated by an imaging device 24 (FIG. 5B). Typically, at least one illumination-providing element 26 (FIG. 2A) provides illumination for imaging device 24, the illumination being depicted in FIG. 5A by light rays 13.

Figure 5C:
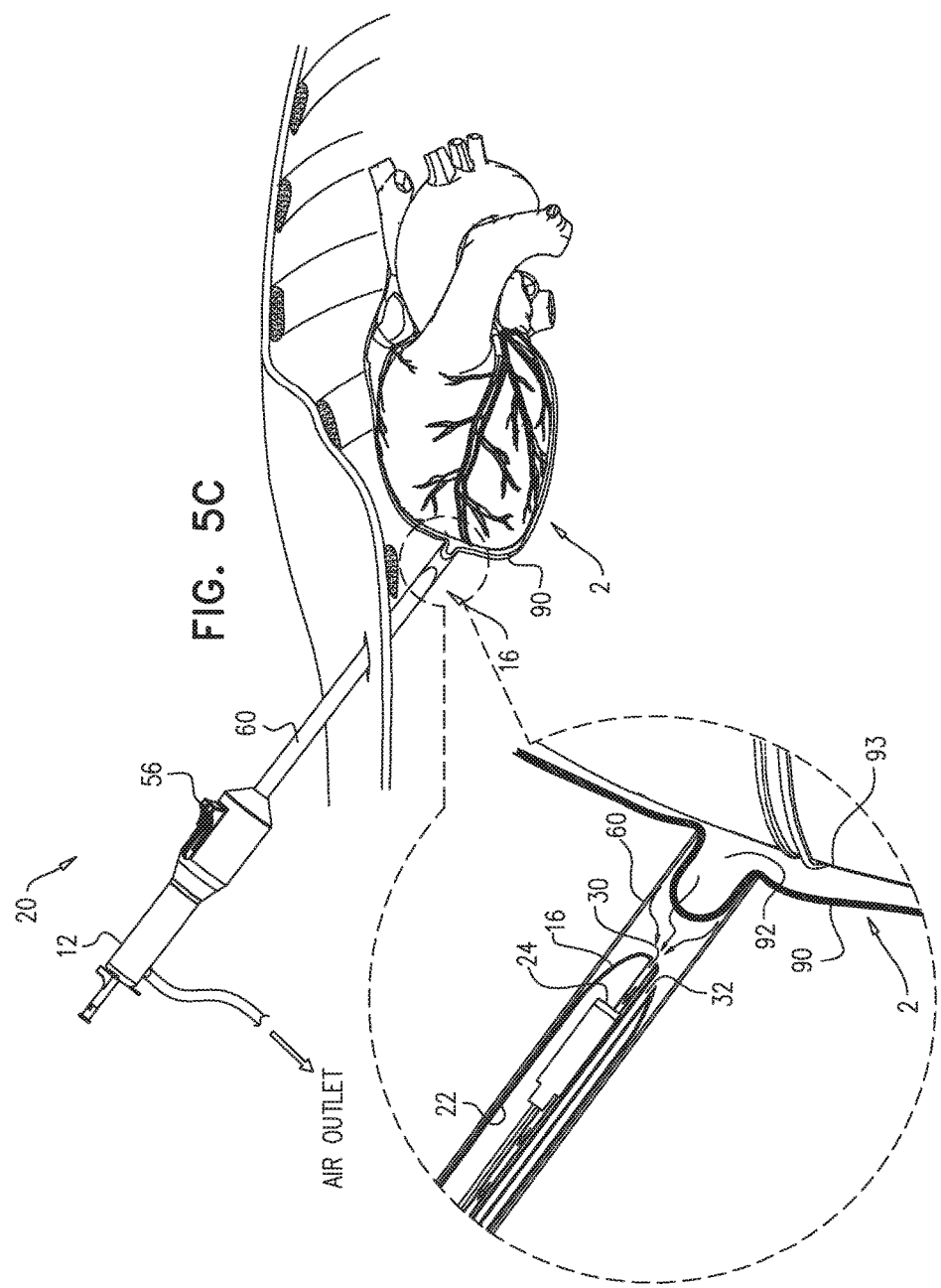

When guide tube 22 reaches the heart, the operating physician deploys sheath 60 over the guide tube, e.g., by sliding a slide bar 56 distally, and a perimeter of suction port 62 contacts an outer surface of pericardium 90 (FIG. 5B). Suction is then applied to the pericardium through suction port 62, e.g., via a suction tube 30, and a portion of pericardium 90 is drawn into the sheath, as shown in FIG. 5C. (Suction may be applied using a hospital suction generator, and/or an external vacuum pump, and/or a syringe.) For some applications, pericardial tissue is drawn at least 4 mm into sheath 60, e.g., at least 1 cm or at least 1.5 cm into sheath 60.

After the portion of pericardium 90 is drawn into sheath 60, a puncturing element 50 (e.g., a needle 51) is advanced distally to puncture the portion of the pericardium, as shown in FIG. 5D. The puncturing of the portion of the pericardium provides access to pericardial region 92, e.g., a region between pericardium 90 and myocardial tissue 93. Optionally, grasping elements, such as forceps and/or other types of grasping elements (e.g., corkscrew-like or screw-shaped grasping elements), may be employed to grip the portion of pericardium that is inside the sheath, to facilitate the puncturing.

For some applications, following the puncturing of pericardium 90, a guidewire 70 is advanced through a lumen of needle 51 and into pericardial region 92 (FIG. 5E). Typically, the needle is then withdrawn, and a tool is passed over the guidewire, as further described hereinbelow. Alternatively or additionally, needle 51 delivers a fluid, e.g., a gas for inflation of the pericardium, and/or a contrast medium, to the pericardial region.

Figure 1:
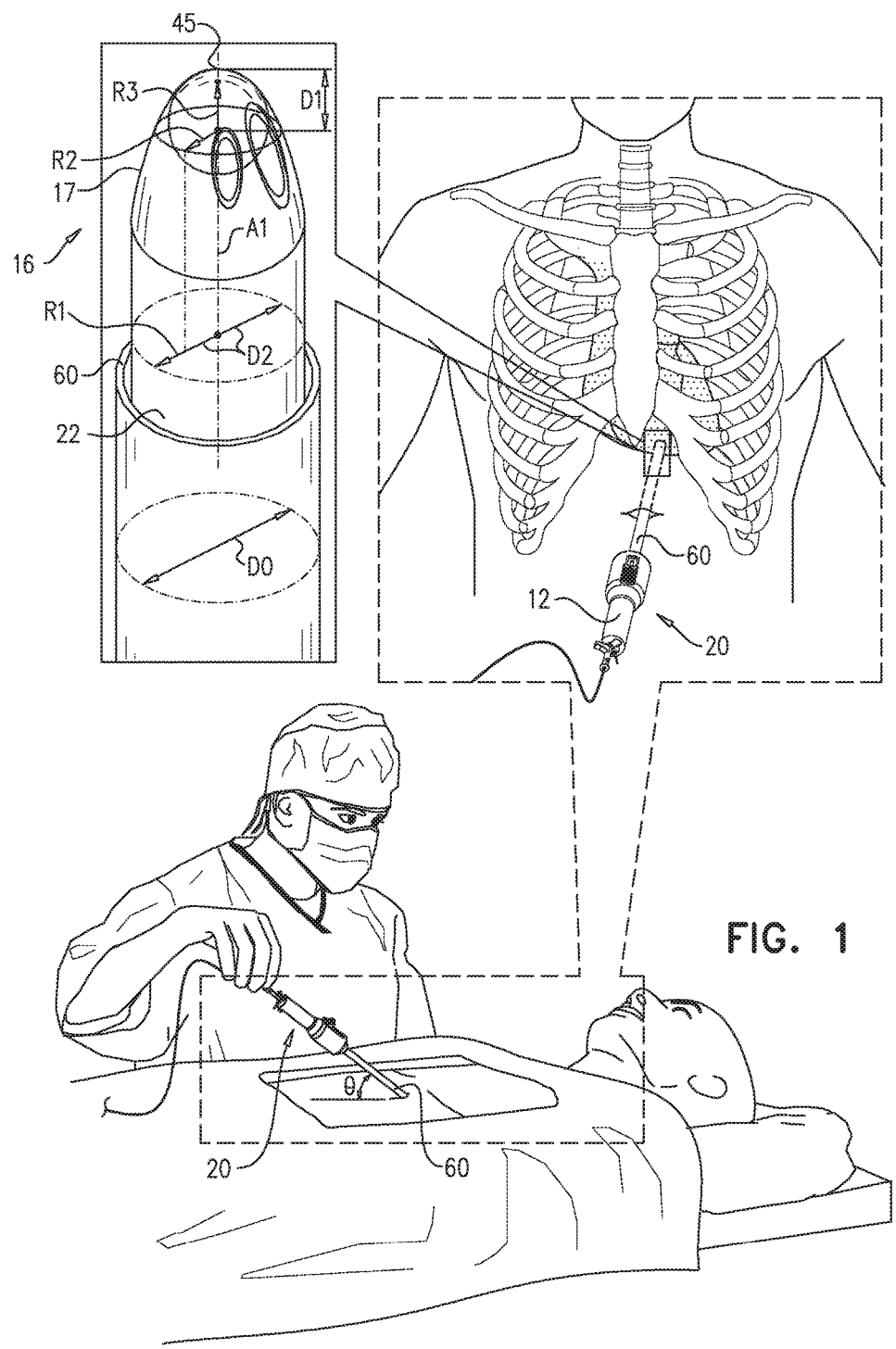
FIG. 1 is a schematic illustration of apparatus for penetrating a pericardium, in accordance with some applications of the present invention.

Reference is now made to FIG. 1, which is a schematic illustration of apparatus 20, as provided in accordance with some application of the present invention. Apparatus 20 is inserted into the subject, and is advanced distally toward the heart of the subject. It is noted that apparatus 20 may be advanced towards the heart through any suitable pathway. For example, apparatus 20 may be advanced through the subxiphoid incision, above the diaphragm, directly to the heart.

Apparatus 20 is generally shaped to provide safe and efficient access to the heart. For example, distal end 16 of guide tube 22, as shown in FIG. 1, is typically blunt, the bluntness of the distal end generally facilitating blunt dissection of tissue (i.e., generally atraumatic separation of adjacent tissues) during advancement toward the heart, and generally reducing the chances of injury to internal organs such as the diaphragm, the lungs, the stomach and the liver. Typically, blunt distal end 16 is sufficient in size to allow blunt dissection. In some applications, as shown in FIG. 1, at least part of an outer surface 17 of distal end 16 is dome-shaped. A radius of curvature R3 at the distalmost point 45 of distal end 16 is typically at least 0.5 mm and/or less than 5 mm. R3 is typically less than the radius R1 of guide tube 22, and is further typically at least 30% and/or less than 60% (e.g., between 30% and 60%, e.g., 50%), of R1. Alternatively or additionally, a radius R2 of distal end 16, measured at a distance D1 of 3 mm from distalmost point 45, is at least 1 mm and/or less than 2 mm.

FIG. 1 also shows sheath 60, which is sized and shaped to surround the guide tube. Typically, a diameter D0 of sheath 60 is at least 6 mm and/or less than 15 mm.

Reference is now made to FIG. 2A, which is a schematic illustration of apparatus 20, in accordance with some applications of the present invention. Reference is also made to FIGS. 3A-B, which are longitudinal cross-sections of apparatus 20, in accordance with some applications of the present invention.

In addition to having distal end 16, guide tube 22 has a proximal end 14, and is shaped to define a guide-tube lumen 18 between proximal end 14 and distal end 16. A diameter D2 (FIG. 1) of guide-tube lumen 18 is typically greater than 4 mm and/or less than 15 mm.

Typically, at least part of outer surface 17 of distal end 16 is transparent. Typically, apparatus 20 comprises an imaging device 24, e.g., a camera, disposed at least partially at distal end 16, and the transparency of distal end 16 facilitates the use of imaging device 24. In some applications, the imaging device comprises an imaging sensor that is disposed within the guide tube (e.g., within guide-tube lumen 18 and/or distal end 16). Alternatively or additionally, imaging device 24 comprises a fiber optic array having a distal end that is disposed within the guide tube, and an imaging sensor coupled to a proximal end of the fiber optic array (application not shown). For some applications, at least part of imaging device 24 is disposed within 15 mm of distalmost point 45 of distal end 16.

Typically, at least one illumination-providing element 26 is disposed at least partially within the guide tube and is configured to provide visible and/or infrared illumination for operation of the imaging device. (For example, four illumination-providing elements may be disposed in the guide tube, as shown in FIG. 2A.) In some applications, illumination-providing element 26 comprises a light source (e.g., a light emitting diode (LED)) disposed within the guide tube. Alternatively or additionally, the illumination-providing element comprises an optical fiber having a distal end that is disposed within the guide tube, and a light source coupled to a proximal end of the optical fiber (application not shown).

Apparatus 20 is typically configured such that most of the light that is emitted from the illumination-providing element is not directly reflected to the imaging device by distal end 16, as such reflection might cause the imaging device to be at least partially "blinded". Typically, at least 80% of light that is emitted from the at least one illumination-providing element and reflected by distal end 16 is not directly reflected to the imaging device. In some applications, this property of apparatus 20 is at least partially due to a disposition of the at least one illumination-providing element with respect to the imaging device. Alternatively or additionally, a shape of the distal end 16, and/or an optical parameter of distal end 16 and/or of coating applied internally or externally to distal end 16, may facilitate the relatively small amount of blinding reflection. Alternatively or additionally, the relatively small amount of blinding reflection may be facilitated by one or more polarizing filters (not shown) that at least partially cover the at least one illumination-providing element, and/or the imaging device, and/or an inner surface of distal end 16.

Reference is now additionally made to FIG. 10, which is a schematic illustration of an asymmetric distal end 16a of longitudinal guide member 23 (e.g., guide tube 22), in accordance with some applications of the present invention. As noted above, in some applications, the shape of distal end 16 may facilitate the relatively small amount of blinding reflection. For example, distal end 16a may be rotationally asymmetric with respect to a local central longitudinal axis A3 of the guide tube, such that, for example, at at least one site within 1 mm of distalmost point 45 of distal end 16a, and/or at all sites within 3 mm of the distalmost point of the distal end, a centroid 49 of a cross-section of the distal end does not lie on axis A3. (In FIG. 10, the distances L4 and L5 are equal, i.e., the marked point is indeed centroid 49.)

Returning to FIG. 2A, in some applications, the illumination is changed dynamically, depending on a level of glare that is ascertained in the image. (The level of glare in the image corresponds to the amount of blinding reflection referred to above.) For example, illumination-providing element 26 may be moved (e.g., along a track 27) in response to an ascertained level of glare, in order to potentially reduce the glare. Alternatively or additionally, in applications in which at least two (i.e., first and second) illumination-providing elements are used, one illumination-providing element may be turned off, and another turned on, in response to the ascertained level of glare, in order to potentially reduce the glare. In other words, in response to the level of glare, exactly one illumination-providing element is selected from the first illumination-providing element and the second illumination-providing element, and illumination is provided from the selected illumination-providing element. For example, in response to the level of glare, first LED 26a may be lit, while second LED 26b is not lit. Typically, the glare-reduction techniques described herein are performed automatically by a processor.

The imaging sensor belonging to imaging device 24, described hereinabove, may be considered to be a heart-proximity sensor, in that the imaging performed by imaging device 24 helps the operator ascertain that distal end 16 is proximate to the heart; typically, imaging device 24 is used to generate an image of at least part of the heart of the subject, and the proximity is ascertained, using the image. Alternatively or additionally to imaging device 24, apparatus 20 comprises one or more other types of heart-proximity sensor 29 configured to generate a signal indicative of a proximity of the distal end of the guide tube to the heart of the subject. Before deploying the suction port of the sheath over the guide tube, heart-proximity sensor 29 is used to generate the signal, and the proximity is ascertained, using the signal. As shown in FIG. 2A, heart-proximity sensor 29 is typically coupled to distal end 16, e.g., to outer surface 17 of distal end 16.

Figure 14A:
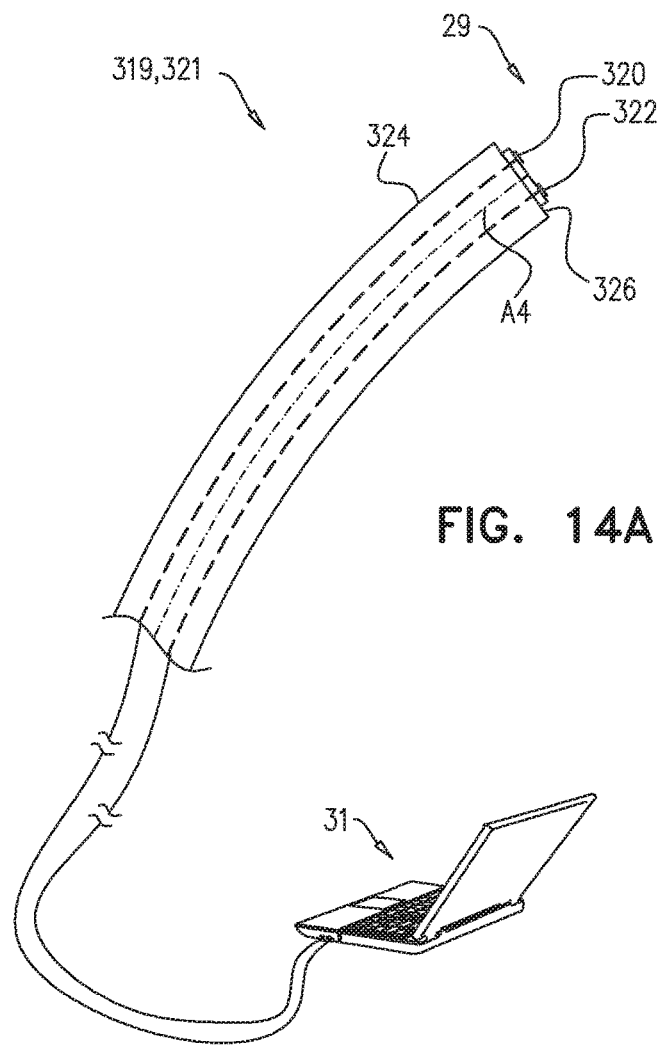
FIG. 14A is a schematic illustration of proximity-sensing apparatus, in accordance with some applications of the present invention.

In some applications, heart-proximity sensor 29 comprises an ultrasound (e.g., a Doppler ultrasound) sensor (e.g., transducer). In response to a signal (e.g., an ultrasound image) received by the ultrasound sensor, the operator may ascertain that distal end 16 is proximal to the heart. (The ultrasound transducer may also be used for treatment.) Alternatively or additionally, the heart-proximity sensor comprises a contact sensor configured to generate a signal indicative of contact of the blunt distal end of the guide tube to the heart of the subject. Alternatively or additionally, the heart-proximity sensor comprises an accelerometer. Typically, for applications in which an accelerometer is used, apparatus 20 further comprises a processor 31 configured to generate an output indicative of the proximity of the blunt distal end of the guide tube to the heart of the subject, based on a signal received from the accelerometer, as further described immediately hereinbelow with reference to FIGS. 14A-C.

While advancing guide tube 22 toward the heart of the subject, care must be taken not to damage (e.g., puncture) internal organs, such as the liver, of the subject. In some applications, the heart-proximity sensor comprises both an accelerometer and a contact sensor, which together help prevent such damage from occurring, as further described immediately hereinbelow with reference to FIGS. 14A-C.

The scope of the present invention includes use of certain proximity-sensing apparatus and methods, even outside of the context of pericardium penetration. In this regard, reference is now additionally made to FIG. 14A, which is a schematic illustration of proximity-sensing apparatus 319 and 321, and to FIGS. 14B-C, which are flow charts of proximity-sensing methods 323 and 325, in accordance with some applications of the present invention. The description below of these figures is also applicable to apparatus 20, mutatis mutandis.

Figure 14B:
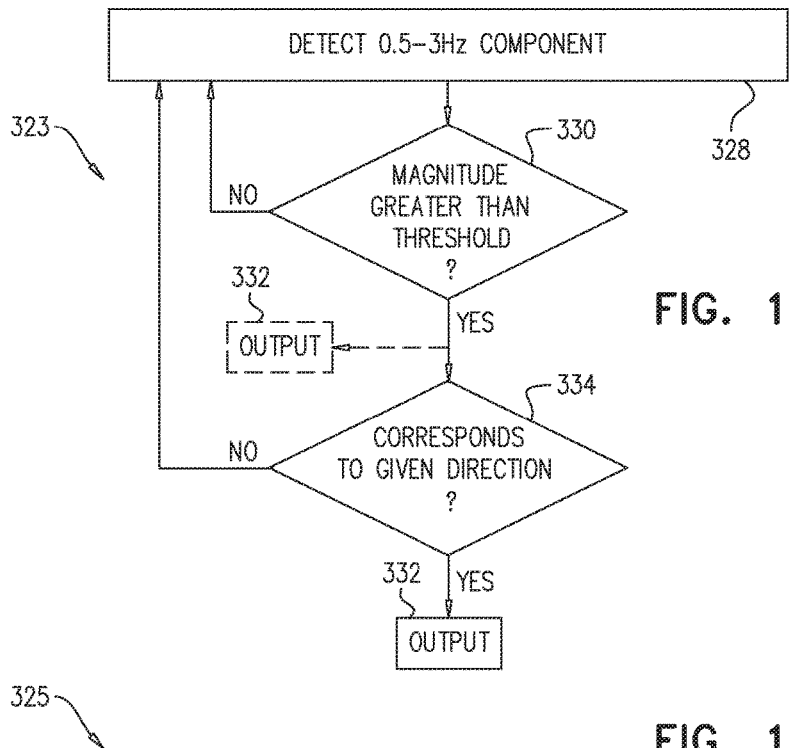
FIGS. 14B and 14C are flow charts of proximity-sensing methods, in accordance with some applications of the present invention.

FIG. 14 shows apparatus 321, in which processor 31 is configured to generate an output indicative of the proximity of the distal portion 326 of a catheter 324 to the heart of the subject. Proximity-sensing method 323, performed in combination with apparatus 321 (and, as noted above, apparatus 20), is depicted in FIG. 14B. Apparatus 321 comprises an accelerometer 320, which generates a signal upon being accelerated. In a detection step 328, processor 31 detects a component of the signal having a frequency between 0.5 and 3 Hz, which generally encompasses the typical range of heartbeat frequencies. In a magnitude-comparison step 330, the magnitude of this component is compared to a threshold. If the magnitude is greater than the threshold, the processor may generate the output in output step 332. (This step is indicated by the dashed arrow and box in FIG. 14B.) The output may include audio and/or visual output to the operator of the apparatus, indicating proximity to the heart.

In some applications, directional accelerometry is used, and the processor is configured to generate the output only if (per a direction-comparison step 334) the detected component of the signal corresponds to a direction that is generally perpendicular to a local central longitudinal axis A4 of the catheter. In the context of apparatus 20, the processor generates the output only if the detected component of the signal corresponds to a direction that is generally perpendicular to a plane 33 (FIG. 3C) defined by suction port 62 of the sheath, and/or is generally parallel to a central longitudinal axis of the guide tube at the distal end of the guide tube (cf. A3 in FIG. 10); thus, the operator receives confirmation that apparatus 20 is aligned properly with respect to the heart.

Figure 14C:
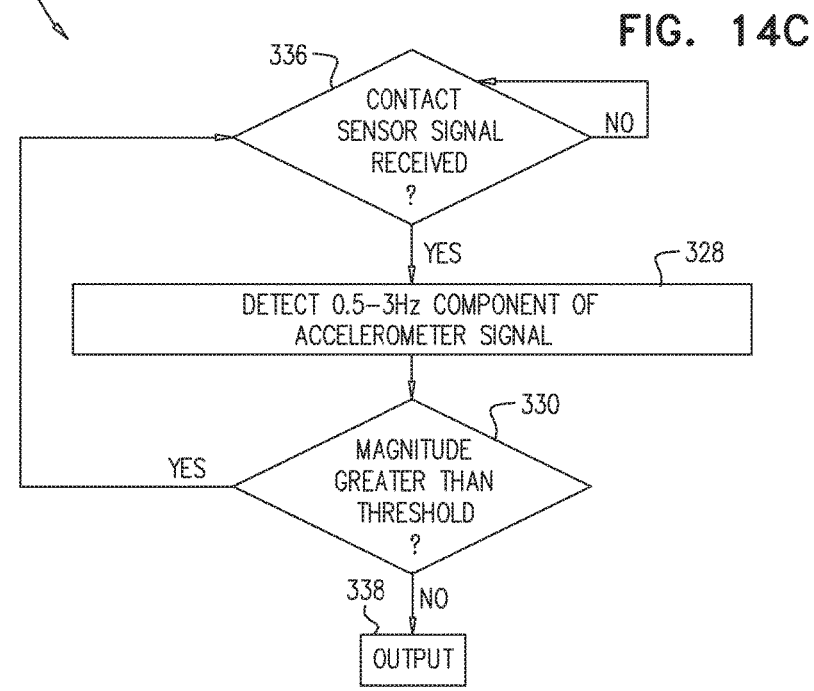

FIG. 14 also shows apparatus 319 comprising a heart-proximity sensor 29 disposed at distal portion 326 of catheter 324. Heart-proximity sensor 29 comprises accelerometer 320 and a contact sensor 322, which work together to generate a signal indicative of a proximity of distal portion 326 to an internal organ of a subject that is not the heart of the subject. (In other words, the signals from contact sensor 322 and accelerometer 320 together make up a signal that is indicative of contact with the internal organ that is not the heart.) As noted above, this signal may help prevent damage to the internal organ. Proximity-sensing method 325, depicted in FIG. 14C, is practiced in combination with apparatus 319, and, as noted above, with apparatus 20.

If contact sensor 322 contacts the organ, the contact sensor generates a signal that is indicative of this contact. The signal from the contact sensor is received, e.g., by processor 31, in a contact-signal-receiving step 336. Then, detection step 328, as described above with reference to FIG. 14B, is executed, e.g., by processor 31. If, per magnitude-comparison step 330, the magnitude of the detected 0.5-3 Hz component exceeds the threshold, it is likely that contact has been made with the heart, and thus, no output is generated. If, on the other hand, the magnitude does not exceed the threshold, it is likely that contact has been made with an internal organ that is not the heart. In response, processor 31 may generate an output, in an output step 338. The output may take the form of an audio and/or visual warning to the operator to change the advancement trajectory.

Apparatus 319 and 321 may be combined into a single apparatus, and methods 323 and 325 may be practiced in combination with each other. For example, method 325 may include direction-comparison step 334 of method 323, prior to output step 338.

Returning to FIG. 2A, apparatus 20 further comprises a puncturing element 50, e.g., a needle 51 shaped to define a lumen thereof. As described hereinabove with reference to FIGS. 5A-E, puncturing element 50 is configured to puncture a portion of the pericardium while the portion of the pericardium is in sheath 60. In some applications, apparatus 20 further comprises a puncturing-element tube 32, and puncturing element 50 is sized and shaped to be passable through puncturing-element tube 32 and out of a distal end of the puncturing-element tube. In some applications, as shown in FIG. 2A, distal end 16 (e.g., outer surface 17) is shaped to define a puncturing-element-tube hole 44 therein, and puncturing-element tube 32 is disposed within the guide tube (e.g., within lumen 18) such that the puncturing-element tube is in contact with a perimeter 38 of puncturing-element-tube hole 44. For example, a distalmost perimeter of puncturing-element tube 32 may contact perimeter 38. Typically, a diameter of puncturing-element-tube hole 44 is at least 0.2 mm and/or less than 2 mm; alternatively, the diameter is at least 2 mm and/or less than 5 mm. (In the context of the present description and claims, the term "diameter," when applied to an ellipse, refers to a mean of the lengths of the major and minor axes. Puncturing-element-tube hole 44 is elliptically shaped in FIG. 2A, such that the diameter of the hole is the mean of lengths L2 and L3.)

Figure 3C:
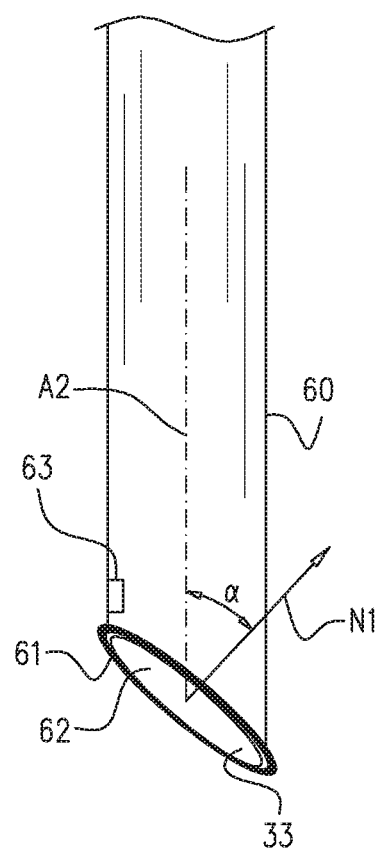
FIG. 3C is a schematic illustration of a sheath and suction port, in accordance with some applications of the present invention.
Figure 3D:
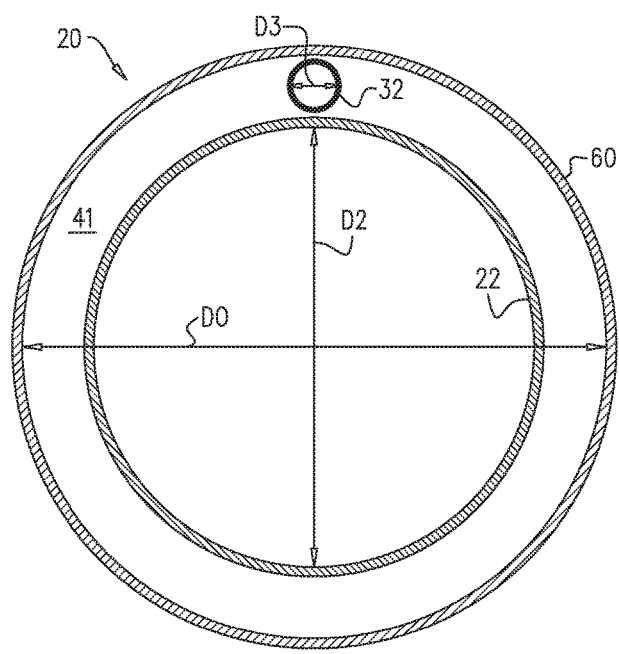
FIG. 3D is a schematic illustration of a cross-section of apparatus for penetrating a pericardium, in accordance with some applications of the present invention.

Reference is now additionally made to FIG. 3D, which is a cross-section of apparatus 20, in accordance with some applications of the present invention. In some applications, puncturing-element tube 32 is disposed between sheath 60 and guide tube 22, instead of within the guide tube. In some applications, puncturing element 50 is not disposed inside of puncturing-element tube 32, but rather, is disposed directly inside of guide-tube lumen 18 or between guide member 23 (e.g., guide tube 22) and sheath 60.

Figure 3E:
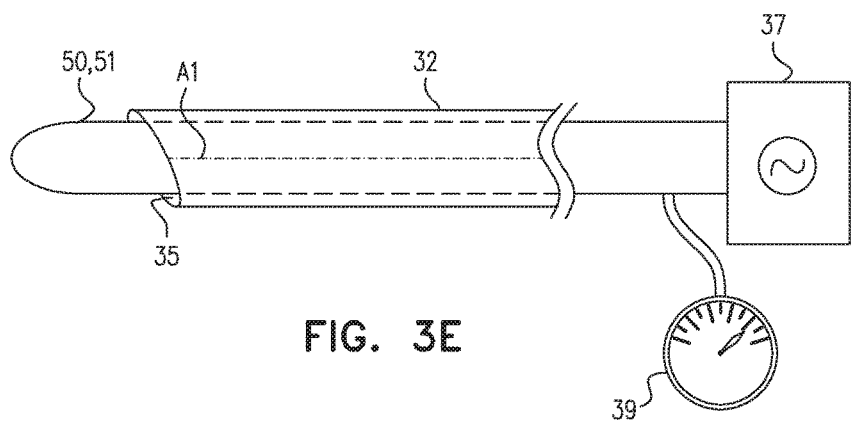
FIG. 3E is a schematic illustration of a puncturing-element tube, in accordance with some applications of the present invention.

Reference is now additionally made to FIG. 3E, which is a schematic illustration of puncturing-element tube 32, in accordance with some applications of the present invention. In some applications, a distal end of puncturing-element tube 32 defines a face 35 that is not perpendicular to a local central longitudinal axis A1 of puncturing-element tube 32. (In the context of the present description and claims, the "central longitudinal axis" of a structure refers to the set of centroids of all cross-sections of the structure. The central longitudinal axis may curve, such that the orientation of the central longitudinal axis varies across its length; the "local" central longitudinal axis refers to the tangent to the central longitudinal axis at or generally near the point of interest.)

As further shown in FIG. 3E, in some applications, puncturing element 50 comprises a radiofrequency wire and/or a radiofrequency needle 51, and apparatus 20 further comprises a radiofrequency generator 37 configured to transmit a radiofrequency signal to a distal end of the radiofrequency wire and/or needle. The radiofrequency signal facilitates the puncture of the pericardium.

In some applications, apparatus 20 further comprises a sensor 39 configured to measure an electrophysiological signal occurring at a tip of puncturing element 50. For example, a voltmeter coupled to a proximal end of the puncturing element may measure a voltage occurring at the tip of the puncturing element. Since the voltage within the pericardium is different from the voltage outside of the pericardium, sensor 39 may help the operator ascertain that the pericardium has been punctured.

As described hereinabove with reference to FIGS. 5A-E, apparatus 20 is configured to facilitate drawing a portion of a pericardium of the heart through suction port 62 of sheath 60 and into the sheath, by the application of suction. In some applications, puncturing-element tube 32 is a puncturing-element-and-suction tube, i.e., suction may be applied through the puncturing-element tube, in order to draw in the portion of the pericardium. Alternatively or additionally, as shown in FIG. 2A, apparatus 20 comprises a separate suction tube 30, configured to facilitate the drawing in of the portion of the pericardium by the application of suction through suction tube 30.

In some applications, as shown in FIG. 2A, distal end 16 is shaped to define a suction-tube hole 42 therein, and the suction tube is disposed within the guide tube (e.g., within lumen 18) such that a distal end of the suction tube is in contact with a perimeter 36 of the suction-tube hole. Suction tube 30 facilitates the application of suction through suction-tube hole 42 to draw the portion of the pericardium into sheath 60. A diameter of suction-tube hole 42 is typically at least 0.2 mm, e.g., at least 0.5 mm, and/or less than 2 mm; alternatively, the diameter is at least 2 mm and/or less than 5 mm. (A "diameter" of an ellipse is defined above.) In other applications, suction tube 30 is disposed between the guide tube and the sheath, as shown in FIG. 3D for the puncturing-element tube.

For some applications, a distal end of suction tube 30 defines a face that is not perpendicular to a local central longitudinal axis of suction tube 30, as shown in FIG. 3D for puncturing-element tube 32.

In some applications, suction is applied through a space 41 (FIG. 3D) between an outer wall of guide tube 22 and an inner wall of sheath 60, alternatively or additionally to the application of suction through suction tube 30. In such applications, space 41 is typically large enough to facilitate the application of suction, but not so large as to have an unduly-large diameter of the sheath. For example, diameter D0 of sheath 60 may be greater than 0.1 mm (e.g., greater than 0.2 mm) and/or less than 4 mm (e.g., less than 0.6 mm) greater than a diameter D2 of the guide tube.

In some applications, an oscillating suction pressure is applied, such as to facilitate separation of the portion of the pericardium from the tissue (e.g., myocardial tissue) that is underneath it. Alternatively or additionally, to facilitate this separation, a suction pressure that increases at an average rate of at least 5 and/or less than 15 mm Hg per second is applied for at least 1 second. In some applications, apparatus 20 comprises a vibrating element 47 configured to vibrate the distal end of the guide tube during and after the drawing of the portion of the pericardium into sheath 60. This vibration may help separate the portion of the pericardium from the portion of the myocardium that is underneath it.

In some applications, rinsing fluid may be passed through puncturing-element tube 32 and puncturing-element-tube hole 44, and/or through suction tube 30 and suction-tube hole 42, in order to remove debris from an external surface of distal end 16. In some applications, the rinsing fluid is passed through a separate rinsing-fluid lumen in guide tube 22 (not shown), and/or through a separate hole in distal end 16 (not shown).

In some applications, the advancement of apparatus 20 is facilitated by the use of electrophysiological sensing. For example, electrodes may be attached to apparatus 20 (e.g., to distal end 16 and/or puncturing element 50), the electrodes electrically coupled to an extracorporeal monitor. The electrodes facilitate navigation of apparatus 20 by detecting electrical activity of the heart (e.g., ECG signals). Alternatively or additionally, such electrodes may be radiopaque, and may facilitate navigation of apparatus 20 toward the heart by use of fluoroscopic imaging techniques.

Other navigation techniques include use of a 3D (i.e., position only) or 6D (i.e., position and orientation) navigation system in order to facilitate safe and efficient access to the heart. In some applications, a position sensor 43 disposed at a distal portion of the guide tube (e.g., coupled to distal end 16) is used to measure a position of distal end 16, and a proximity of the distal end of the guide tube to the heart of the subject is ascertained, using the measured position. In some applications, sensor 43 is a position-and-orientation sensor, and the position and orientation measured by sensor 43 are used to navigate the guide member. Alternatively or additionally, sensor 43 comprises an ultrasound sensor (e.g., a Doppler ultrasound sensor), and the image from the ultrasound sensor is used to navigate the guide tube. In some applications, sensor 43 is integrated with a CARTO™ or NavX™ navigation system.

For some applications, a preoperative image (e.g., a preoperative CT image) of the subject is used for navigation. The preoperative image may be used in combination with the 3D or 6D navigation system described above, and/or in combination with realtime images from imaging device 24, e.g., via use of image registration techniques.

Typically, a handle 12, shown in FIG. 2A, facilitates the advancement and operation of apparatus 20.

Figure 2B:
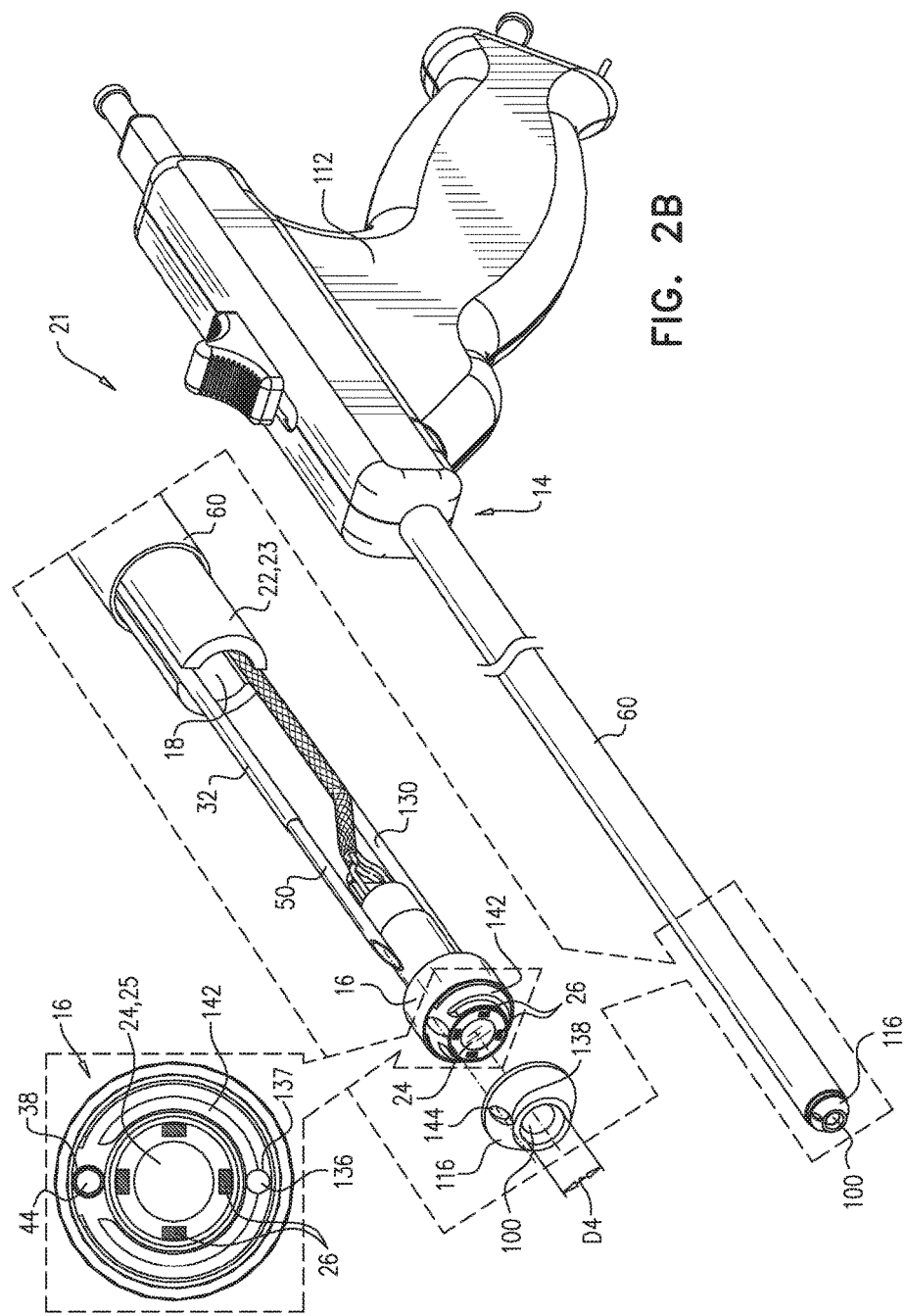

Reference is now made to FIG. 2B, which is a schematic illustration of apparatus 21 for penetrating the pericardium, in accordance with some applications of the present invention. Apparatus 21 is generally similar to apparatus 20. A notable difference, however, is that distal end 16 of guide member 23 is not closed, as further described hereinbelow.

Apparatus 21 comprises guide member 23 (e.g., guide tube 22). As in apparatus 20, guide tube 22 has a proximal end 14 and a distal end 16, and is shaped to define a guide-tube lumen 18 between the proximal and distal ends. A distal-end cover 116 is shaped to (i) define an aperture 100 therein, and (ii) cover distal end 16 of the guide tube. Distal-end cover 116 is typically shaped such as to facilitate blunt dissection and safe navigation and advancement of apparatus 21 toward the heart, as described hereinabove with respect to distal end 16 of apparatus 20. Aperture 100 typically has a diameter D4 of at least 1 mm and/or less than 5 mm. In some respects, the function of distal-end cover 116 of apparatus 21 is analogous to that of distal end 16 of apparatus 20. For example, heart proximity sensor(s) 29 (FIG. 2A) may be coupled to distal-end cover 116, and may be used to help ascertain proximity to and/or contact with the heart or another internal organ, as described hereinabove.

Imaging device 24 is typically disposed at distal end 16 of guide tube 22. Apparatus 21 may further comprise one or more, e.g., four, illumination-providing elements 26, e.g., LEDs, as describe hereinabove with reference to apparatus 20. In some applications, distal-end cover 116 is transparent. In other applications, distal-end cover 116 is not transparent; in such applications, imaging device 24 is typically aligned with aperture 100, and illumination-providing elements 26 are typically disposed such that illumination may pass through aperture 100. (Typically, apparatus 21 is configured to reduce blinding reflections, as described hereinabove with respect to apparatus 20.)

As in apparatus 20, puncturing element 50 is disposed within guide-tube lumen 18, or between guide member 23 (e.g., guide tube 22) and sheath 60. In some applications, puncturing element 50 is disposed within puncturing-element tube 32, as in apparatus 20. FIG. 2B shows an application in which puncturing-element tube 32 extends through lumen 18 and contacts perimeter 38 of puncturing-element-tube hole 44 in distal end 16. In such applications, distal-end cover 116 is typically shaped to define a second puncturing-element-tube hole 144 in alignment with hole 44, for passage therethrough of puncturing element 50. In some applications, apparatus 21 includes a handle 112, which facilitates the advancement and operation of the apparatus.

The lens 25 of imaging device 24 might become obstructed by debris that enters aperture 100. Hence, in some applications, apparatus 21 includes elements that facilitate cleaning of the lens. For example, distal end 16 may be shaped to define a rinse port 136 therein, rinse port 136 typically being close to lens 25 of imaging device 24. In such applications, apparatus 21 further comprises a rinse tube 130 in fluid communication with the rinse port, e.g., in contact with a perimeter 137 of rinse port 136. Rinse fluid may be passed through rinse tube 130 and through port 136 to remove the debris, thus facilitating the imaging functionality of imaging device 24. In some applications, distal end 16 is further shaped to define a groove 142, which facilitates the flow of the rinse fluid over the lens of the imaging device.

In some applications, rinse tube 130 is a rinse-and-suction tube, i.e., it also functions as a suction tube, for facilitating drawing the portion of the pericardium into the sheath. In other applications, apparatus 21 comprises a separate suction tube, e.g., as described hereinabove with respect to apparatus 20.

In general, the description herein relating to the operation of apparatus 20, e.g., with respect to the drawing of the sheath over the guide tube, puncturing of the pericardium, etc. also relates to apparatus 21, mutatis mutandis.

Reference is now made to FIG. 2C, which is a schematic illustration of apparatus 21' for penetrating the pericardium, in accordance with some applications of the present invention. Apparatus 21' differs from apparatus 21, in that guide member 23 is a shaft 55 shaped to define one or more longitudinal channels 57 therealong, instead of guide member 23 being guide tube 22. (In order to show shaft 55, sheath 60 is hidden from view in FIG. 2C.) Shaft 55 may also be used instead of guide tube 22 in apparatus 20, yielding alternate apparatus 20'. In general, apparatus 20' is functionally equivalent to apparatus 20, and apparatus 21' is functionally equivalent to apparatus 21. Generally, longitudinal channel(s) 57 take the place of guide-tube lumen 18. For example, puncturing element 50, puncturing-element tube 32, rinse tube 130, etc. may all be disposed within one or more longitudinal channels in shaft 55. The entire description herein of apparatus 20 and apparatus 21 is intended to also relate to apparatus 20' and apparatus 21', even when guide tube 22 is specifically mentioned. (Distal-end cover 116 is not shown in FIG. 2C.)

Reference is now made to FIGS. 2D-E, which are schematic illustrations of apparatus 300 for penetrating a pericardium, in accordance with some applications of the present invention. Apparatus 300 comprises longitudinal guide member 23, i.e., guide tube 22 or shaft 55, comprising a distal end 302. Distal end 302 differs from distal ends 16 and 16a described hereinabove with reference to apparatus 20 and 21, respectively, as further described hereinbelow. Another difference between apparatus 300 and apparatus 20/21 is that apparatus 300 does not necessarily include sheath 60, as further described hereinbelow. (In most other respects, apparatus 300 is generally similar or identical to apparatus 20 and/or apparatus 21.)

As shown in FIGS. 2D-E, distal end 302 comprises an outer tube-wall 304 shaped to define a lumen 306 thereof, and an inner tube-wall 308 disposed within lumen 306. Apparatus 300 is configured to facilitate the drawing of the portion of the pericardium into the portion of lumen 306 that is between outer tube-wall 304 and inner tube-wall 308, by application of suction through the portion of the lumen. For example, suction may be applied directly through the lumen, and/or via suction tube 30. Apparatus 300 also comprises puncturing element 50, which is configured to puncture the portion of the pericardium while the portion of the pericardium is in the portion of lumen 306 that is between outer tube-wall 304 and inner tube-wall 308. Typically, puncturing element 50 is disposed such that a distal end of the puncturing element passes between the two tube-walls. Apparatus 300 also comprises puncturing-element-restraining element 52, described hereinbelow with reference to FIGS. 4A-C.

In general, outer-tube wall 304 functions in a similar manner to sheath 60, at least in that it provides a suction port 310 through which the portion of the pericardium may be drawn. Thus, in most (but not necessarily all) applications, apparatus 300 does not include sheath 60.

Typically, distal end 302 further comprises a blunt dome-shaped cover 312, at least part of which is transparent. Cover 312 is disposed at a distal end of inner tube-wall 308 and covers space that is inside the inner tube-wall. The transparency of cover 312 facilitates imaging by imaging device 24, and the bluntness of cover 312 facilitates safe and effective advancement of guide member 23 toward the heart, as described hereinabove with respect to outer surface 17 of distal end 16 (FIG. 1). Furthermore, cover 312 helps keep the portion of the pericardium to which suction is applied from enveloping outer tube-wall 304, by applying a counteracting force to the suction.

Typically, the inner diameter D3 of outer tube-wall 304 is at least 0.2 mm and/or less than 4 mm greater than the outer diameter D5 of inner tube-wall 308. (This allows for a space between the two walls that is large enough to facilitate the application of suction, but not so large as to have an unduly-large outer diameter of outer tube-wall 304.) In some applications, the distalmost perimeter 314 of the inner tube-wall is at least 0.2 mm and/or less than 4 mm distal to the distalmost perimeter 316 of the outer tube-wall, such that, for example, height H shown in FIG. 2D is between 0.2 and 4 mm. In general, the greater distal reach of inner tube-wall 308 helps keep the portion of the pericardium to which suction is applied from enveloping outer tube-wall 304, as described hereinabove with respect to cover 312. (In particular, the greater distal reach of inner tube-wall 308 is helpful for applications in which apparatus 300 does not comprise cover 312.)

Reference is now made to FIGS. 4A-C, which are longitudinal cross-sections of apparatus 20, further showing a puncturing-element-restraining element 52, in accordance with some applications of the present invention. When puncturing the portion of the pericardium within sheath 60 (FIG. 5D), it is generally preferred that puncturing element 50 not pass out of the distal end of the sheath, in order to reduce any potential damage to the heart. In order to inhibit passage of puncturing element 50 out of sheath 60, apparatus 20 comprises puncturing-element-restraining element (e.g., a needle-restraining element) 52 shaped and positioned with respect to the puncturing element to inhibit passage of a distal tip of the puncturing element out of a distal end of the sheath. FIGS. 4A-C show needle-restraining element 52 as a rod-shaped element by way of illustration and not limitation.

As described hereinabove, apparatus 20 may comprise puncturing-element tube 32, e.g., disposed within guide tube 22. Advancement of puncturing element 50 (e.g., needle 51) distally in puncturing-element tube 32 is shown in FIG. 4B by way of illustration and not limitation. In FIG. 4B, a needle handle 48 is pushed distally to advance needle 50 within tube 22 and subsequently out of tube 22 and into the area surrounded by sheath 60. Additionally, movement of handle 48 in a distal direction engages needle-restraining element 52 with needle handle 48, as shown in FIG. 4B, to inhibit passage of needle 50 out of sheath 60. Thus, apparatus 20 is configured to reduce the possibility of puncturing element 50 injuring myocardial tissue 93 (shown in FIGS. 5A-5E). Needle-restraining element 52 may also be used for applications in which apparatus 20 does not comprise puncturing-element tube 32.

Reference is now made to FIG. 3C, which is a schematic illustration of sheath 60 and suction port 62, in accordance with some applications of the present invention. As described hereinabove with reference to FIGS. 5A-E, sheath 60 is shaped to define an at least partially distally-facing suction port 62 at the distal end of the sheath, and apparatus 20 is configured to facilitate drawing a portion of a pericardium 90 of the heart through the suction port and into the sheath. Suction port 62 defines a plane 33 that may take on various orientations with respect to the local central longitudinal axis A2 of the sheath. Typically (although not always), the preferred orientation is a function of the angle theta (FIG. 1) at which the apparatus is advanced toward the heart. In some applications, such as those involving a relatively shallow approach of the apparatus toward an anterior portion of the heart, the angle alpha between (a) axis A2, and (b) a normal N1 to plane 33, is between 40 and 70 degrees. In other applications, such as those involving a relatively steep approach of the apparatus toward a posterior portion of the heart, angle alpha is at least 0 degrees (e.g., at least 10 degrees) and/or less than 50 degrees (e.g., less than 40 degrees). Given that suction port 62 is at least partially distally-facing, alpha is always less than 90 degrees. (Most of the figures, e.g., FIG. 1, show a completely distally-facing suction port, i.e., an angle alpha of 0.)

Reference is also made to FIG. 5B. Typically, a line L1 that is 4 mm, 1 cm, or 1.5 cm long and extends from a center of suction port 62 into the sheath, in a direction parallel to axis A2, does not contact any part of apparatus 20, when suction port 62 is distal to the guide tube. (Thus, there is generally enough space in the sheath for the portion of the pericardium that is drawn in, and the tip of puncturing element 50 is generally kept at a safe distance from tissue 93 that is underneath the pericardium.) In some applications, an o-ring 61 is disposed at the suction port of the sheath, e.g., in order to help seal the interface between the suction port and the pericardium.

For some applications, at least one force sensor 63 is coupled to an inner surface of sheath 60. Force sensor 63 generates a force sensor signal responsive to contact of pericardium 90 with the inner surface of sheath 60, to determine, responsive to the signal, the degree to which the pericardium has been drawn in to sheath 60.

For some applications, portions of apparatus 20 are transparent to X-ray, to allow X-ray-based imaging techniques (including fluoroscopy) to be used to assist in navigating the apparatus. For example, outer surface 17 of distal end 16 is typically transparent to X-ray. In some applications, at least a distal portion of sheath 60 (e.g., a portion extending proximally at least 1 cm from the distal end of sheath 60) is transparent to X-ray to enable X-ray imaging of the drawing of the pericardium into sheath 60. For some such applications, needle 50 injects a contrast medium prior to the pericardium being drawn into sheath 60, which allows the drawing of the pericardium into sheath 60 to appear on X-ray. Additionally or alternatively, needle 50 injects a contrast medium into the pericardial region subsequently to puncturing the pericardium, in order to allow X-ray imaging of the heart and pericardial region.

Reference is now made to FIG. 6, which is a schematic illustration of an inflatable element 85 (e.g., a balloon) for use with apparatus 20 and 21. Inflatable element 85 is disposed over sheath 60. Inflation of inflatable element 85 facilitates the gripping of the portion of pericardium 90 by sheath 60, e.g., by increasing the area over which the suction is applied to the portion of pericardium. Element 85 may be inflated prior to puncturing element 50 puncturing the pericardium, such as to facilitate the puncturing, or subsequently to the puncturing, to keep pericardial region 92 from closing.

Reference is now made to FIGS. 7A-B and 8A-B, which are schematic illustrations of a curved needle 53 for use with applications of the present invention. For some applications, puncturing element 50 comprises a curved needle 53, in which, for example, a distal end of the needle is "J"-shaped. For some applications, curved needle 53 comprises a shape memory alloy, e.g., nitinol. For some such applications, curved needle 53 is maintained in a straight configuration prior to the puncturing of the pericardium, and assumes a curved configuration prior to puncturing the pericardium.

For some applications (FIGS. 7A-B), a rigid core structure (e.g., a straight rigid stainless steel core) 97 is disposed within curved needle 53 and maintains curved needle 53 in a straight configuration while in puncturing-element tube 32. Prior to the puncturing, curved needle 53 is advanced out of puncturing-element tube 32, typically but not necessarily together with rigid core structure 97 (FIG. 7A). The rigid core is then pulled back (and/or the needle is advanced forward), such that needle 50 assumes a curved configuration upon disengagement from the rigid core, and the pericardium is punctured (FIG. 7B).

Alternatively, curved needle 53 is surrounded by a needle casing (e.g., a straight rigid casing) 98 while disposed within puncturing-element tube 32 (FIGS. 8A-B). Casing 98 maintains needle 53 in a straight configuration until needle 53 is released from the casing. When needle 53 is advanced out of puncturing-element 32 (FIG. 8A), the rigid casing typically still surrounds needle 53 and maintains the needle in a straight configuration. Release of needle 53 from casing 98 (FIG. 8B), allows needle 53 to assume a curved configuration when puncturing the pericardium.

In FIGS. 7A-B and 8A-B, it is seen that needle 53 punctures the portion of pericardium within sheath 60 at a non-zero angle beta with respect to the longitudinal direction, rather than longitudinally, as shown in FIG. 6. It is hypothesized that, in some applications, puncturing from the side facilitates "grabbing" of the tissue during the puncture, thereby easing the act of puncturing. Alternatively or additionally, puncturing at a non-zero angle, such that the needle is not moving directly toward myocardial tissue, reduces a likelihood of inadvertent damage to the myocardium.

Although FIGS. 7A-B and 8A-B show curved needle 53 being disposed inside of puncturing-element tube 32, it is noted that core structure 97 and casing 98 may also be used without puncturing-element tube 32.

As described hereinabove with reference to FIG. 5E, following the passing of guidewire 70 into pericardial region 92, needle 51 is typically withdrawn, and a tool is then passed over the guidewire and into the pericardial region, as shown in FIG. 9 and described hereinbelow. Alternatively or additionally, a tube (not shown) is passed over the guidewire, the guidewire is withdrawn, and the tool is passed through the tube and into the pericardial region.

In some applications, the tool that is passed into pericardial region 92 includes a reflection-facilitation element, as described, for example, in US 2011/0282249 to Tsoref, which issued as U.S. Pat. No. 8,617,150 and is incorporated herein by reference. As further described in US 2011/0282249 to Tsoref, ultrasound energy may then be transmitted from within a chamber of the heart, toward the reflection-facilitation element, to ablate myocardial tissue.

In some applications, as further described hereinbelow with reference to FIGS. 9 and 11, the tool includes an expandable element, e.g., an inflatable element, such as a balloon, and/or an expandable mesh. The pericardial sac is typically lubricated against the beating heart such that navigating within the pericardial region, without the creation of a working space, may be challenging. To at least partially address this challenge, the expandable element may be expanded within pericardial region 92, in order to create a working space. Alternatively or additionally, the expandable element may be used to inhibit bleeding of the heart, by applying pressure.

In applications in which a working space is created, a surgical tool may then be passed over the guidewire and into the working space, in order to perform a surgical procedure on the heart. Creating a working space within a pericardial region, as described in the present application, is useful for facilitating various cardiac procedures, including but not limited to left atrial appendage (LAA) treatment, coronary artery bypass grafts (CABG), and bleeding reduction by application of pressure. Examples of surgical tools that may be used include a forceps, a needle, an electrosurgery tool, a cutting tool, a suction device, and a balloon. For example, FIG. 9(E) shows a balloon 185 being used to apply pressure to bleeding myocardial tissue.

Reference is now made to FIG. 9 and FIG. 11, which are schematic illustrations of apparatus 200 that creates a working space 225 between two layers of tissue, e.g., between the pericardium and myocardium (i.e., within pericardial region 92). Apparatus 200 comprises a flexible longitudinal element 202 shaped to define a lumen thereof, and an expandable element 210 (e.g., an expandable mesh, and/or an inflatable element 206) disposed at a distal portion of flexible longitudinal element 202. Expandable element 210 is shaped to define and at least partly surround working space 225, upon the expandable element being expanded. Apparatus 200 typically further comprises a surgical tool 175 shaped to be passable through the lumen of the flexible longitudinal element and into the working space. In some applications, as shown in FIG. 11, expandable element 210 is shaped to define, upon being expanded, a ring. For some applications, a surface 205 of expandable element 210 is shaped to define a rough surface rather than a smooth surface. For example, surface 205 may be shaped to define one or more grooves. Typically, when apparatus 200 is positioned within pericardial region 92, rough surface 205 reduces movement and sliding of apparatus 200 within the pericardial region 92. When disposed within the pericardial region, apparatus 200 is typically positioned between the naturally lubricated surfaces of the pericardium and the myocardium and is additionally subjected to the beating movements of the heart, both causing sliding of apparatus 200 within region 92. Therefore, rough surface 205 typically facilitates stabilizing of apparatus 200 within pericardial region 92. For some applications, both the pericardium-facing surface and the myocardium-facing surface of expandable element 210 is roughened (e.g., with grooves), while for other applications, only one of these surfaces is roughened.

Typically, apparatus 200 further comprises an imaging device 24 disposed at least partially at a distal portion of the apparatus. In some applications, imaging device 24 comprises an imaging sensor 24a disposed at the distal portion of the apparatus. (Imaging sensor 24a may be shaped to be passable through the lumen of the flexible longitudinal element.) In other applications (not shown), imaging device 24 comprises a fiber optic array having a distal end that is disposed at the distal portion of the apparatus, and an imaging sensor coupled to a proximal end of the fiber optic array. In some applications, the fiber optic array is shaped to be passable through the lumen of the flexible longitudinal element. Imaging device 24 is typically used to image working space 225 before, during, and/or following the procedure.

As shown in FIG. 11, imaging device 24 may be coupled to flexible longitudinal element 202 and/or to expandable element 210 (e.g., at a distal portion thereof). An advantage of coupling the imaging device to the expandable element (e.g., at the distal portion thereof) is that the working space may be imaged without surgical tool 175 obstructing the imaging device's line of sight.

Apparatus 200 is typically used once access to the pericardial region has been achieved by apparatus 20 or 21, or by any other means. As described hereinabove, apparatus 200 may be advanced over guidewire 70.

FIG. 9 depicts a method for performing a procedure in an area between two layers of tissue, such as in pericardial region 92 (FIG. 5E), which is between the pericardium and myocardium. Working space 225 is created by expanding expandable element 210 in the area such that the expandable element defines and at least partly surrounds the working space. Tool 175 is passed into the working space, and is used to perform the procedure. It is noted that the method depicted in FIG. 9 may be used to create a working space between other layers of tissue, such as between two layers of meninges.

For some applications, one or more substances, e.g., nanoparticles, are passed through apparatus 200 into working space 225. For some applications, the one or more substances comprise chemical and/or biological substances (e.g., therapeutic agents).

Figure 12A:
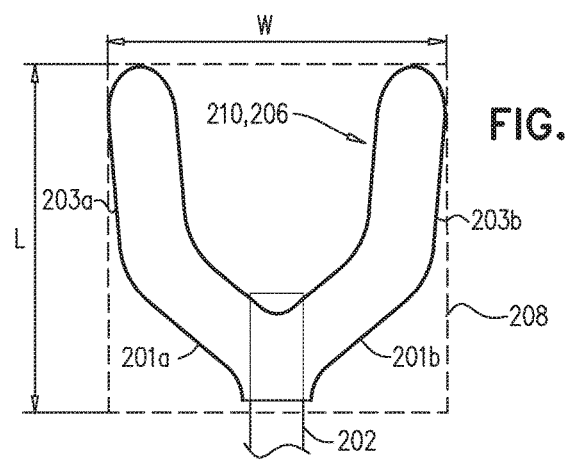

Reference is now made to FIGS. 12A-G, which show respective designs of expandable element 210, in accordance with some applications of the present invention. FIG. 12A shows an application in which expandable element 210 is shaped to define, upon being expanded, a partial ring. In the context of the claims and description of the present application, the term "partial ring" is meant to connote, in a broad sense, any shape that surrounds a space in part, but does not have a closed perimeter. In the particular case shown in FIG. 12A, the partial ring comprises proximal arms 201a and 201b, and distal arms 203a and 203b. The angle between respective proximal and distal arms may be an acute, obtuse, or right angle.

Typically, expandable element is sized and shaped to be containable within a rectangle 208 having (a) a length L between 3 and 8 cm, and (b) a width W between 3 and 8 cm, upon the expandable element being expanded.

Figure 12B:
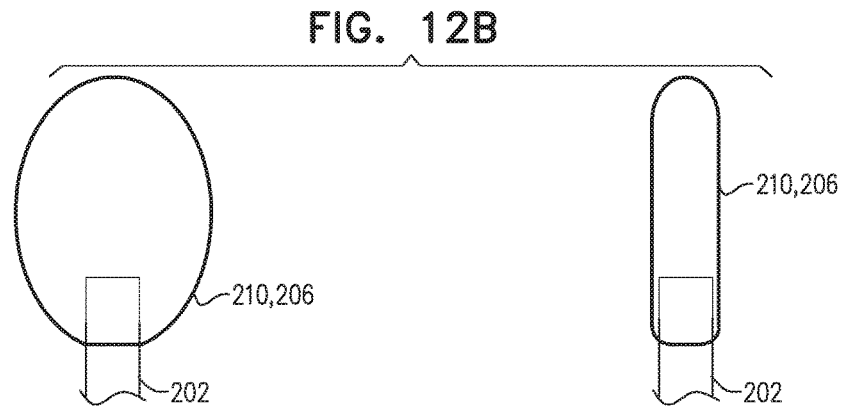

FIG. 12B shows an application in which expandable element 210 is shaped to define, upon being expanded, a disk. This disk-shaped expandable element is configured to apply pressure between two layers of tissue, e.g., to inhibit bleeding, upon being expanded. This application differs from the other applications shown in FIGS. 12A-G, in that the disk-shaped expandable element does not define a workspace. Nonetheless, in other respects (e.g., size of the expandable element, use with imaging device 24, etc.), the disk-shaped expandable element is similar to the other types of expandable element.

Figure 12C:
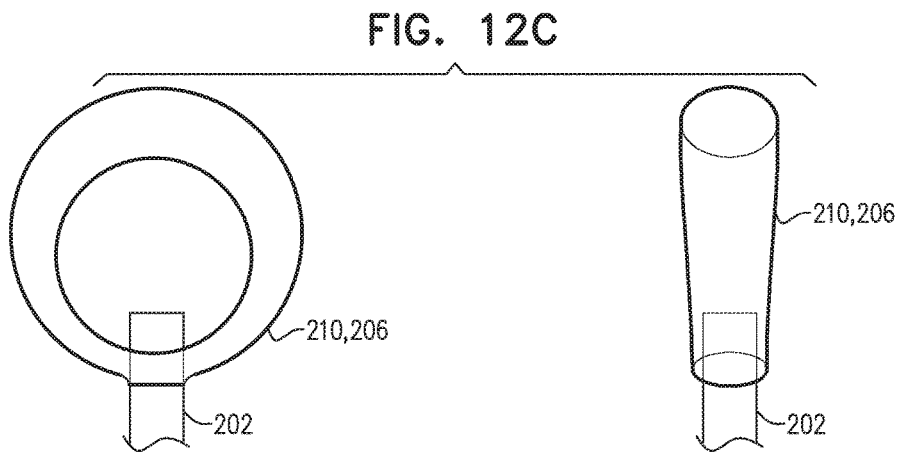
Figure 12D:
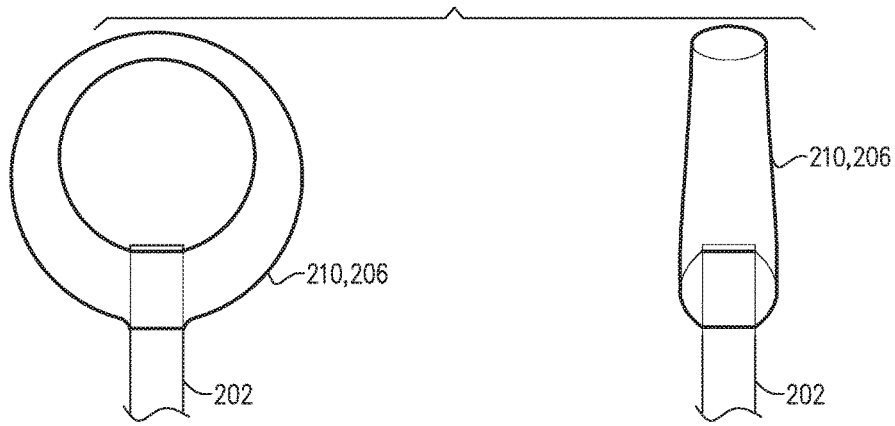
Figure 12E:
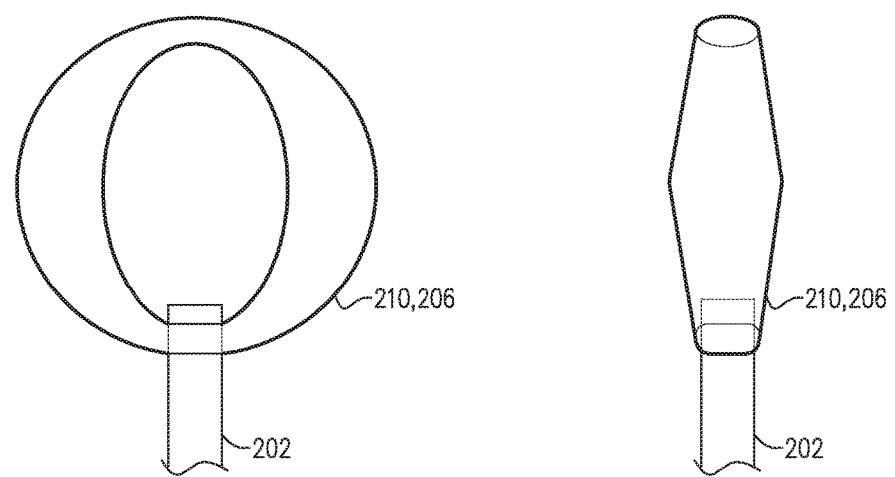
Figure 12F:
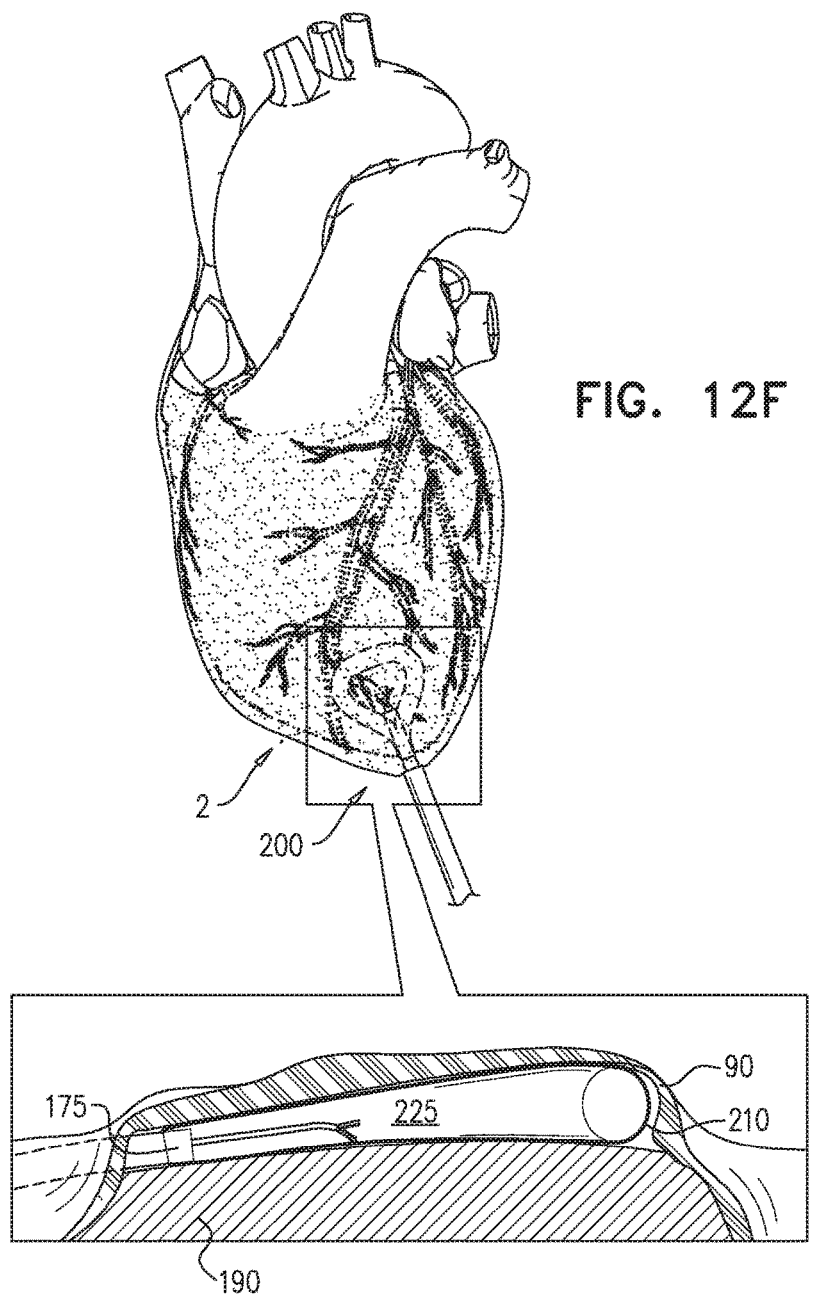

In some applications, as shown in FIG. 12C, the expandable element is configured to, upon being expanded, have a greater cross-sectional area at a distal portion thereof, relative to a proximal portion thereof. In some applications, the expandable element is configured to, upon being expanded, have a greater cross-sectional area at the proximal portion thereof, relative to the distal portion thereof (FIG. 12D). In some applications, the expandable element is configured to, upon being expanded, have a greater cross-sectional area at a middle portion thereof, relative to (a) the proximal portion thereof, and (b) the distal portion thereof (FIG. 12E). Typically, the portion with the greater cross-sectional area also has a greater height, such that the height of the working space is higher near that portion, relative to other portions of the expandable element. For example, FIG. 12F shows working space 225 having a greater height at the distal portion thereof, relative to the proximal portion thereof, when using the application of expandable element 210 shown in FIG. 12C. In general, having a non-uniform cross-section of the expandable element may facilitate the performance of certain procedures, and/or the use of certain tools.

In some applications, expandable element 210 is an expandable mesh 204 shaped to define a concave shape upon being expanded (FIG. 12G). Tool 175 is inserted through the mesh (e.g., through an opening in the mesh), or underneath the mesh, and the procedure is performed within or the below the concave shape.

In general, the various shapes and designs presented in FIGS. 12A-G may be used in combination with either expandable mesh 204 or inflatable element 206. An advantage of expandable mesh 204 is that the tool may be passed into the working space through the mesh, as shown, for example, in FIG. 12G.

Figure 13A:
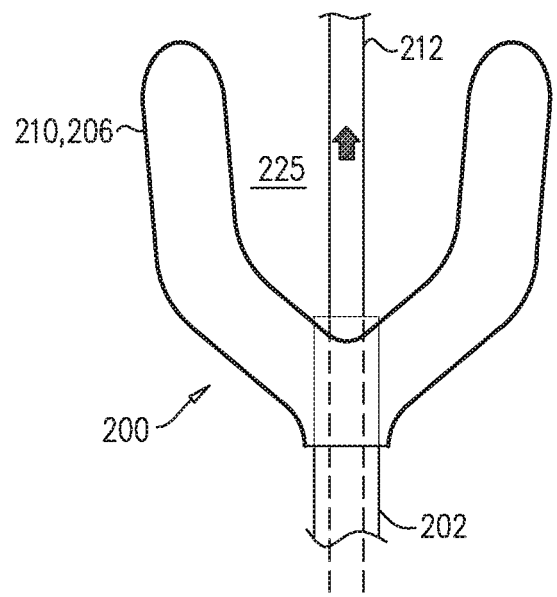
FIGS. 13A and 13B are schematic illustrations of apparatus being used to reduce flow of blood in a blood vessel, in accordance with some applications of the present invention.
Figure 13B:
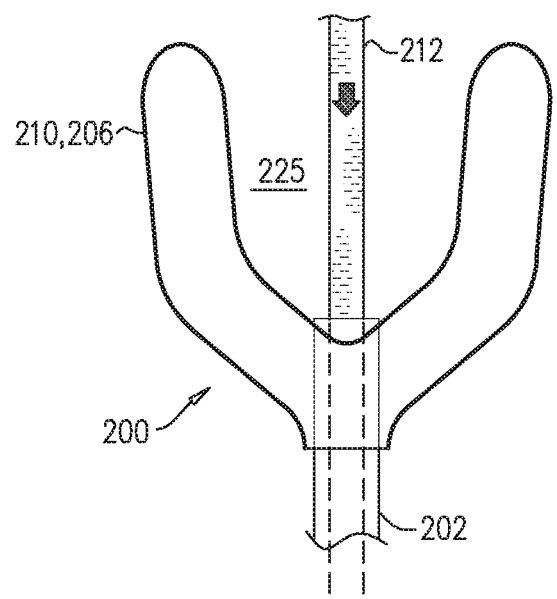

Reference is now made to FIGS. 13A-B, which are schematic illustrations of apparatus 200 being used to reduce flow of blood in a blood vessel 212, in accordance with some applications of the present invention. (The arrows in FIGS. 13A-B indicate the direction of flow of blood.) In some applications, expandable element 210 is used to reduce flow of blood in blood vessel 212, by applying pressure to the blood vessel, e.g., with a proximal portion of the expandable element.

In some applications, flow of blood toward the working space is reduced (FIG. 13A). This reduction in flow may reduce bleeding from the procedure, thus facilitating a safer procedure and faster recovery. For example, in some applications, a left atrial appendage that is at least partially contained within the working space is at least partially removed. In such applications, blood flow toward the working space may be reduced, before, during, and/or following the removal of the appendage. In other applications, flow of blood away from the working space is reduced (FIG. 13B). Such a reduction in flow might be desired, for example, following the application of a suture to blood vessel 212 within working space 225. By applying pressure to the blood vessel with the expandable element, and thus reducing flow of blood away from the working space, a resistance of the suture to pressure may be tested (i.e., the strength of the suture-tissue coupling is tested, and if necessary can be corrected during the same procedure).

In summary, applications of the present invention include performing the following series of steps: (a) creating a working space, by expanding an expandable element in an area between two layers of tissue such that the expandable element defines and at least partly surrounds the working space, (b) passing a tool into the working space, and (c) using the tool to perform a procedure, such as (i) partially removing a left atrial appendage that is at least partially contained within the working space, or (ii) applying a suture to a blood vessel, and testing a resistance of the suture to pressure, by applying pressure to the blood vessel with the expandable element.

Reference is again made to the apparatus for penetrating the pericardium of the subject which were described hereinabove. As described hereinabove with reference to FIGS. 1-8, components of apparatus 20, 21 and 300 penetrate the pericardium in order to gain access to the pericardial region.

Additional configurations of apparatus for penetrating the pericardium are described immediately hereinbelow with reference to FIGS. 15A-24J.

FIGS. 15A-D are schematic illustrations of apparatus 120 for penetrating the pericardium, as provided in accordance with some application of the present invention. Apparatus 120 is generally similar to apparatus 20, expect for differences described herein.

Similarly to apparatus 20, apparatus 120 is inserted into the subject, and is advanced distally toward the heart of the subject. It is noted that apparatus 120 may be advanced towards the heart through any suitable pathway. For example, apparatus 120 may be advanced through the subxiphoid incision, above the diaphragm, directly to the heart. Advancement of apparatus 120 is typically facilitated by an imaging device and at least one illumination-providing element, which provides illumination for the imaging device. When brought into contact with the heart of the subject, apparatus 120 is configured to facilitate drawing a portion of the pericardium of the heart into the apparatus and to puncture the portion of the pericardium in order to gain access to the pericardial region.

As shown in FIGS. 15A-D, apparatus 120 typically comprises a longitudinal guide member 220 having a proximal end 140, a distal end 160 and a guide-tube lumen 180 between proximal end 140 and distal end 160.

Typically, longitudinal guide member 220 comprises a blunt distal end 160 having an outer surface 164 at least part of which is transparent. Typically, apparatus 120 does not comprise a sheath, but rather, longitudinal guide member 220 is shaped to define a suction port. For some applications, longitudinal guide member 220 is shaped to define an at least partially distally-facing and side-facing suction port 660 at a distal portion 662 of longitudinal guide member 220. When apparatus 120 is brought into contact with the pericardium, a portion of the pericardium is drawn into longitudinal guide member 220 through suction port 660. Apparatus 120 additionally comprises a puncturing element, e.g., puncturing element 50 (shown in FIG. 5E), configured to puncture the portion of the pericardium while the portion of the pericardium is in longitudinal guide member 220.

For some applications, apparatus 120 additionally comprises a puncturing-element-restraining element (for example restraining element 52 shown in FIGS. 4A-C), shaped and positioned with respect to the puncturing element to inhibit passage of a distal tip of the puncturing element out of the distal end of longitudinal guide member 220.

Apparatus 120 is generally shaped to provide safe and efficient access to the heart. Accordingly, distal end 160 of longitudinal guide member 220 is typically blunt, rather than sharp. The bluntness of distal end 160 generally facilitates blunt dissection of tissue (i.e., generally atraumatic separation of adjacent tissues) during advancement toward the heart, and generally reduces the chances of injury to internal organs such as the diaphragm, the lungs, the stomach and the liver. Blunt distal end 160 is configured in size and shape to allow blunt dissection. In some applications, as shown in FIG. 15A, distal end 160 is shaped to define a blunt dissection tip 161. Typically, a smallest radius of curvature R4, of blunt dissection tip 161 is between 100-1000 microns, e.g., less than 500 microns. For other applications, smallest radius of curvature R4, of blunt dissection tip 161 is greater than 1 mm and/or smaller than 6 mm. This radius of curvature R4 contributes to the blunt shape of tip 161 and overall blunt shape of distal end 160 and facilitates careful separation of tissues during advancement of apparatus 120 toward the heart.

Reference is now made to FIG. 15D. Typically, but not necessarily, blunt distal end 160 is shaped to define a slanted distal end which is rotationally asymmetric with respect to a central longitudinal axis A5 of guide member 220. As shown, part of the blunt distal end 160 is shaped to define an oblique plane 96 with respect to the central longitudinal axis A5 of guide member 220. Typically, an angle alpha2 between (a) central longitudinal axis A5 of guide member 220, and (b) a normal N2 to the oblique plane defined by the blunt distal end of the guide member, is less than 70 degrees, e.g., 60 degrees. For some applications angle alpha2 between (a) central longitudinal axis A5 of guide member 220, and (b) a normal N2 to the oblique plane defined by the blunt distal end of the guide member, is at least 40 and/or less than 70 degrees. Typically, the slanted shape of distal end 160 facilitates advancement of apparatus 120 towards the heart. Additionally, the slanted shape of distal end 160 may reduce the amount of blinding reflections, by reducing the amount of light emitted from the illumination-providing element that is reflected from distal end 160 to the imaging device.

For some applications, an angle alpha2 between (a) central longitudinal axis A5 of guide member 220, and (b) a normal N2 to the oblique plane defined by the blunt distal end of the guide member, is 90 degrees (application not shown).

As noted hereinabove, at least part of blunt distal end 160 is transparent. The transparency of distal end 160 facilitates imaging by the imaging device, and the bluntness of distal end 160 facilitates safe and effective advancement of guide member 220 toward the heart.

As shown in FIGS. 15A-D, distal portion 662 of longitudinal guide member 220 is shaped to define an at least partially distally-facing and side-facing suction port 660. When apparatus 120 is brought into contact with the pericardium, apparatus 120 may be rotated, e.g., by up to 180 degrees, in order to bring the side-facing portion of the suction port into a position that is generally parallel and facing the pericardium. Contact is then made with the pericardium tissue to draw a portion of the pericardium into longitudinal guide member 220 through the suction port.

Partially distally-facing and side-facing suction port 660 typically provides improved access to the heart and facilitates drawing a portion of the pericardium into apparatus 120 from various angles and orientations. For example, port 660 facilitates accessing a posterior portion of the heart (e.g., a posterior portion of the apex) even when apparatus 120 is advanced to an anterior portion of the heart. The orientation at which apparatus 120 is advanced toward the heart is a function of the angle theta (as shown in FIG. 1 with reference to apparatus 20). Partially distally-facing and side-facing suction port 660 typically facilitates accessing the posterior side of the heart when apparatus 120 is advanced toward the heart in the orientation and at an angle theta as shown in FIG. 1. (For example, theta may be at least 30 degrees and/or less than 70 degrees.)

Additionally or alternatively, having partially side-facing port 660 allows accessing the heart non-perpendicularly (e.g., in an orientation that is generally parallel to surface of the heart).

For some applications, a length between two lying along a perimeter of side-facing suction port 660 is at least 3 mm and/or less than 20 mm, e.g., less than 15 mm.

Additionally or alternatively, providing a partially distally-facing and side-facing suction port 660 facilitates viewing of tissue through the distally-facing portion of the suction port until the portion of the pericardium is drawn into guide 220 and a suction seal is attained.

For some applications, apparatus 120 further comprises a liner 667, attached to the longitudinal guide member 220 along at least a portion of a perimeter of suction port 660. Typically, such a liner adds to the thickness of the perimeter of suction port 660 in order to ensure that suction port 660 does not define sharp ends along the perimeter thereof. For some applications, the liner comprises a plastic liner.

In any case, with or without the addition of liner 667 along the perimeter of suction port 660, the edges of suction port 660 are generally blunt and not sharp, e.g., rounded. In other words, a plurality, e.g., some or all, of tissue-contact sites along the perimeter of suction port 660, are dull in order to facilitate safe advancement of apparatus 120 toward the heart and reduce the risk of damaging and slicing into tissue during advancement of apparatus 120. For some applications, each one of the tissue-contact sites of port 660, or alternatively, only the distally-facing tissue-contact sites, have a smallest radius of curvature R5 (with or without liner 667) that is greater than 0.1 mm, e.g., greater than 0.2 mm, or between 0.1 mm and 0.2 mm. Typically, smallest radius of curvature R5 is less than 60 mm. This radius of curvature contributes to the bluntness of the perimeter of suction port 660, such that tissue-contact sites of port 660 do not damage tissue during advancement of apparatus 120. For some applications, longitudinal guide member 220 is shaped to define a tube wall 223 having a thickness T1 along at least part of the perimeter that is 40-60 microns, e.g., 50 microns. Typically, a distance D6 between two edges of perimeter of suction port 660 is between 1 and 6 mm, e.g., 4-5 mm.

For some applications, an edge of suction port 660 is shaped to define a protrusion 665 configured to inhibit slippage of the portion of a pericardium from suction port 660 when the puncturing element punctures the portion of the pericardium while the portion of the pericardium is in suction port 660. Protrusion 665 typically facilitates holding of the portion of pericardium within port 660 and longitudinal member 220. Typically protrusion 665 has a width W2 that is at least 100 microns or less than 250 microns, e.g., between 100 and 250 microns. For some applications width W2 is between 100 microns and 2 mm.

As shown in FIGS. 15B and 15C, for some applications, the edge of suction port 660 is a distal edge of the suction port, and protrusion 665 is a proximally-facing protrusion. Typically, proximally-facing protrusion 665 has a surface area of less than 1 cm2, e.g., less than 20 mm2 and greater than 1 mm2.

Reference is made to FIG. 15B. Typically, apparatus 120 comprises an imaging device 240, e.g., a camera disposed in longitudinal guide member 220. Advancement of longitudinal guide member 220 toward the heart of the subject is facilitated by imaging device 240. Typically, at least one illumination-providing element (for example, element 26 shown in FIG. 2A) provides illumination for imaging device 240. Typically, the transparency of distal end 160 facilitates the use of imaging device 240 and allows imaging of tissue beyond blunt distal end 160.

For some applications, longitudinal guide member 220 is shaped to define an imaging device chamber 822, a suction chamber 824, and a typically transparent barrier 826 for preventing fluid communication between imaging device chamber 822 and suction port 660. Imaging device 240 is disposed in the imaging device chamber and is arranged to provide simultaneous imaging of (a) suction port 660 and (b) tissue beyond blunt distal end 160, as indicated by rays 131. It is further noted that imaging device 240 is configured to additionally provide imaging through suction port 660 in order to image tissue beyond port 660 prior to drawing the portion of the pericardium into port 660.

For some applications, imaging device 240 comprises a wide-angle lens 242, e.g., a fish-eye lens, for facilitating simultaneous imaging of the suction port and the blunt distal end (and the tissue beyond the distal end). Alternatively or additionally, imaging device 240 is disposed within longitudinal guide member 220 such that an angle alpha3 between (a) central longitudinal axis A5 of guide member 220, and (b) an optical axis A6 of imaging device 240, is less than 45 degrees, e.g., 10 degrees. Positioning imaging device 240 on an angle typically facilitates simultaneous imaging of suction port 660 and blunt distal end 160 (and the tissue beyond the distal end). Additionally, transparency of barrier 826 typically allows imaging of suction port 660 and the tissue drawn into the port when device 240 is disposed in chamber 822. For some applications, angle alpha3 between (a) central longitudinal axis A5 of guide member 220, and (b) optical axis A6 of imaging device 240, is adjusted by the physician (by moving imaging device 240) in order to capture both suction port 660 and the tissue beyond distal end 160.

It is further noted that imaging of suction port 660 by imaging device 240 facilitates viewing of the portion of the pericardium that is drawn into port 660. Additionally, imaging of suction port 660 by imaging device 240 facilitates viewing of the puncturing by puncturing element 50 of the tissue that was drawn into suction port 660.

As noted hereinabove, longitudinal guide member 220 further comprises at least one illumination-providing element (for example element 26 shown in FIG. 2A). For some applications, in order to reduce the amount of blinding reflections, the at least one illumination-providing element is configured to emit collimated light.

For some applications, the at least one illumination-providing element is disposed in suction chamber 824 and not in imaging device chamber 822. Placing illumination-providing element in suction chamber 824 typically reduces the amount of blinding reflections. For some applications, barrier 826 is positioned on an angle, in order to reduce the amount of blinding reflections. For example, although barrier 826 is shown in FIG. 15B as being parallel to longitudinal axis A5, barrier 826 could instead be positioned at an angle with respect to axis A5, such that the proximal end of barrier 826 is closer than the distal end of barrier 826 to axis A5.

Alternatively or additionally, the illumination-providing element comprises an optical fiber having a distal end that is disposed at distal end 160 of longitudinal guide member 220, and a light source coupled to a proximal end of the optical fiber or disposed outside of longitudinal guide member 220 (application not shown). Such a configuration typically reduces the amount of blinding reflections.

Figure 16A:
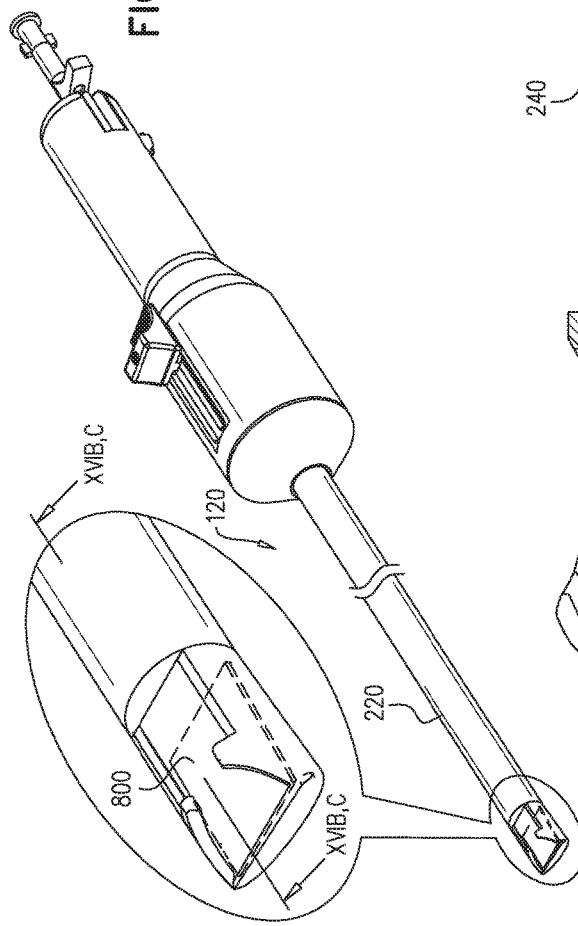
FIGS. 16A, 16B, 16C and 16D are schematic illustrations of a light-baffle for use with apparatus for penetrating a pericardium, in accordance with some applications of the present invention.
Figure 16D:
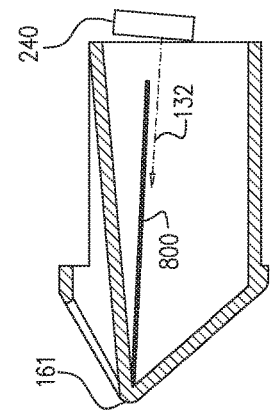
Figure 16C:
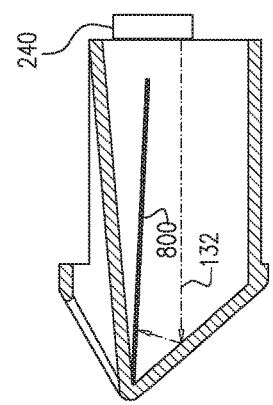
Figure 16B:
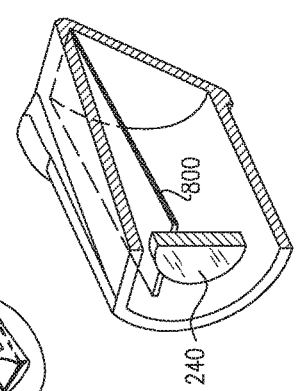

Reference is made to FIGS. 16A-D. For some applications, apparatus 120 further comprises at least one light baffle 800 disposed within longitudinal guide member 220 and arranged to reduce glare (blinding reflections) from reaching imaging device 240. Light rays 132 emitted from imaging device 240 or from illumination-providing elements that surround device 240 are typically inhibited by light baffle 800 from being reflected back onto imaging device 240 in a manner that would induce glare. For some applications, the at least one light baffle is aligned generally perpendicularly to imaging device 240, as shown (e.g., such that a normal to light baffle 800 is at an angle of greater than 75 degrees with respect to the optical axis of imaging device 240). For some applications, the normal to light baffle 800 is aligned at 90 degrees with respect to the optical axis of imaging device 240, as shown in FIG. 16B.

For some applications, imaging device 240 is positioned to face the blunt distal end of guide member 220 (blunt dissection tip 161), as shown in FIG. 16D. Additionally, as shown in FIG. 16D, baffle 800 is aligned generally perpendicularly to the center of imaging device 240.

It is noted that any factors described throughout the specification with respect to reducing blinding light reflections, typically apply to apparatus 120 as well. For example: a disposition of the at least one illumination-providing element with respect to the imaging device, an optical parameter of the distal end of the guide member, and an optical parameter of a coating on the distal end of the guide member.

Reference is again made to FIGS. 15A-D. For some applications, apparatus 120 comprises a mechanical seal, e.g., a plug, coupled to a proximal portion of the puncturing element and configured to inhibit flow of air through the puncturing element, e.g., needle 50, when suction is applied to the suction port. Allowing air to flow through a proximal portion of the needle may disrupt application of suction to the tissue. Inhibiting flow of air through the needle by using the mechanical seal typically facilitates application of suction to the tissue and allows for the needle to puncture the tissue that is drawn into the suction port. For some applications, guidewire 70 (shown in FIG. 5E) which is passed through needle 50 functions as the mechanical seal, by sealing a proximal portion of the needle and inhibiting flow of air through needle 50. Additionally or alternatively, apparatus 120 comprises a gasket coupled to the needle and configured to inhibit flow of air around the needle due to application of suction to the suction port.

Reference is made to FIGS. 17A-B, which are schematic illustrations of another configuration of apparatus for penetrating the pericardium. Apparatus 122 shown in FIGS. 17A-B typically has an entirely side-facing suction port 680 into which the portion of the pericardium is drawn. Typically edges of side port 680 inhibit slippage of tissue out of apparatus 123. In general, apparatus 122 is similar to apparatus 120 described hereinabove.

Reference is made to FIGS. 18A-B, which are schematic illustrations of another configuration of apparatus for penetrating the pericardium. Apparatus 123 shown in FIGS. 18A-B typically has suction port 670 into which the portion of the pericardium is drawn. In general, apparatus 123 is similar to apparatus 120 described hereinabove.

Reference is made to FIGS. 19A-B, which are schematic illustrations of another configuration of apparatus 126 for penetrating the pericardium.

Reference is made to FIGS. 20A-B and to FIGS. 21A-B, each of which is a schematic illustration of an additional configuration of apparatus for accessing the pericardium. Apparatus 124 shown in FIGS. 20A-B and apparatus 125 shown in FIGS. 21A-B typically have a suction hole 1130 through which suction is applied to tissue of the pericardium, and a puncturing hole 1132 through which a puncturing element is advanced to puncture the tissue. For some applications, apparatus 124 and 125 further comprise a sheath (for example sheath 60 shown in FIG. 5E) into which tissue of the pericardium is drawn due to application of suction through suction hole 1130. Puncturing element (for example needle 50 shown in FIG. 5E) is then advanced through puncturing hole 1132 to puncture the tissue in the sheath.

Figures 22A, 22B, 22C:
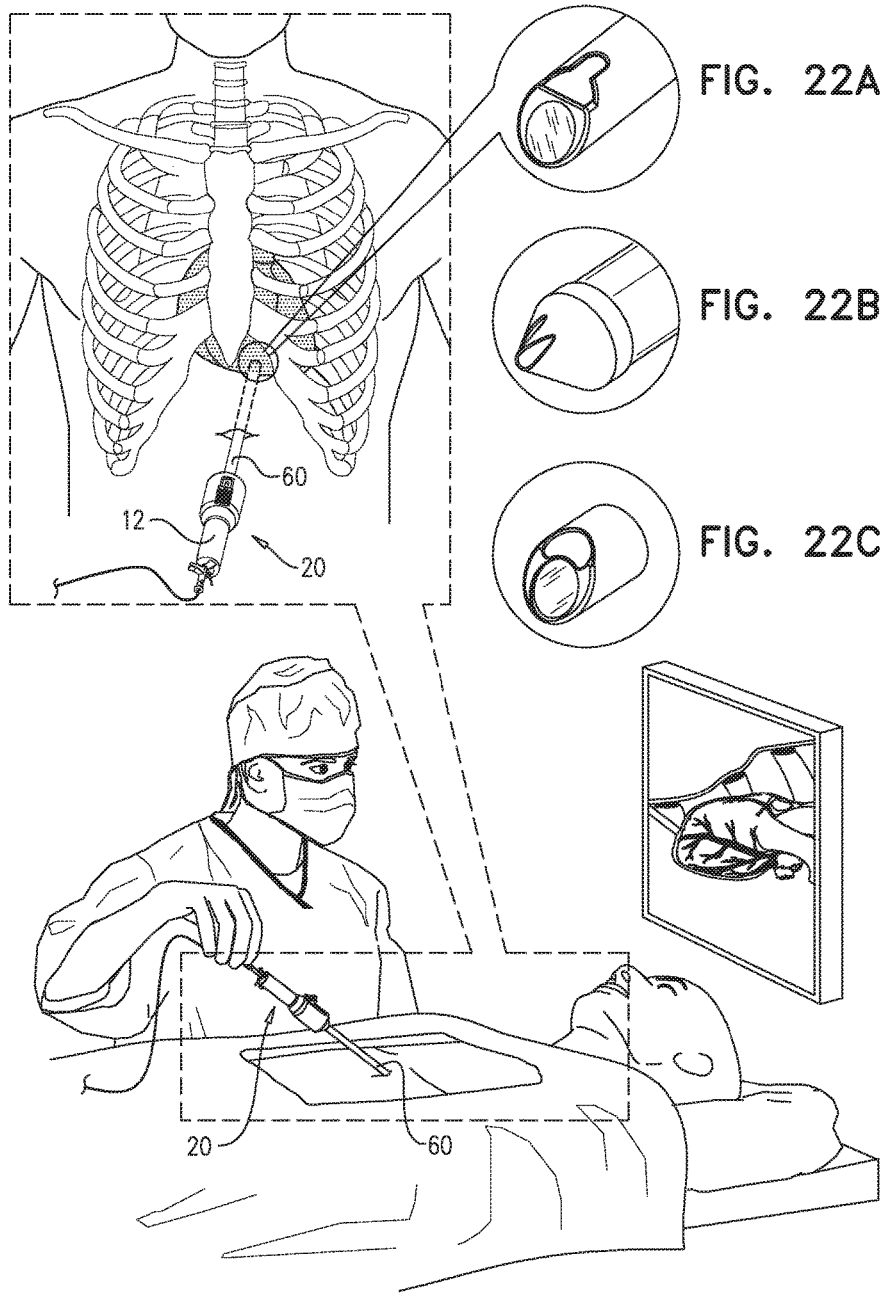

Reference is made to FIGS. 22A-C, which are respective schematic illustrations of configurations of distal portions of apparatus for accessing the pericardium, in accordance with some applications of the present invention. FIG. 22A, FIG. 22B, and FIG. 22C each shows a different geometry of the distal portion of the apparatus for accessing the pericardium.

Reference is now made to FIGS. 23A-C, which are schematic illustrations of a light reflector for use with apparatus for penetrating a pericardium, e.g., apparatus 120, in accordance with some applications of the present invention.

For some applications, a light reflector, e.g., a mirror 58, is disposed within longitudinal guide member 220, typically within imaging device chamber 822. When used, mirror 58 typically facilitates providing a wider field of view (e.g., viewing images which are not in a direct optical axis of imaging device 240), often without moving of the imaging device or adjusting focusing of device 240. For example, during advancement of apparatus 120 in a distal direction toward the heart, imaging device 240 images tissue beyond distal end 160, and mirror 58 is not used (shown in FIG. 23B). When apparatus 120 is brought into contact with the pericardium and as tissue is drawn into suction port 660, mirror 58 is in the position shown in FIG. 23C and is often used to view suction port 660 without moving imaging device 240 or adjusting focusing of the imaging device. As shown, mirror 58 typically directs light rays 134 coming from suction port 660 to imaging device 124 to facilitate imaging of suction port 660 and tissue beyond port 660.

Reference is now made to FIGS. 24A-J, which are schematic illustrations of another configuration of apparatus 120 for accessing the pericardium, and of a method for accessing a pericardial region, in accordance with some applications of the present invention.

For some applications, longitudinal guide member 220 does not comprise barrier 826 (shown in FIG. 15B) and therefore does not comprise a separate imaging device chamber and suction chamber. Instead, a distal portion 662 of longitudinal guide member 220 is shaped to define a single, undivided lumen, as shown in FIGS. 24A-J.

Figure 24D:
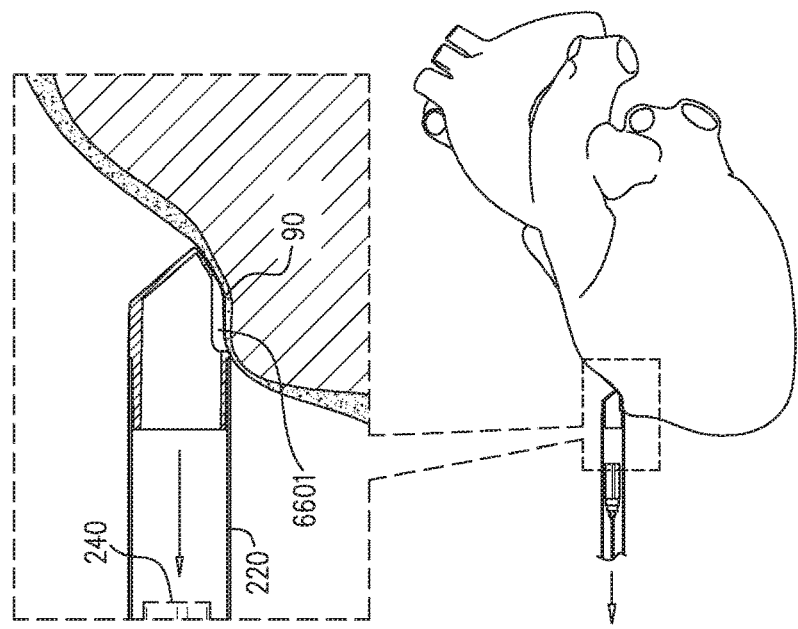

For such applications, as shown in FIG. 24A, imaging device 240 is disposed at the distal portion of longitudinal guide member 220 during advancement of longitudinal guide member 220 distally towards heart 2 of the subject. For some applications, as shown in FIG. 24A, imaging device 240 is disposed distally in longitudinal guide member 220 such that imaging device 240 is distal to at least part of suction port 6601 and at least partially blocks suction port 6601. (It is noted that in FIGS. 24A-J, suction port 6601 is shaped to define an at least partially side-facing suction port, by way of illustration and not limitation. It is noted that the suction port may be entirely distally-facing. Alternatively the suction port may be partially side-facing and partially distally-facing as described with reference to FIGS. 16A-D.)

Advancement of longitudinal guide member 220 toward heart 2 of the subject is facilitated by imaging device 240. Light rays 132 entering imaging device 240 in FIG. 24A indicate visualizing the heart during advancement of longitudinal guide member 220. Disposing imaging device 240 distally in guide member 220 (without also having puncturing element 50 disposed distally within guide member 220, as described hereinbelow with reference to FIGS. 24F-J) facilitates both having a relatively large size of imaging device 240 and enhancing imaging of heart 2 during advancement of guide member 220.

Figure 24C:
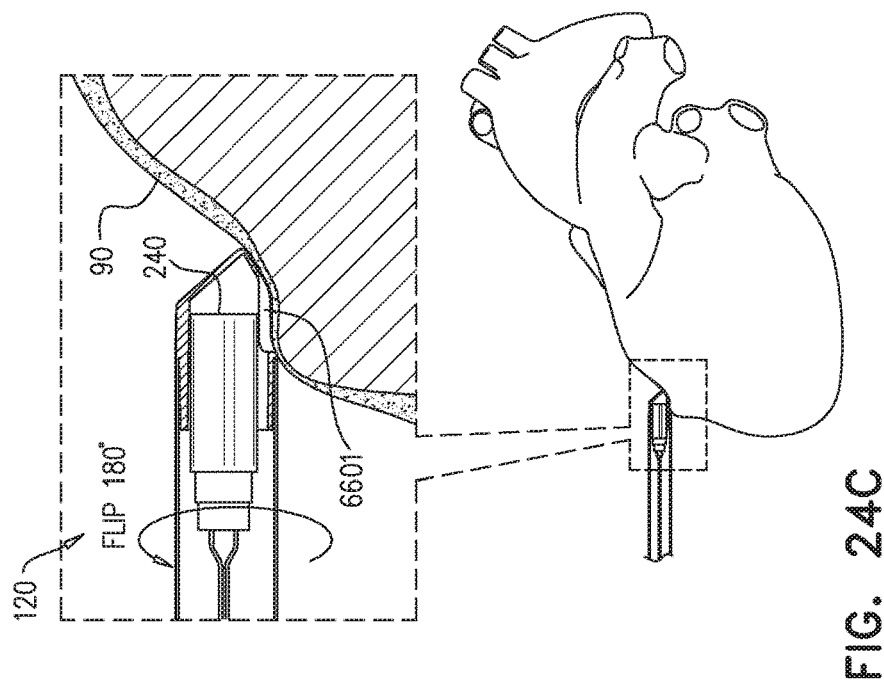

When apparatus 120 reaches heart 2 (FIG. 24B), apparatus 120 may be rotated, e.g., by up to 180 degrees, in order to bring the side-facing portion of the suction port 6601 into a position that is generally parallel to and facing the pericardium. Contact is then made between an outer surface of pericardium tissue 90 and suction port 6601 (FIG. 24C).

Figure 24F:
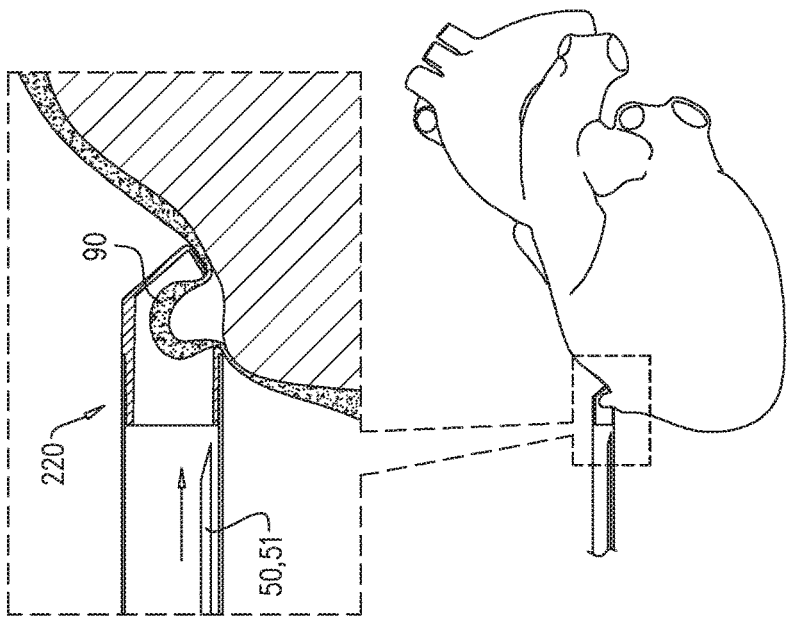
Figure 24E:
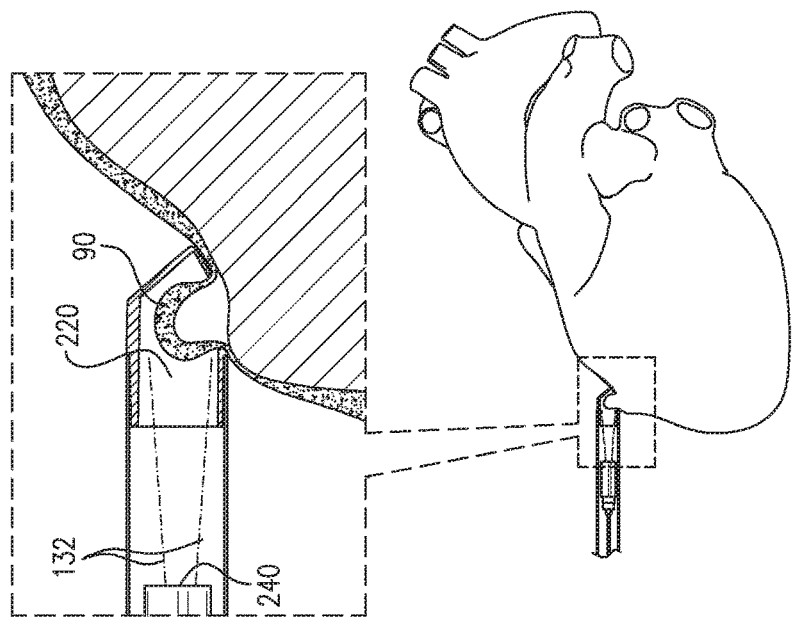

Subsequently, imaging device 240 is retracted proximally in guide member 220, such that it no longer blocks suction port 6601 (FIG. 24D) and allows drawing of a portion of pericardium 90 into guide member 220 through suction port 6601 (FIG. 24E). As shown in FIG. 24E, imaging device 240 is retracted proximally in guide member 220 such that it remains disposed in member 220 and typically generates images of suction port 6601 before, during and/or following drawing of the portion of pericardium 90 into suction port 6601. Light rays 132 entering imaging device 240 in FIG. 24E indicate visualizing of the portion of pericardium 90 that is drawn into guide member 220 through suction port 6601. It is noted that the different positions of imaging device 240 shown in (a) FIG. 24A, during advancement of the guide member toward the heart, and (b) FIG. 24E, when the pericardium is drawn into guide member 220, facilitate improved visibility for these parts of the procedure compared to if the imaging device were at a fixed position with respect to the guide member.

Reference is now made to the transition from FIG. 24E to FIG. 24F. Subsequently to drawing the portion of pericardium 90 into member 220, and while continuing to maintain the portion of pericardium 90 in guide member 220 typically by applying suction through suction port 6601, imaging device 240 is retracted proximally in guide member 220 such that it is removed from the guide member. In general, the suction may be applied actively (e.g., with a pump), or passively (e.g., with a valve which is closed to maintain previously-generated suction). As shown in FIG. 24F, when imaging device 240 has been removed from guide member 220 puncturing element 50 (e.g., a needle 51) is advanced distally to puncture the portion of pericardium 90 that is disposed in guide member 220.

It is noted that for some applications, imaging device 240 is not removed from guide member 220 following drawing of portion of the pericardium into the suction port. For such applications, imaging device 240 remains retracted proximally in guide member 220 (as shown in FIG. 24E) and puncturing element 50 is advanced distally in guide member 220 while imaging device 240 is disposed proximally in guide member 220.

Figure 24H:
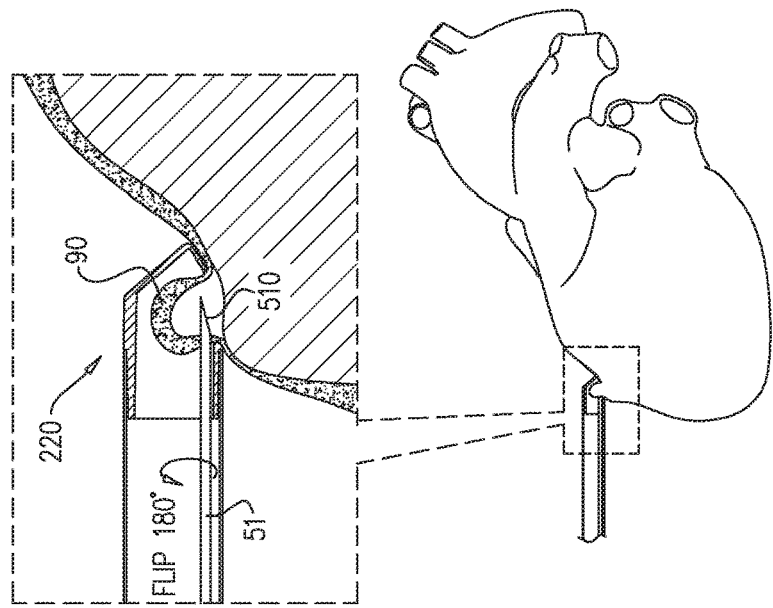
Figure 24G:
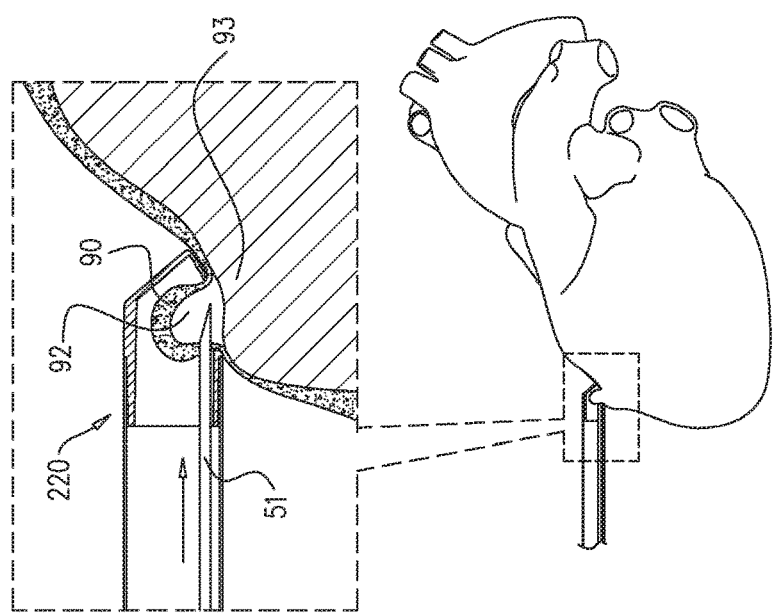

Reference is now made to FIG. 24G. FIG. 24G shows needle 51 puncturing the portion of pericardium 90 that is disposed in guide member 220. The puncturing of the portion of the pericardium provides access to pericardial region 92, e.g., a region between pericardium 90 and myocardial tissue 93.

Reference is now made to FIG. 24H. For some applications, subsequently to puncturing the portion of pericardium 90, needle 51 is typically rotated by more than 90 degrees, e.g., by 180 degrees, such that an opening 510 of needle 51 faces myocardial tissue 93. Rotating needle 51 typically places needle 51 in an improved position for passing therethrough a guidewire into pericardial region 92.

Figure 24J:
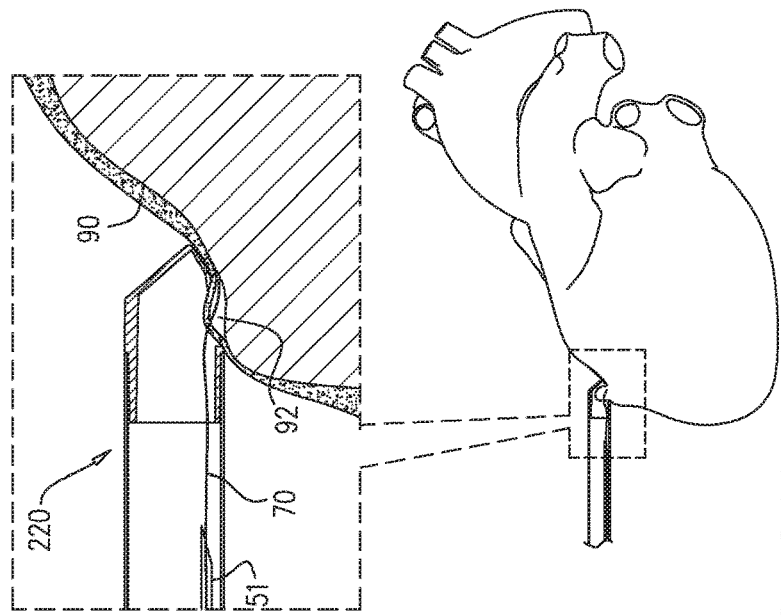
Figure 24I:
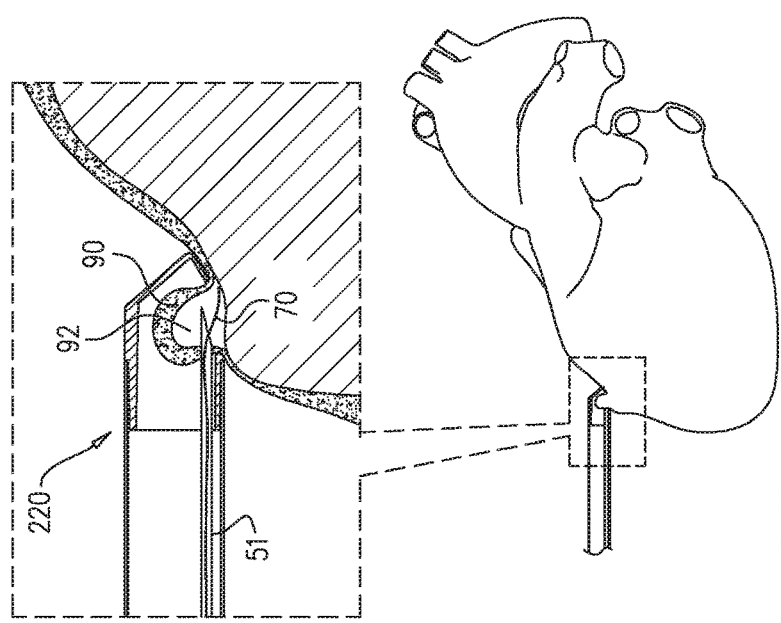

Reference is now made to FIGS. 24I-J. Typically, following the puncturing of pericardium 90, a guidewire 70 is advanced through a lumen of needle 51 and into pericardial region 92. For some applications, the needle is then withdrawn (FIG. 24J), and a tool is passed over the guidewire (application not shown).

With reference again to FIGS. 24A-J, it is noted that movement of imaging device 240 (i.e., disposing imaging device 240 distally to at least a part of suction port 6601 and subsequently retracting the imaging device proximally in guide member 220), facilitates varying a location of imaging device 240 to accommodate the needs of the operating physician. In other words, while guide member 220 is being advanced distally, imaging device 240 is disposed distally in guide member 220 in order to facilitate enhanced visualization of tissue beyond the distal end of member 220. Subsequently, in order to both allow tissue to be drawn into suction port 660 and to visualize the suction port and tissue drawn therein, imaging device 240 is moved proximally in guide member 220. Alternatively, for some applications, imaging device 240 remains entirely proximal to suction port 660 throughout the advancement of guide member 220 toward the heart.

It is noted that the use of the method described in FIGS. 24A-J with reference to movement of imaging device 240, is not limited to apparatus 120 and may be applied to other configuration of apparatus for penetrating the pericardium as described herein.

Reference is made to FIGS. 1-8B and 15A-24J. For some applications, a method is provided for assessing proper puncturing of the portion of pericardium tissue within suction port 660 (or sheath 60). Typically, a pressure sensor is used to measure a first level of negative pressure within guide member 220 (or sheath 60), once the pericardium is drawn into guide member 220 (or sheath 60). Following the puncturing of the pericardium that has been drawn into the suction port, the pressure sensor is typically used to measure a second level of negative pressure within guide member 220 (or sheath 60), and a change in the negative pressure is assessed. Advancement of the puncturing element through the portion of the pericardium is then inhibited based on the assessed change in the negative pressure, if it was identified that a magnitude of the negative pressure increased as a result of the puncturing. Alternatively or additionally, if a change in the pressure indicating that the puncturing element has punctured the pericardium is identified, then a notification of this puncturing is conveyed to the physician, indicating that the puncturing element should not be advanced farther. In either of these cases, the scope of the present invention includes using circuitry of processor 31 (FIG. 14) to identify the pressure change, and inhibit the advancement of the puncturing element, and/or generate the notification.

Apparatus and techniques described in the following references, each of which is incorporated by reference in the present application, may be combined with apparatus and techniques presented herein:

U.S. patent application Ser. No. 12/780,240, issued as U.S. Pat. No. 8,617,150;

U.S. patent application Ser. No. 14/144,265, published as US 2015-0182275;

U.S. patent application Ser. No. 13/015,951, published as US 2011/0282203 and issued as U.S. Pat. No. 8,956,346; and U.S. patent application Ser. No. 13/697,831, published as US 2013/0103028 and issued as U.S. Pat. No. 9,242,122.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   distally advancing a longitudinal guide member toward a heart of a subject, the guide member (a) shaped to define a blunt distal end having an outer surface at least part of which is transparent, and (b) shaped to define an at least partially side-facing suction port at a distal portion of the longitudinal guide member;
   during the advancing, using an imaging device disposed at least partially in the guide member to generate an image of at least part of the heart;
   contacting an outer surface of a pericardium of the heart with the suction port;
   subsequently, drawing a portion of the pericardium into the guide member by applying suction to the pericardium through the suction port;
   using the imaging device to generate an image of the suction port at at least one time selected from: (a) prior to the drawing of the portion of the pericardium into the guide member, and (b) during the drawing of the portion of the pericardium into the guide member;
   at at least one time following the drawing of the portion of the pericardium into the guide member, generating an image of the pericardium disposed within the suction port;
   puncturing the portion of the pericardium that is in the guide member using a needle;
   following the puncturing of the portion of the pericardium using the needle, rotating the needle by greater than 90 degrees such that an opening at a distal end of a lumen of the needle faces myocardium tissue of the subject; and
   subsequently, passing a guidewire through the lumen of the needle.

2. The method according to claim 1, wherein the method further comprises:
   subsequently to drawing the portion of the pericardium into the guide member and prior to puncturing the portion of the pericardium that is in the guide member using the needle,
   removing the imaging device from the guide member, while continuing to maintain the portion of the pericardium in the guide member.

3. The method according to claim 1, wherein the method further comprises, subsequently to advancing the longitudinal guide member, rotating the longitudinal guide member such that the suction port faces the pericardium.

4. The method according to claim 1, further comprising subsequently to contacting the outer surface of the pericardium of the heart with the suction port, retracting the imaging device proximally in the guide member.

5. The method according to claim 1, wherein a distal portion of the longitudinal guide member is shaped to define an undivided lumen, and wherein using an imaging device disposed at least partially in the guide member comprises using the imaging device disposed at least partially in the undivided lumen.

6. A method comprising:
   distally advancing a longitudinal guide member toward a heart of a subject, the guide member (a) shaped to define a blunt distal end having an outer surface at least part of which is transparent, and (b) shaped to define an at least partially side-facing suction port at a distal portion of the longitudinal guide member;
   during the advancing, using an imaging device disposed at least partially in the guide member to generate an image of at least part of the heart while the imaging device is disposed distally to at least part of the suction port, and is at least partially blocking the suction port;
   contacting an outer surface of a pericardium of the heart with the suction port;
   subsequently, drawing a portion of the pericardium into the guide member by applying suction to the pericardium through the suction port;
   using the imaging device to generate an image of the suction port at at least one time selected from: (a) prior to the drawing of the portion of the pericardium into the guide member, and (b) during the drawing of the portion of the pericardium into the guide member;
   at at least one time following the drawing of the portion of the pericardium into the guide member, generating an image of the pericardium disposed within the suction port; and
   puncturing the portion of the pericardium that is in the guide member using a puncturing element.

* * * * *